US011678802B2

(12) United States Patent
Coe et al.

(10) Patent No.: US 11,678,802 B2
(45) Date of Patent: Jun. 20, 2023

(54) SYSTEM AND METHOD FOR THE DISCRIMINATION OF TISSUES USING A FAST INFRARED CANCER PROBE

(71) Applicant: OHIO STATE INNOVATION FOUNDATION, Columbus, OH (US)

(72) Inventors: James Coe, Worthington, OH (US); Heather Allen, Columbus, OH (US); Charles Hitchcock, Upper Arlington, OH (US); Edward W. Martin, Delaware, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 735 days.

(21) Appl. No.: 16/085,210

(22) PCT Filed: Mar. 16, 2017

(86) PCT No.: PCT/US2017/022670
§ 371 (c)(1),
(2) Date: Sep. 14, 2018

(87) PCT Pub. No.: WO2017/161097
PCT Pub. Date: Sep. 21, 2017

(65) Prior Publication Data
US 2019/0110687 A1    Apr. 18, 2019

Related U.S. Application Data

(60) Provisional application No. 62/309,116, filed on Mar. 16, 2016.

(51) Int. Cl.
*A61B 5/00* (2006.01)
*G01N 21/552* (2014.01)
(Continued)

(52) U.S. Cl.
CPC ............ *A61B 5/0075* (2013.01); *A61B 5/444* (2013.01); *G01J 3/42* (2013.01); *G01N 21/3563* (2013.01);
(Continued)

(58) Field of Classification Search
CPC . A61B 5/0075; A61B 5/444; A61B 2090/373; A61B 2017/00061;
(Continued)

(56) References Cited

U.S. PATENT DOCUMENTS

2001/0020132 A1   9/2001 Nordstrom et al.
2001/0048077 A1   12/2001 Afanassieva
(Continued)

FOREIGN PATENT DOCUMENTS

WO    WO-2015195746 A1 * 12/2015    ......... G01N 21/255

OTHER PUBLICATIONS

Thermo Nicolet; FT-IR vs. Dispersive Infrared Theory of Infrared Spectroscopy Instrumentation (Year: 2011).*
(Continued)

*Primary Examiner* — Chao Sheng
(74) *Attorney, Agent, or Firm* — Meunier Carlin & Curfman LLC

(57) ABSTRACT

Systems and methods utilize an infrared probe and discriminating software to rapidly discriminate normal tissue processes from normal tissue during surgery, physical examination of in-situ lesions, and in the assessment of biopsy and resected tissue specimens. Examples demonstrate discrimination of cancerous from noncancerous tissues. The discriminating software, i.e. the metrics, algorithms, calibrant spectra, and decision equations, allows tissue to be identified as abnormal or normal using a minimum of infrared (IR) wavelengths in order to be measured rapidly. The probe records IR metrics approximately 1000 times faster than (Continued)

```
Perform IR Spectroscopy On A Specimen Using An ATR Probe
With A Reduced Set Of IR Wavelengths
202
```

```
Obtain An IR Spectrum Of The Specimen From The ATR Probe
204
```

```
Evaluate The Obtained IR Spectrum Using One Or More Metrics,
Wherein The One Or More Metrics Determine Normal Tissue Of
The Specimen From Abnormal Tissue
206
``` current commercial instruments, i.e. on a timescale fast enough for clinical use. The probe uses a tunable mid-infrared laser with a small set of selected wavelengths that are optimized for detecting the chemical and molecular signatures of tissue specific lesions to include, but not limited to, cancer, preneoplasia, intracellular accumulations (e.g. steatosis), inflammation, and wound healing.

37 Claims, 26 Drawing Sheets

(51) Int. Cl.
    *G01N 21/3563*     (2014.01)
    *G01J 3/42*     (2006.01)
    *A61B 90/00*     (2016.01)
    *A61B 17/00*     (2006.01)

(52) U.S. Cl.
    CPC .. *G01N 21/552* (2013.01); *A61B 2017/00061* (2013.01); *A61B 2090/373* (2016.02); *A61B 2505/05* (2013.01); *A61B 2576/00* (2013.01); *G01J 2003/425* (2013.01)

(58) Field of Classification Search
    CPC ............ A61B 2505/05; A61B 2576/00; A61B 5/0022; A61B 5/4244; A61B 5/4255; G01N 21/552; G01N 21/3563; G01N 2021/3595; G01N 21/39; G01J 3/42; G01J 2003/425; G06T 7/0012; G06T 2207/10048; G06T 2207/30088; G06T 2207/30096
    USPC ........................................ 600/407, 473, 475
    See application file for complete search history.

(56) References Cited

U.S. PATENT DOCUMENTS

| | | | |
|---|---|---|---|
| 2004/0162489 | A1 | 8/2004 | Richards-Kortum et al. |
| 2006/0253107 | A1* | 11/2006 | Hashimshony ........ A61B 5/415 606/1 |
| 2010/0130868 | A1* | 5/2010 | Hargrove ............. A61B 5/0075 600/473 |
| 2011/0103416 | A1* | 5/2011 | Patel ...................... B82Y 20/00 372/45.01 |
| 2011/0248166 | A1 | 10/2011 | Diem et al. |
| 2012/0191635 | A1* | 7/2012 | Bigio ................. G06K 9/00147 706/13 |
| 2013/0292571 | A1 | 11/2013 | Mukherjee |
| 2015/0292947 | A1* | 10/2015 | Kotidis ................ G02B 21/008 356/454 |

OTHER PUBLICATIONS

International Preliminary Report on Patentability issued for Application No. PCT/US2017/0022670, dated Sep. 27, 2018, 8 pages.
"First Insight into the Human Liver Proteome from PROTEOMFSKY-LIVERHu 1.0, a Publicly Available Database". Journal of Proteome Research 2010. 9 (1): 79-94.
Aitken, D. R.; Hinkle, G. H.; Thurston, M. O.; Tuttle, S. E.; Martin, D. T.; Olsen, J.; Haagensen, D. E.; Houchens, D.; Martin, E. W., A gamma-detecting probe for radioimmune detection of CEA-producing tumors. Successful experimental use and clinical case report. Diseases of the Colon & Rectum 1984, 27 (5), 279-282.
Allen, H. C.; Casillas-Ituarte, N. N.; Sierra-Hernandez, M. R.; Chen, X. K.; Tang, C. Y., Shedding light on water structure at air-aqueous interfaces: ions, lipids, and hydration. Physical Chemistry Chemical Physics 2009, 11 (27), 5538-5549.
Andrus and R. D. Strickland. "Cancer Grading by Fourier Transform Infrared Spectroscopy". Biospectroscopy 1998. 4 (1): 37-46.
Arnold, M. W.; Hitchcock, C. L.; Young, D.; Burak, W. E.; Bertsch, D. J.; Martin, E. W., Intra-abdominal patterns of disease dissemination in colorectal cancer identified using radioimmunoguided surgery. Diseases of the Colon & Rectum 1996, 39(5), 509-513.
Arnold, M. W.; Schneebaum, S.; Martin, E. W., Jr.; al., e., Radioimmunoguided surgery in the treatment and evaluation of rectal cancer patients. Cancer Control 1996, 3 42-45.
Arnold, M. W.; Young, D. C.; Hitchcock, C. L.; Schneebaum, S.; Martin, E. W., Radioimmunoguided surgery in primary colorectal carcinoma: an intraoperative prognostic tool and adjuvant to traditional staging. American Journal of Surgery 1995, 170 (4), 315-318.
Arnold, M.; Schneebaum, S.; Berens, A.; Petty, L.; Mojzisik, C.; Hinkle, G.; Martin, E. J., Intraoperative detection of colorectal cancer with radioimmunoguided surgery and CC49, a second-generation monoclonal antibody. Ann Surg 1992, No. 216, 627-632.
Bahlmann, C.; Patel, A.; Johnson, J.; Ni, J.; Chekkoury, A.; Khurd, P.; Kamen, A.; Grady, L.; Krupinski, E.; Graham, A.; Weinstein, R., Automated detection of diagnostically relevant regions in H&E stained digital pathology slides. Proc. SPIE 2012, 8315 (Pt. 1, Computer-Aided Diagnosis), 831504/1-831504/8.
Baker, M. J.; Trevisan, J.; Bassan, P.; Bhargava, R.; Butler, H. J.; Dorling, K. M. Fielden, P. R.; Fogarty, S. W.; Fullwood, N. J.; Heys, K. A.; Hughes, C.; Lasch, P.; Martin-Hirsch, P. L.; Obinaju, B.; Sockalingum, G. D.; Sule-Suso, J.; Strong, R. J.; Walsh, M. J.; Wood, B. R.; Gardner, P.; Martin, F. L., Using Fourier transform IR spectroscopy to analyze biological materials. Nat. Protoc. 2014, 9 (8), 1771-1791.
Barth. "Infrared Spectroscopy of Proteins". Biochim. Biophys. Acta-Bioenerg. 2007. 1767 (9): 1073-1101.
Bassan, P.; Weida, M. J.; Rowlette, J.; Gardner, P., Large scale infrared imaging of tissue micro arrays (TMAs) using a tunable Quantum Cascade Laser (QCL) based microscope. Analyst (Cambridge, U. K.) 2014, 139 (16), 3856-3859.
Bejnordi, B. E.; Litjens, G.; Timofeeva, N.; Otte-Holler, I.; Homeyer, A.; Karssemeijer, N.; van, d. L. J. A. W. M., Stain Specific Standardization of Whole-Slide Histopathological Images. IEEE Trans. Med. Imaging 2016, 35 (2), 404-15.
Benavides, F.; Oberyszyn, T. M.; VanBuskirk, A. M.; Reeve, V. E.; Kusewitt, D. F., The hairless mouse in skin research. J. Dermatol. Sci. 2009, 53 (1), 10-18.
Bennett, W. F.; Bova, J. G.; Petty, L.; Martin, E. W., Preoperative 3D Rendering of MR Imaging in Liver Metastases. Journal of Computer Assisted Tomography 1991, 15 (6), 979-984.
Bhargava, R., Infrared spectroscopic imaging: the next generation. Appl. Spectrosc. 2012, 66(10), 1091-1120.
Bhargava, R., Towards a practical Fourier transform infrared chemical imaging protocol for cancer histopathology. Anal. Bioanal. Chem. 2007, 3 89 (4), 1155.
Bhargava, R.; Kong, R., Structural and biochemical characterization of engineered tissue using FTIR spectroscopic imaging: melanoma progression as an example. In Design and Performance Validation of Phantoms Used in Conjunction with Optical Measurements of Tissue, Nordstrom, R. J., Ed. 2008; vol. 6870.
Bird, B., Infrared micro-spectral imaging: distinction of tissue types in axillary lymph node histology. BMC clinical pathology 2008, 8.
Bird, B.; Miljkovic, M.; Remiszewski, S.; Akalin, A.; Kon, M.; Diem, M., Infrared spectral histopathology (SHP): a novel diagnostic tool for the accurate classification of lung cancer. Lab. Invest. 2012, 92 (9), 1358-1373.
Burns, E. M.; Tober, K. L.; Riggenbach, J. A.; Kusewitt, D. F.; Young, G. S.; Oberyszyn, T. M., Differential effects of topical vitamin E and C E Ferulic treatments on ultraviolet light B-induced cutaneous tumor development in Skh-1 mice. PLoS One 2013, 8 (5), e63809.
Casillas-Ituarte, N. N.; Callahan, K. M.; Tang, C. Y.; Chen, X. K.; Roeselova, M.; Tobias, D. J.; Allen, H. C., Surface organization of aqueous MgC12 and application to atmospheric marine aerosol chemistry. Proc. Natl. Acad. Sci. U. S. A. 2010, 107 (15), 6616-6621.
Chekkoury, A.; Khurd, P.; Ni, J.; Bahlmann, C.; Kamen, A.; Patel, A.; Grady, L.; Singh, M.; Groher, M.; Navab, N.; Krupinski, E.; Johnson, J.; Graham, A.; Weinstein, R., Automated malignancy

(56) References Cited

OTHER PUBLICATIONS detection in breast histopathological images. Proc. SPIE 2012, 8315 (Pt. 1, Computer-Aided Diagnosis), 831515/1-831515/13.

Chen, R. Butke, B. Miller, C. L. Hitchcock, H. C. Allen, S. P. Povoski, E. W. Martin, and J. V. Coe, Infrared Metrics for Fixation-Free Liver Tumor Detection. J. Phys. Chem. B 2013. 117 (41): 12442-12450.

Chen, X. K.; Allen, H. C., Interactions of Dimethylsulfoxide with a Dipalmitoylphosphatidylcholine Monolayer Studied by Vibrational Sum Frequency Generation. Journal of Physical Chemistry A 2009, 113 (45), 12655-12662.

Chen, X. K.; Hua, W.; Huang, Z. S.; Allen, H. C., Interfacial Water Structure Associated with Phospholipid Membranes Studied by Phase-Sensitive Vibrational Sum Frequency Generation Spectroscopy. Journal of the American Chemical Society 2010, 132 (32), 11336-11342.

Chen, X.; Allen, H. C., Water Stmcture at Aqueous Solution Surfaces of Atmospherically Relevant Dimethyl Sulfoxide and Methanesulfonic Acid Revealed by Phase Sensitive Sum Frequency Spectroscopy J. Phys. Chern. B 2010, 114 (46), 14983-14988.

Cheng, R. Hironaka, D. W. A. Roberts, and J. W. Costerton. "Cytoplasmic glycogen inclusions in cells of anaerobic gram-negative rumen bacteria". Can. J. Microbiol. 1973. 19(12): 1501-1506.

Cheng, W.; Sun, D.-W.; Pu, H.; Liu, Y., Integration of spectral and textural data for enhancing hyperspectral prediction of K value in pork meat. LWT—Food Sci. Technol. 2016, 72, 322-329.

Chiriboga, L.; Xie, P.; Yee, H.; Zarou, D.; Zakim, D.; Diem, M., Infrared spectroscopy of human tissue. IV. Detection of dysplastic and neoplastic changes of human cervical tissue via infrared microscopy. Cell. Mol. Biol. 1998, 44 (1), 219-229.

Chiriboga, L.; Yee, M.; Diem, M., Infrared spectroscopy of human cells and tissue. Part VI: A comparative study of histopathology and infrared microspectroscopy of normal, cirrhotic, and cancerous liver tissue Appl. Spectrosc. 2000, 54 (1), 1-8.

Choo, L. P.; Wetzel, D. L.; Halliday, W. C.; Jackson, M.; LeVine, S. M.; Mantsch, H. H., In situ characterization of beta-amyloid in Alzheimer's diseased tissue by synchrotron Fourier transform infrared microspectroscopy. Biophys. J. 1996, 71 (Copyright (C) 2014 U.S. National Library of Medicine.), 1672-9.

Clemens, G.; Bird, B.; Weida, M.; Rowlette, J.; Baker, M. J., Quantum cascade laser-based mid-infrared spectrochemical imaging of tissues and biofluids. Spectrosc. Eur. 2014, 26 (4), 14-19.

Coe, J. V.; Chen, Z. M.; Li, R.; Butke, R.; Miller, B.; Hitchcock, C. L.; Allen, H. C.; Povoski, S. P.; Martin, E. W., Imaging Infrared Spectroscopy for Fixation-Free Liver Tumor Detection. Proc. SPIE 2014, 8947, 89470B.

Coe, J. V.; Chen, Z.; Li, R.; Nystrom, S. V.; Butke, R.; Miller, B.; Hitchcock, C. L.; Allen, H. C.; Povoski, S. P.; E. W. Martin, J., Molecular constituents of colorectal cancer metastatic to the liver by imaging infrared spectroscopy. Proceedings of SPIE, 9328 (Imaging, Manipulation, and Analysis of Biomolecules, Cells, and Tissues XIII) 2015, 93280R, 1-7.

Coe, J. V.; Nystrom, S. V.; Chen, Z.; Li, R.; Verreault, D.; Hitchcock, C. L.; Martin, E. W.; Allen, H. C., Extracting Infrared Spectra of Protein Secondary Structures Using a Library of Protein Spectra and the Ramachandran Plot. J. Phys. Chem. B 2015, 119 (41), 13079-13092.

Cohen, A. M.; Martin, E. W.; Lavery, I.; Daly, J.; Sardi, A.; Aitken, D.; Bland, K.; Mojzisik, C.; Hinkle, G.; Houchens, D. P.; Hitchcock, C. L.; Saad, A. D.; Nines, R. G.; Greenson, J. K.; Schneebaum, S.; Arnold, M. W.; Martin, E. W., Intraoperative detection of occult colon cancer micrometastases using I-125-radiolabeled monoclonal antibody CC49. Cancer 1996, 77 (4), 613-620.

Derenne, A.; Van Hemelryck, V.; Lamoral-Theys, D.; Kiss, R.; Goormaghtigh, E., FTIR Spectroscopy: A New Valuable Tool to Classify the Effects of Polyphenolic Compounds on Cancer Cells. Biochim. Biophys. Acta-Mol. Basis Dis. 2013, 1832 (1), 46-56.

Desai, D.; Arnold, M.; Saha, S.; Hinkle, G.; Soble, D.; Fry, J.; DePlatis, L.; Mantil, J.; Satter, M.; Martin, E. J., Correlative Whole-Body FDG-PET and Intraoperative Gamma Detection of FDG Distribution in Colorectal Cancer. Clinical Positron Imaging 2000, vol. 3 (No. 4), 1-9.

Diem, M.; Chiriboga, L.; Lasch, P.; Pacifico, A., IR spectra and IR spectral maps of individual normal and cancerous cells. Biopolymers 2002, 67 (4-5), 349-353.

Diem, M.; Mazur, A.; Lenau, K.; Schubert, J.; Fore, J.; Bird, B.; Miljkovic, M.; Krafft, C.; Popp, J. Molecular pathology via infrared and Raman spectral imaging, Wiley-VCH Verlag GmbH & Co. KGaA: 2014; pp. 45-102.

Diem, M.; Miljkovic, M.; Bird, B.; Chernenko, T.; Schubert, J.; Marcsisin, E.; Mazur, A.; Kingston, E.; Zuser, E.; Papamarkakis, K.; Laver, N., Applications of Infrared and Raman Microspectroscopy of Cells and Tissue in Medical Diagnostics: Present Status and Future Promises. Spectr.-Int. J. 2012, 27 (5-6), 463-496.

Duncan, F. J.; Martin, J. R.; Wulff, B. C.; Stoner, G. D.; Tober, K. L.; Oberyszyn, T. M.; Kusewitt, D. F.; van Buskirk, A. M., Topical treatment with black raspberry extract reduces cutaneous UVB-induced carcinogenesis and inflammation. Cancer Prev. Res. 2009, 2 (7), 665-672.

Ehteshami, B. B.; Balkenhol, M.; Litjens, G.; Holland, R.; Bult, P.; Karssemeijer, N.; van, d. L. J. A., Automated detection of DCIS in whole-slide H&E stained breast histopathology images. IEEE Trans. Med. Imaging 2016. 2141-2150.

Fang, L.; Holford, N. H. G.; Hinkle, G.; Cao, X.; Xiao, J. J.; Bloomston, M.; Gibbs, S.; Al Saif, O. H.; Dalton, J. T.; Chan, K. K.; Schlom, J.; Martin, E. W. J.; Sun, D., Population pharmacokinetics of humanized monoclonal antibody HuCC49DCH2 and murine antibody CC49 in colorectal cancer patients. . J. Clin. Pharmacol. 2007, 47, 227-237.

Ferlay, I. Soerjomataram, M. Ervik, et al., "GLOBOCAN 2012 v1.0, Cancer Incidence and Mortality Worldwide: IARC CancerBase No. 11", International Agency for Research on Cancer, Lyon, France, 2013.

Fernandez, R. Bhargava, S. M. Hewitt, and I. W. Levin. "Infrared Spectroscopic Imaging for Histopathologic Recognition". Nature Biotechnol. 2005. 23 (4): 469-474.

Gajjar, J. Trevisan, G. Owens, P. J. Keating, N. J. Wood, H. F. Stringfellow, P. L. Martin-Hirsch, and F. L. Martin. "Fourier-Transform Infrared Spectroscopy Coupled with A Classification Machine for the Analysis of Blood Plasma or Serum: A Novel Diagnostic Approach for Ovarian Cancer". Analyst 2013. 138 (14): 3917-3926.

Galat. "Study of the Raman scattering and infrared absorption spectra of branched polysaccharides". Acta Biochim. Pol. 1980. 27 (2): 135-142.

Gazi, E.; Baker, M.; Dwyer, J.; Lockyer, N. P.; Gardner, P.; Shanks, J. H.; Reeve, R. S.; Hart, C. A.; Clarke, N. W.; Brown, M. D., A Correlation of FTIR Spectra Derived from Prostate Cancer Biopsies with Gleason Grade and Tumour Stage. Eur. Urol. 2006, 50 (4), 750.

Gopalakrishnan, S.; Jungwirth, P.; Tobias, D. J.; Allen, H. C., Air-liquid interfaces of aqueous solutions containing ammonium and sulfate: Spectroscopic and molecular dynamics studies. J. Phys. Chem. B 2005, 109 (18), 8861-8872.

Gressel, K. L.; Duncan, F. J.; Oberyszyn, T. M.; La Perle, K. M.; Everts, H. B., Endogenous Retinoic Acid Required to Maintain the Epidermis Following Ultraviolet Light Exposure in SKH-1 Hairless Mice. Photochem. Photobiol. 2015, 91 (4), 901-908.

Haaland, D. M.; Jones, H. D. T.; Thomas, E. V., Multivariate classification of the infrared spectra of cell and tissue samples. Appl. Spectrosc. 1997, 51 (3), 340-345.

Hall, N. C.; Povoski, S. P.; Murrey, D. A.; Knopp, M. V.; Martin, E. W., Bringing advanced medical imaging into the operative arena

(56) References Cited

OTHER PUBLICATIONS could revolutionize the surgical care of cancer patients. Expert Review of Medical Devices 2008, 5 (6), 663-667.

Hall, N.; Povoski, S.; Martin, E.; Knopp, M., Combined Approach of Perioperative 18F-FDG PET/CT Imaging and Intraoperative 18F-FDG Handheld Gamma Probe Detection for Tumor Localization and Verification of Complete Tumor Resection in Breast Cancer. World Journal of Surg Oncol. 2007, vol. 5 (No. 21), 43.

Hansen, H. J.; Lafontaine, G.; Newman, E. S.; Schwartz, M. K.; Malkin, A.; Mojzisik, K.; Martin, E. W.; Goldenberg, D. M., Solving the problem of antibody interference in commercial "sandwich"-type immunoassays of carcinoembryonic antigen. Clinical Chemistry 1989, 35 (1), 146-151.

Harper, K. L.; Allen, H. C., Competition between DPPC and SDS at the air-aqueous interface. Langmuir 2007, 23 (17), 8925-8931.

Henry, J. C.; Malhotra, L.; Khabiri, H.; Guy, G.; Michaels, A.; Hanje, J.; Azevedo, M.; Bloomston, M.; Schmidt, C. R., Best radiological response to trans-arterial chemoembolization for hepatocellular carcinoma does not imply better outcomes. Hpb 2013, 15 (3), 196-202.

Hibler, B. P.; Qi, Q.; Rossi, A. M., Current state of imaging in dermatology. Semin Cutan Med Surg 2016, 35 (1), 2-8.

Hill, N. T.; Gracia-Maldonado, G. H.; Leonard, M. K.; Harper, A. R.; Tober, K. L.; Oberyszyn, T. M.; Kadakia, M. P., Role of vitamin D3 in modulation of $\Delta Np63\alpha\alpha$ expression during UVB induced tumor formation in SKH-1 mice. PLoS One 2014, 9 (9), e107052/1-e107052/11, 11 pp.

Hommel, E. L.; Allen, H. C., Broadband sum frequency generation with two regenerative amplifiers: Temporal overlap of femtosecond and picosecond light pulses. Analytical Sciences 2001, 17 (1), 137-139.

Hommel, E. L.; Ma, G.; Allen, H. C., Broadband vibrational sum frequency generation spectroscopy of a liquid surface. Analytical Sciences 2001, 17 (11), 1325-1329.

Hsu, S. H.; Yu, B.; Wang, X. M.; Lu, Y. Z.; Schmidt, C. R.; Lee, R. J.; Lee, L. J.; Jacob, S. T.; Ghoshal, K., Cationic lipid nanoparticles for therapeutic delivery of siRNA and miRNA to murine liver tumor. Nanomed.-Nanotechnol. Biol. Med. 2013, 9(8), 1169-1180.

Jones, N. B.; McNally, M. E.; Malhotra, L.; Abdel-Misih, S.; Martin, E. W.; Bloomston, M.; Schmidt, C. R., Repeat Hepatectomy for Metastatic Colorectal Cancer Is Safe but Marginally Effective. Ann. Surg. Oncol. 2012, 19 (7), 2224-2229.

Jones, N. B.; Wakely, P. E.; Klemanski, D. L.; Al-Saif, O.; Young, G.; Frankel, W. L.; Martin, E. W.; Bloomston, M., Cytopathologic evaluation of the in situ margin in patients undergoing hepatectomy. Cancer Cytopathol. 2012, 120 (6), 410-415.

Kanungo, T.; Netanyahu, N. S.; Wu, A. Y., An Efficient k-Means Clustering Algorithm: Analysis and Implementation. IEEE Transactions on Pattern Analysis and Machine Intelligence 2002, 24 (7), 881-892.

Kocak, E.; Al-Saif, O.; Satter, M.; Bloomston, M.; Abdessalam, S. F.; Mantil, J.; Goshtasby, A. A.; Martin, E. W., Image guidance during abdominal exploration for recurrent colorectal cancer. Ann. Surg. Oncol. 2007, 14 (2), 405-410.

Kohler, A.; Bertrand, D.; Martens, H.; Hannesson, K.; Kirschner, C.; Ofstad, R., Multivariate image analysis of a set of FTIR microspectroscopy images of aged bovine muscle tissue combining image and design information. Anal. Bioanal. Chem. 2007, 389 (4), 1143-1153.

Kopec, R. E.; Schick, J.; Tober, K. L.; Riedl, K. M.; Francis, D. M.; Young, G. S.; Schwartz, S. J.; Oberyszyn, T. M., Sex differences in skin carotenoid deposition and acute UVB-induced skin damage in SKH-1 hairless mice after consumption of tangerine tomatoes. Mol. Nutr. Food Res. 2015, 59 (12), 2491-2501.

Kroger, N.; Egl, A.; Engel, M.; Haase, K.; Herpich, I.; Pucci, A.; Schonhals, A.; Vogt, J.; Petrich, W.; Gretz, N.; Kranzlin, B.; Neudecker, S., Quantum cascade laser-based hyperspectral imaging of biological tissue. J Biomed Opt 2014, 19 (11), 111607.

Kwak, J. T.; Hewitt, S. M.; Kajdacsy-Balla, A. A.; Sinha, S.; Bhargava, R., Automated prostate tissue referencing for cancer detection and diagnosis. BMC Bioinformatics 2016, 17 (1), 227.

Lange, M. K.; Sandhu, A.; Sampsel, J.; Hinkle, G.; Ignaszewski, J.; Martin, E. I.; Sandhu, P.; Martin, E. W. J., Evaluation of NR-LU-10 with the neoprobe gamma detector in a mouse model J. Surg. Res. 1993, 55, 205-213.

Lasch, P.; Haensch, W.; Naumann, D.; Diem, M., Imaging of colorectal adenocarcinoma using FT-IR microspectroscopy and cluster analysis. Biochim. Biophys. Acta-Mol. Basis Dis. 2004, 1688 (2), 176-186.

Lasch P; Chiriboga L; Yee H, Diem M., Infrared Spectroscopy of Human Cells and Tissue: Detection of Disease. Technology in Cancer Research & Treatment 2002, 7 pages.

Levering, L. M.; Hayes, C. J.; Callahan, K. M.; Hadad, C. M.; Allen, H. C., Nonaqueous solvation of n-octanol and ethanol: Spectroscopic and computational studies. J. Phys. Chem. B 2006, 110 (12), 6325-6331.

Levering, L. M.; Sierra-Hernandez, M. R.; Allen, H. C., Observation of hydronium ions at the air—Aqueous acid interface: Vibrational spectroscopic studies of aqueous HCl, HBr, and HI. J. Phys. Chem. C 2007, 111 (25), 8814-8826.

Levin and R. Bhargava. "Fourier Transform Infrared Vibrational Spectroscopic Imaging: Integrating Microscopy and Molecular Recognition". Annu. Rev. Phys. Chem. 2005. 56: 429-474.

Litjens, G.; Timofeeva, N.; Hermsen, M.; Nagtegaal, I.; Hulsbergen-van, d. K. C.; Bult, P.; van, d. L. J.; Sanchez, C. I.; van, G. B.; Kovacs, I., Deep learning as a tool for increased accuracy and efficiency of histopathological diagnosis. Sci Rep 2016, 6, 26286.

Liu, D. F.; Ma, G.; Levering, L. M.; Allen, H. C., Vibrational Spectroscopy of aqueous sodium halide solutions and air-liquid interfaces: Observation of increased interfacial depth. J. Phys. Chem. B 2004, 108 (7), 2252-2260.

Ma, G.; Allen, H. C., Diffuse reflection broad bandwidth sum frequency generation from particle surfaces. Journal of the American Chemical Society 2002, 124 (32), 9374-9375.

Ma, G.; Allen, H. C., DPPC Langmuir monolayer at the air-water interface: Probing the tail and head groups by vibrational sum frequency generation spectroscopy. Langmuir 2006, 22 (12), 5341-5349.

Ma, G.; Allen, H. C., New insights into lung surfactant monolayers using vibrational sum frequency generation spectroscopy. Photochemistry and Photobiology 2006, 82 (6), 1517-1529.

Ma, G.; Chen, X. K.; Allen, H. C., Dangling OD confined in a Langmuir monolayer. Journal of the American Chemical Society 2007, 129 (45), 14053-14057.

Mackanos and C. H. Contag. "Fiber-optic probes enable cancer detection with FTIR spectroscopy". Trends in Biotechnology 2010. 28 (6): 317-323.

Martin, E. W.; James, K. K.; Hurtubise, P. E.; Catalano, P.; Minton, J. P., The use of CEA as an early indicator for gastrointestinal tumor recurrence and second-look procedures. Cancer 1977, 39 (2), 440-446.

Martin, E. W.; Kibbey, W. E.; Divecchia, L.; Anderson, G.; Catalano, P.; Minton, J. P., Carcinoembryonic antigen, clinical and historical aspects. Cancer 1976, 37 (1), 62-81.

Martin, E. W.; Minton, J. P.; Carey, L. C., CEA-directed second-look surgery in the asymptomatic patient after primary resection of colorectal carcinoma. Annals of Surgery 1985, 202 (3), 310-317.

Martin, E. W.; Tuttle, S. E.; Rousseau, M.; Mojzisik, C. M.; Odwyer, P. J.; Hinkle, G. H.; Miller, E. A.; Goodwin, R. A.; Oredipe, O. A.; Barth, R. F.; Olsen, J. O.; Houchens, D.; Jewell, S. D.; Bucci, D. M.; Adams, D.; Steplewski, Z.; Thurston, M. O., Radioimmunoguided surgery: intraoperative use of monoclonal antibody 17-1A in colorectal cancer. Hybridoma 1986, 5, S97-S108.

Martinez, D.; Barbera-Guillen, E.; LaValle, G.; Martin, E. J., Radioimmunoguided surgery for gastrointestinal malignancies: an analysis of 14 years of clinical experience. Cancer Control 1997, No. 4, 505-516.

Maziak, D. E.; Do, M. T.; Shamji, F. M.; Sundaresan, S. R.; Perkins, D. G.; Wong, P. T. T., Fourier-transform infrared spectroscopic

(56) References Cited

OTHER PUBLICATIONS study of characteristic molecular structure in cancer cells of esophagus: An exploratory study. Cancer Detect. Prev. 2007, 31 (3), 244-253.

McNally, M. E.; Martinez, A.; Khabiri, H.; Guy, G.; Michaels, A. J.; Hanje, J.; Kirkpatrick, R.; Bloomston, M.; Schmidt, C. R., Inflammatory Markers are Associated with Outcome in Patients with Unresectable Hepatocellular Carcinoma Undergoing Transarterial Chemoembolization. Ann. Surg. Oncol. 2013, 20 (3), 923-928.

Mohanaiah, P.; Sathyanarayana, P.; GuruKumar, L., Image Texture Feature Extraction Using GLCM Approach. International Journal of Scientific and Research Publications 2013, 3 (5), 1-5.

Mostaco-Guidolin, L. B.; Murakami, L. S.; Batistuti, M. R.; Nomizo, A.; Bachmann, L., Molecular and Chemical Characterization by Fourier Transform Infrared Spectroscopy of Human Breast Cancer Cells with Estrogen Receptor Expressed and Not Expressed. Spectr.-Int. J. 2010, 24 (5), 501-510.

Nagarajan, P.; Tober, K. L.; Riggenbach, J. A.; Kusewitt, D. F.; Lehman, A. M.; Sielecki, T.; Pruitt, J.; Satoskar, A. R.; Oberyszyn, T. M., MIF Antagonist (CPSI-1306) Protects against UVB-induced Squamous Cell Carcinoma. Mol. Cancer Res. 2014, 12(9), 1292-1302.

Nieroda, C. A.; Mojzisik, C.; Sardi, A.; Farrar, W. B.; Hinkle, G.; Siddiqi, M. A.; Ferrara, P. J.; James, A.; Schlom, J.; Thurston, M. O.; Martin, E. W., Staging of carcinoma of the breast using a hand-held gamma detecting probe and monoclonal antibody B72.3. Surgery Gynecology & Obstetrics 1989, 169 (1), 35-40.

Oberyszyn, T. M.; Sabourin, C. L. K.; Bijur, G. N.; Oberyszyn, A. S.; Boros, L. G.; Robertson, F. M., Interleukin-1a gene expression and localization of interleukin-1α protein during tumor promotion. Mol. Carcinog. 1993, 7 (4), 238-48.

Petibois and B. Desbat. "Clinical Application of FTIR Imaging: New Reasons for Hope". Trends Biotechnol. 2010. 28 (10): 495-500.

Povoski, S. P.; Neff, R. L.; Mojzisik, C. M.; O'Malley, D. M.; Hinkle, G. H.; Hall, N. C.; Murrey, D. A.; Knopp, M. V.; Martin, E. W., A comprehensive overview of radioguided surgery using gamma detection probe technology. World Journal of Surgical Oncology 2009, 7.

Rigas, S. Morgello, I. S. Goldman, and P. T. T. Wong. "Human Colorectal Cancers Display Abnormal Fourier-Transform Infrared Spectra". Proc. Natl. Acad. Sci. U.S.A. 1990. 87 (20): 8140-8144.

Riordan, D. P.; Varma, S.; West, R. B.; Brown, P. O., Automated analysis and classification of histological tissue features by multidimensional microscopic molecular profiling. PLoS One 2015, 10 (7), e0128975/1-e0128975/18.

Rogers, H. W.; Weinstock, M. A.; Feldman, S. R.; Coldiron, B. M., Incidence estimate of nonmelanoma skin cancer (keratinocyte carcinomas) in the us population, 2012. JAMA Dermatology 2015, 151 (10), 1081-1086.

Sattlecker, M.; Stone, N.; Bessant, C., Current trends in machine-learning methods applied to spectroscopic cancer diagnosis. TrAC, Trends Anal. Chem. 2014, 59, 17-25.

Schmidt, C. R.; Shires, P.; Mootoo, M., Real-time ultrasound imaging of irreversible electroporation in a porcine liver model adequately characterizes the zone of cellular necrosis. Hpb 2012, 14 (2), 98-102.

Sickle-Santanello, B. J.; Odwyer, P. J.; Mojzisik, C.; Tuttle, S. E.; Hinkle, G. H.; Rousseau, M.; Schlom, J.; Colcher, D.; Thurston, M. O.; Nieroda, C.; Sardi, A.; Farrar, W. B.; Minton, J. P.; Martin, E. W., Radioimmunoguided surgery using the monoclonal antibody B72.3 in colorectal tumors. Diseases of the Colon & Rectum 1987, 30 (10), 761-764.

Sierra-Hernandez, M. R.; Allen, H. C., Incorporation and Exclusion of Long Chain Alkyl Halides in Fatty Acid Monolayers at the Air-Water Interface. Langmuir 2010, 26 (24), 18806-18816.

Siqueira, L. F. S.; Lima, K. M. G., MIR-biospectroscopy coupled with chemometrics in cancer studies. Analyst (Cambridge, U. K.) 2016, 141 (16), 4833-4847.

Srinivasan, G.; Bhargava, R., Fourier transform-infrared spectroscopic imaging: The emerging evolution from a microscopy tool to a cancer imaging modality. Spectr.-Int. J. 2007, 22 (7), 30-43.

Stern, R. S., Prevalence of a history of skin cancer in 2007: Results of an incidence-based model. Arch. Dermatol. 2010, 146 (3), 279-282.

Sulé-Suso, J.; Skingsley, D.; Sockalingum, G. D.; Kohler, A.; Kegelaer, G.; Manfait, M.; El Haj, A. J., FT-IR microspectroscopy as a tool to assess lung cancer cells response to chemotherapy. Vib. Spectrosc 2005, 38 (1-2), 179.

Sullivan, N. J.; Tober, K. L.; Burns, E. M.; Schick, J. S.; Riggenbach, J. A.; Mace, T. A.; Bill, M. A.; Young, G. S.; Oberyszyn, T. M.; Lesinski, G. B., UV Light B-Mediated Inhibition of Skin Catalase Activity Promotes Gr-1+CD11b+ Myeloid Cell Expansion. J. Invest. Dermatol. 2012, 132 (3-1), 695-702.

Sun, D.; Bloomston, M.; Hinkle, G.; Al-Saif, O. H.; Hall, N. C.; Povoski, S. P.; Arnold, M. W.; Martin, E. W., Radioimmunoguided surgery (RIGS), PET/CT image-guided surgery, and fluorescence image-guided surgery: Past, present, and future. J Surg Oncol 2007, 96 (4), 297-308.

Sun, X. L.; Xu, Y. Z.; Wu, J. G.; Zhang, Y. F.; Sun, K. L., Detection of Lung Cancer Tissue by Attenuated Total Reflection-Fourier Transform Infrared Spectroscopy—A Pilot Study of 60 Samples. J. Surg. Res. 2013, 179 (1), 33-38.

Tahir, M. A.; Bourdidane, A.; Kurugollu, F., An FPGA Based Coprocessor for GLCM and Haralick Texture Features and their Application in Prostate Cancer Classification. Analog Integrated Circuits and Signal Processing 2005, 43, 205-215.

Tang, C. Y.; Allen, H. C., Ionic Binding of Na+ versus K+ to the Carboxylic Acid Headgroup of Palmitic Acid Monolayers Studied by Vibrational Sum Frequency Generation Spectroscopy. Journal of Physical Chemistry A 2009, 113 (26), 7383-7393.

Tang, C. Y.; Huang, Z. S. A.; Allen, H. C., Binding of Mg2+ and Ca2+ to Palmitic Acid and Deprotonation of the COOH Headgroup Studied by Vibrational Sum Frequency Generation Spectroscopy. J. Phys. Chem. B 2010, 114 (51), 17068-17076.

Tatulian. "Structural Characterization of Membrane Proteins and Peptides by FTIR and ATR-FTIR Spectroscopy". Methods Mol. Biol. 2013. 974: 177-218.

Tian, P.-r.; Zhang, W.-t.; Xu, Z., Recent progress in diagnosis of malignant tumors by Fourier transform infrared spectroscopy. Guangpuxue Yu Guangpu Fenxi 2014, 34 (10), 2627-2631. English abstract included.

Tiwari, S.; Bhargava, R., Extracting knowledge from chemical imaging data using computational algorithms for digital cancer diagnosis. Yale J Biol Med 2015, 88 (2), 131-43.

Tobin, M.; Chesters, A.; Chalmers, J. M.; al., a. e., Infrared microscopy of epithelial cancer cells in whole tisses and in tissue culture, using synchrotron radiation. Faraday Discuss. 2003, 126, 27-39.

Tuttle, S. E.; Jewell, S. D.; Mojzisik, C. M.; Hinkle, G. H.; Colcher, D.; Schlom, J.; Martin, E. W., Intraoperative radioimmunolocalization of colorectal carcinoma with a hand-held gamma probe and MAb B72.3: comparison of in vivo gamma probe counts with in vitro MAb radiolocalization. International Journal of Cancer 1988, 42 (3), 352-358.

Ukkonen, H.; Kumar, S.; Mikkonen, J.; Salo, T.; Singh, S. P.; Koistinen, A. P.; Goormaghtigh, E.; Kullaa, A. M., Changes in the microenvironment of invading melanoma and carcinoma cells identified by FTIR imaging. Vib. Spectrosc. 2015, 79, 24-30.

Van Loon, L. L.; Allen, H. C.; Wyslouzil, B. E., Effective Diffusion Coefficients for Methanol in Sulfuric Acid Solutions Measured by Raman Spectroscopy. Journal of Physical Chemistry A 2008, 112 (43), 10758-10763.

Voss, L. F.; Bazerbashi, M. F.; Beekman, C. P.; Hadad, C. M.; Allen, H. C., Oxidation of oleic acid at air/liquid interfaces. Journal of Geophysical Research-Atmospheres 2007, 112 (D6).

Walsh, M. J.; German, M. J.; Singh, M.; Pollock, H. M.; Hammiche, A.; Kyrgiou, M.; Stringfellow, H. F.; Paraskevaidis, E.; Martin-Hirsch, P. L.; Martin, F. L., IR microspectroscopy: potential applications in cervical cancer screening. Cancer Lett. 2007, 246 (1-2), 1-11.

(56) References Cited

OTHER PUBLICATIONS

Walsh, M. J.; Mayerich, D.; Kajdacsy-Balla, A.; Bhargava, R., High-resolution mid-infrared imaging for disease diagnosis. In Biomedical Vibrational Spectroscopy V: Advances in Research and Industry, MahadevanJansen, A.; Petrich, W., Eds. 2012; vol. 8219.

Walsh, M. J.; Nasse, M. J.; Pounder, F. N.; Macias, V.; Kajdacsy-Balla, A.; Hirschmugl, C.; Bhargava, R., Synchrotron FTIR Imaging For The Identification Of Cell Types Within Human Tissues. In Wirms 2009: 5th International Workshop on Infrared Microscopy and Spectroscopy with Accelerator Based Sources, PredoiCross, A.; Billinghurst, B. E., Eds. 2010; vol. 1214, pp. 105-107

Walsh, M. J.; Reddy, R. K.; Bhargava, R., Label-Free Biomedical Imaging With Mid-IR Spectroscopy. IEEE Journal of Selected Topics in Quantum Electronics 2012, 18(4), 1502-1513.

Woess, C.; Drach, M.; Villunger, A.; Tappert, R.; Stalder, R.; Pallua, J. D., Application of mid-infrared (MIR) microscopy imaging for discrimination between follicular hyperplasia and follicular lymphoma in transgenic mice. Analyst (Cambridge, U. K.) 2015, 140 (18), 6363-6372.

Wong, P. T. T.; Cadrin, M.; French, S. W., Distinctive Infrared Spectral Features in Liver-Tumor Tissue of Mice—Evidence of Structural Modifications at the Molecular Level. Experimental and Molecular Pathology 1991, 55 (3), 269-284.

Wood, B. R.; Quinn, M. A.; Burden, F. R.; McNaughton, D., An investigation into FTIR spectroscopy as a biodiagnostic tool for cervical cancer. Biospectroscopy 1996, 2 (3), 143-153.

Xiao, J.; Horst, S.; Hinkle, G.; Cao, X.; Kocak, E.; Fang, J.; Young, D.; Khazaeli, M.; Agnese, D.; Sun, D.; Martin, E., Jr., Pharmacokinetics and clinical evaluation of 125I radiolabled humanized CC49 monocolonal antibody (HuCC49DCH2) in reccurent and metastatic colorectal cancer patients. Cancer Bioth. Radiopharm. 2005, 20, 16-26.

Xu, M.; Larentzos, J. P.; Roshdy, M.; Criscenti, L. J.; Allen, H. C., Aqueous divalent metal-nitrate interactions: hydration versus ion pairing. Physical Chemistry Chemical Physics 2008, 10 (32), 4793-4801.

Yano, S. Ohoshima, Y. Shimizu, T. Moriguchi, and H. Katayama. "Evaluation of glycogen level in human lung carcinoma tissues by an infrared spectroscopic method". Cancer Lett. (Shannon, Irel.) 1996. 110 (1,2): 29-34.

Yeh, K.; Kenkel, S.; Liu, J.-N.; Bhargava, R., Fast Infrared Chemical Imaging with a Quantum Cascade Laser. Anal. Chem. (Washington, DC, U. S.) 2015, 87 (1), 485-493.

Yeh, K.; Schulmerich, M.; Bhargava, R., Mid-infrared micro spectroscopic imaging with a quantum cascade laser. Proc. SPIE 2013, 8726 (Next-Generation Spectroscopic Technologies VI), 87260E/1-87260E/7.

Zamcheck, N.; Martin, E. W., Factors controlling the circulating CEA levels in pancreatic cancer: some clinical correlations. Cancer 1981, 47 (6), 1620-1627.

Extended European Search Report issued for European Application No. EP 17767510.5, dated Oct. 28, 2019, 17 pages.

Lucas, et al., "Black glasses, bulk and fibers: Obtaining information in the infrared", Mat Today, Elsevier, 3:1, 3-6.

Communication Pursuant to Article 94(3) EPC, issued for Application No. 17767510.5, dated Sep. 25, 2020.

International Searching Authority of the U.S Patent and Trademark Office. International Search Report and Written Opinion. Application No. PCT/US2017/022670. dated Jun. 12, 2017. 10 pages.

Communication Pursuant to Article 94(3) EPC, issued for Application No. 17767510.5, dated Jun. 9, 2022.

\* cited by examiner

```
┌─────────────────────────────────────────────────────┐
│ Perform IR Spectroscopy On A Specimen Using An ATR Probe │
│           With A Reduced Set Of IR Wavelengths       │
│                         202                          │
└─────────────────────────────────────────────────────┘
                            │
                            ▼
┌─────────────────────────────────────────────────────┐
│    Obtain An IR Spectrum Of The Specimen From The ATR Probe │
│                         204                          │
└─────────────────────────────────────────────────────┘
                            │
                            ▼
┌─────────────────────────────────────────────────────┐
│  Evaluate The Obtained IR Spectrum Using One Or More Metrics, │
│  Wherein The One Or More Metrics Determine Normal Tissue Of  │
│           The Specimen From Abnormal Tissue          │
│                         206                          │
└─────────────────────────────────────────────────────┘
```

FIG. 2

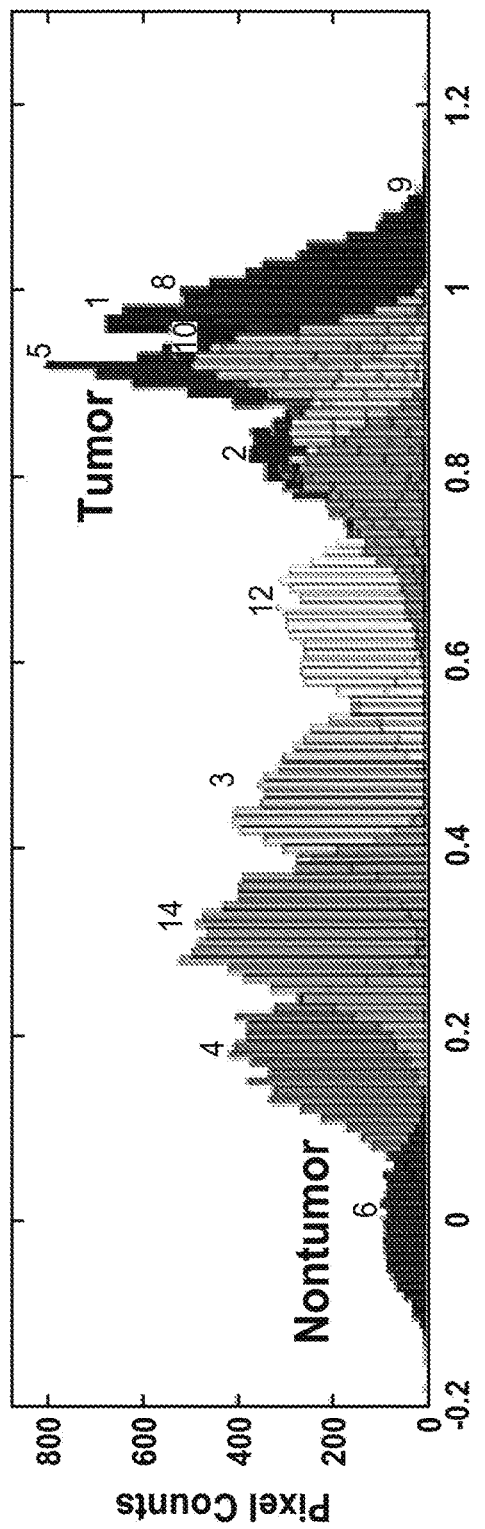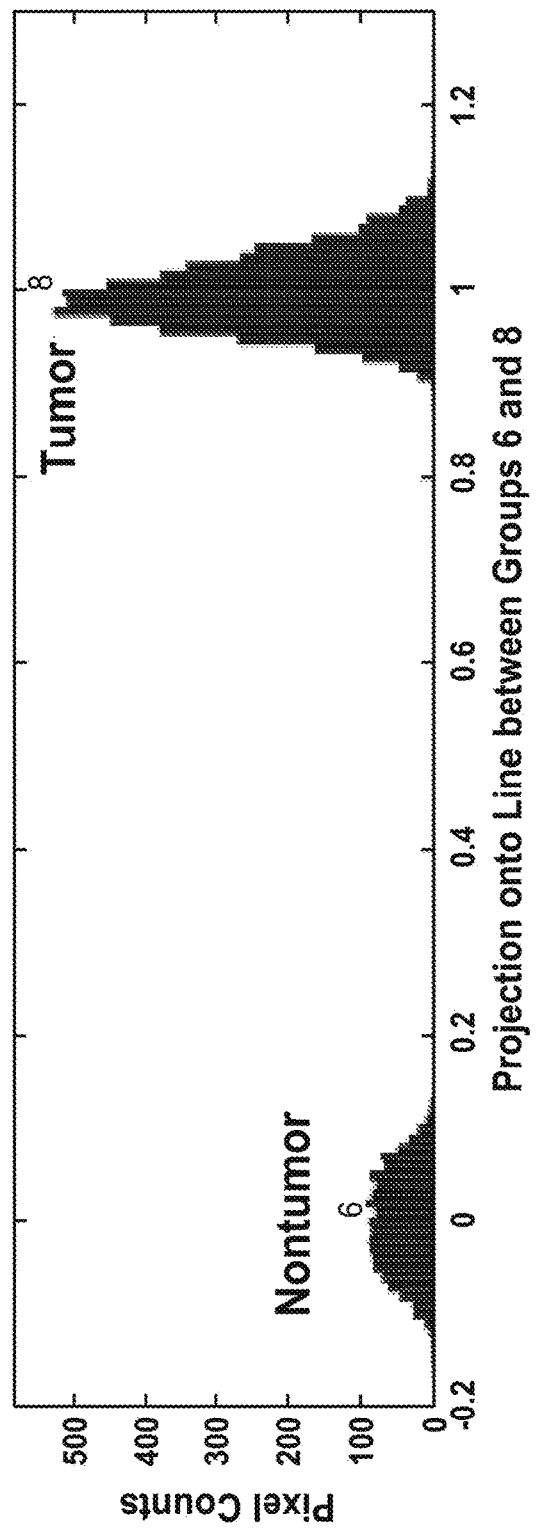
FIG. 18C
FIG. 18D

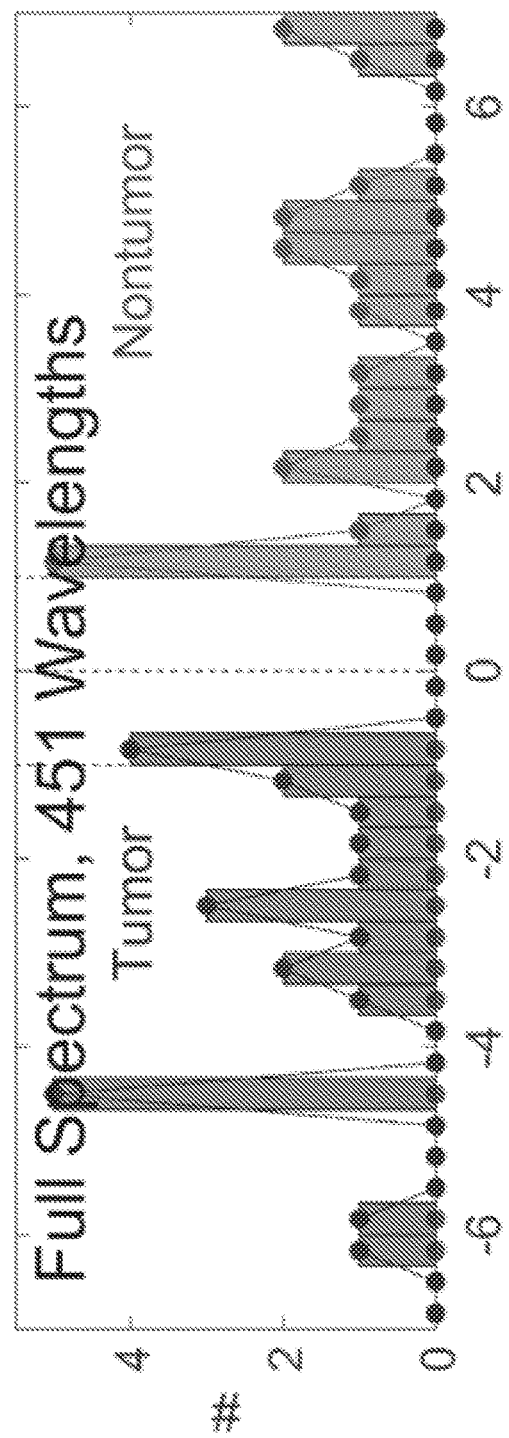
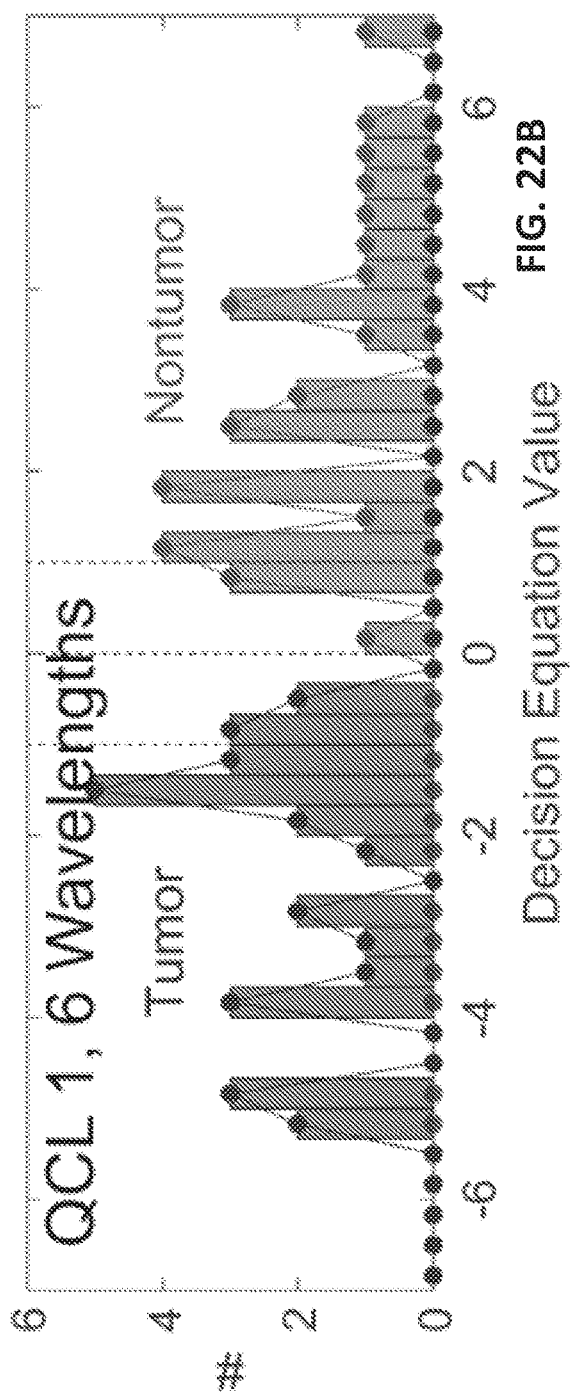
FIG. 22A
FIG. 22B

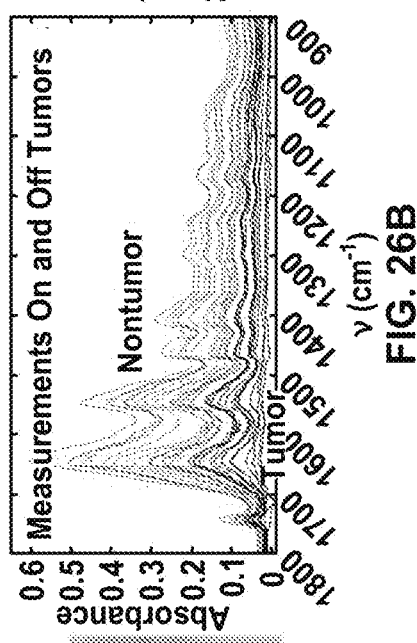
FIG. 26A
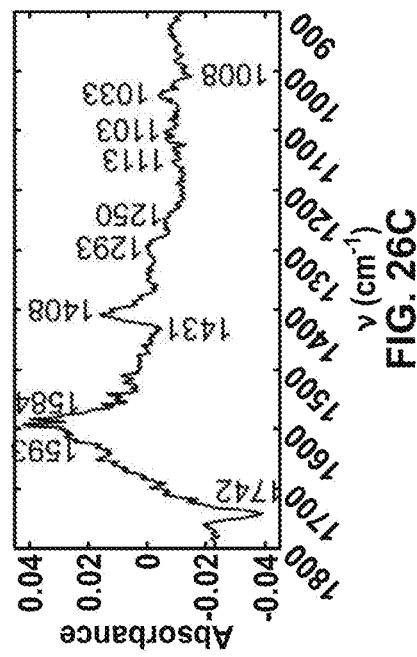
FIG. 26B
FIG. 26C
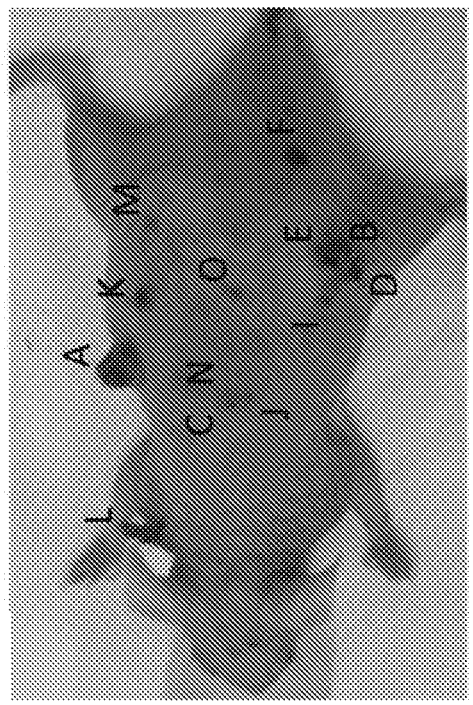
FIG. 27A
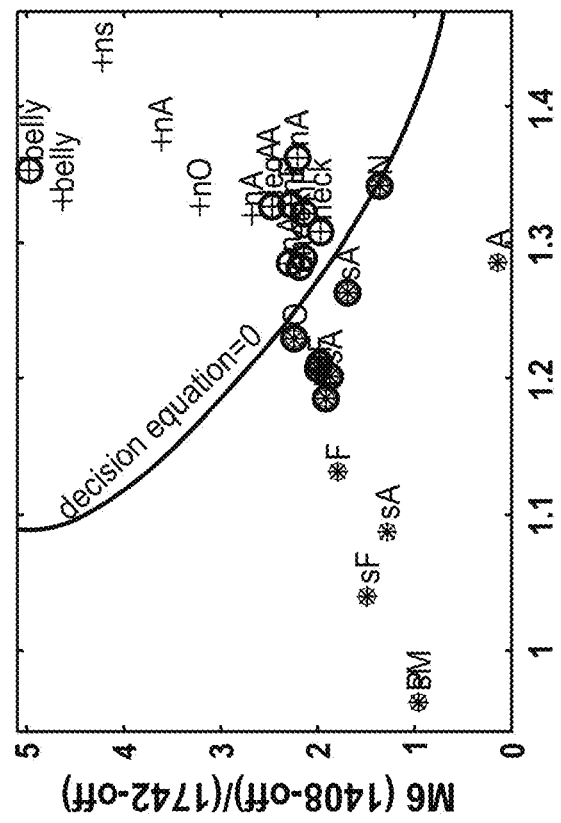
FIG. 27B

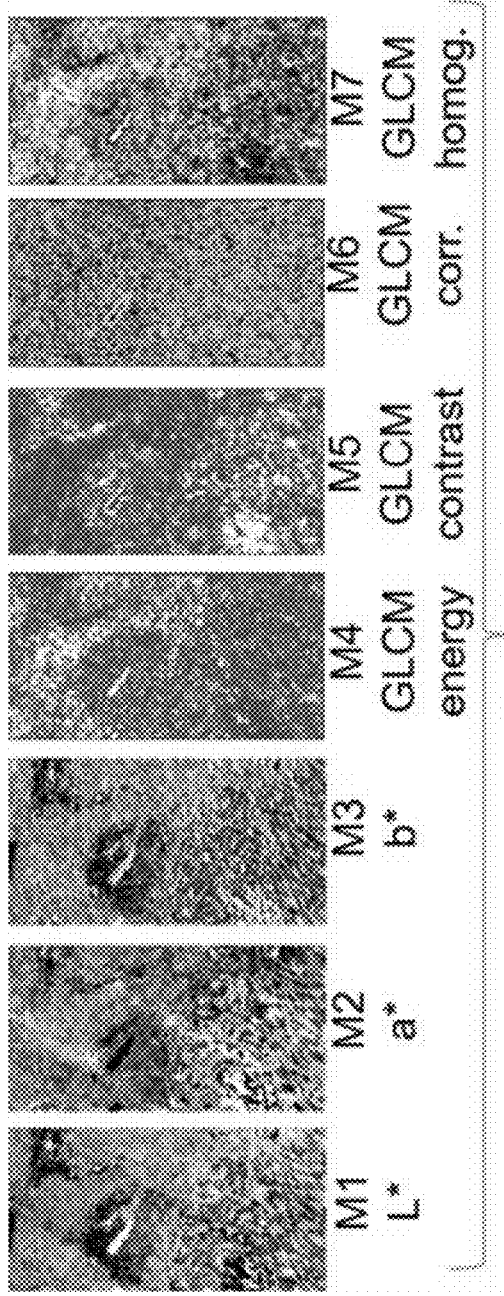
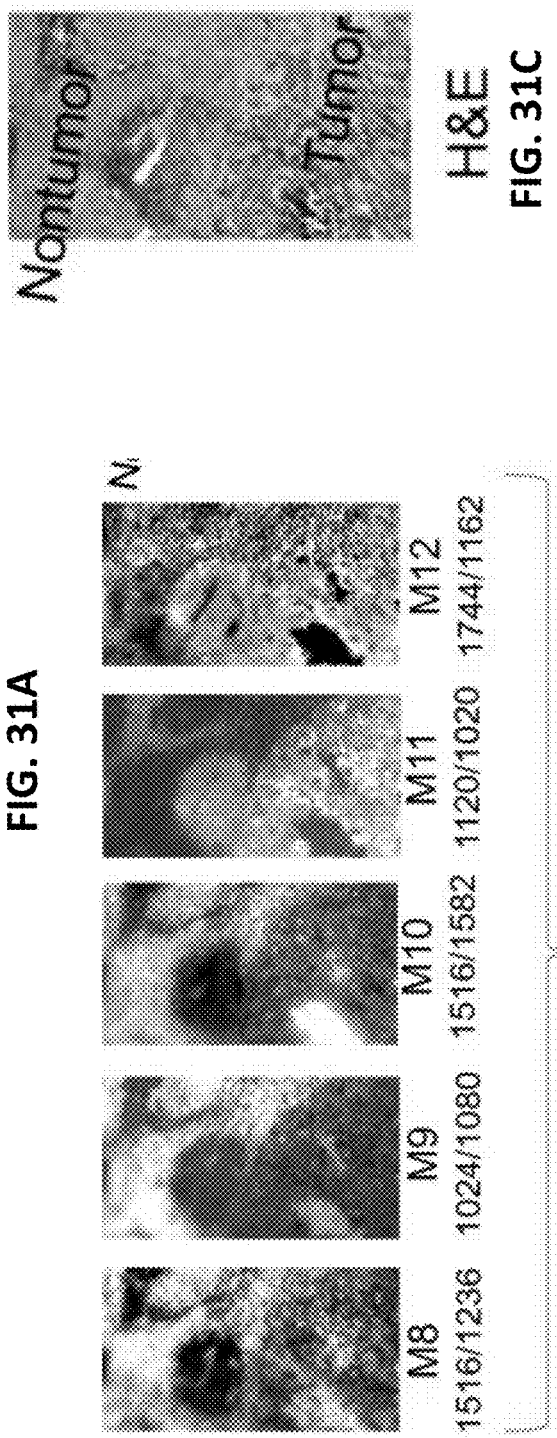
FIG. 31A H&E Metrics
FIG. 31B IR Metrics
FIG. 31C H&E

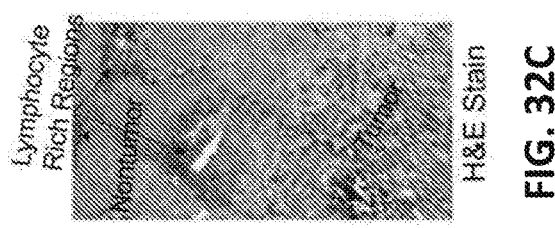
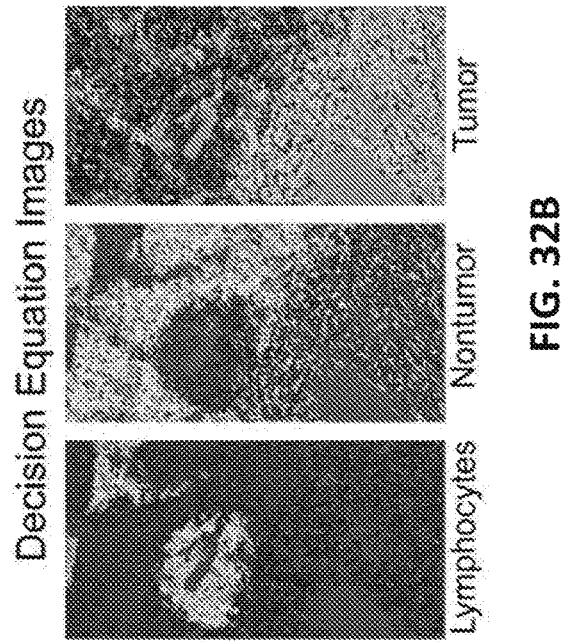
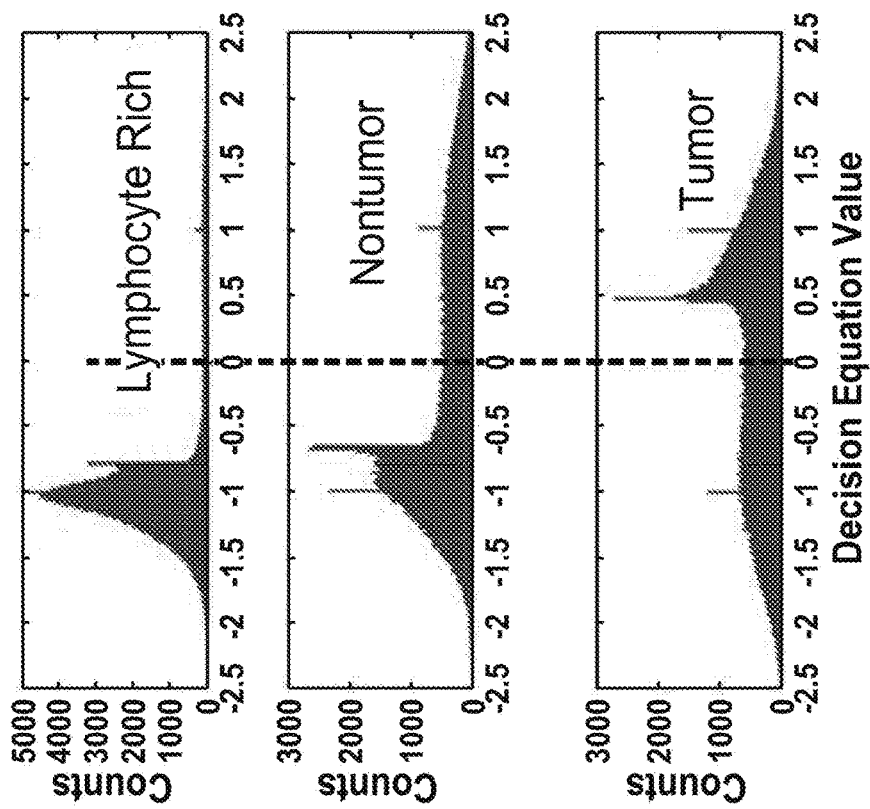
FIG. 32C
FIG. 32B
FIG. 32A

SYSTEM AND METHOD FOR THE DISCRIMINATION OF TISSUES USING A FAST INFRARED CANCER PROBE

CROSS-REFERENCE TO RELATED APPLICATION

This application is a national stage application filed under 35 U.S.C. § 371 of PCT/US2017/022670 filed Mar. 16, 2017, which claims priority to and benefit of U.S. Provisional Patent Application Ser. No. 62/309,116 filed Mar. 16, 2016, which is fully incorporated by reference and made a part hereof.

GOVERNMENT SUPPORT

This invention was made with government support under grant number CA167403 awarded by National Institutes of Health. The government has certain rights in the invention.

BACKGROUND

Infrared (IR) spectroscopy can be performed on a small amount of tissue and is sensitive to molecular-level biochemical changes. It is non-destructive, involving no labeling or staining. Many other techniques require the patient or resected tissues to be subjected to labeling by nanoparticles, drugs, antibiotics, fluorescent dyes, radioactivity, quantum dots, fixation, etc. IR spectroscopy has great potential to identify tumors and distinguish tumor types. With appropriate statistical training on tissues of interest, the above results can help to provide objective information to the pathologist, dermatologist, and oncologist, informing histopathological judgments.

An attenuated total reflection (ATR) probe is a probe that uses an internally reflecting beam of light inside a crystal producing an evanescent wave at the crystal's reflecting surface. The evanescent wave penetrates a wavelength or so (~10 μm) into the region outside of the crystal, but it is still collected with the reflected light at the probe's detector. An ATR probe records an IR spectrum of whatever is touched by the probe tip which in this case is tissue. There exist many commercial Fourier Transform IR Attenuated Total Reflection (FTIR-ATR) probes which are used with commercial FTIR spectrometers. However, existing probes are generally too slow for detecting cancer in surgery or a clinic setting, i.e. in-situ.

Dermatologists need early detection and diagnosis of skin cancer. This is primarily accomplished with skin biopsy and examination under a microscope by a pathologist. The prospect of simply touching an IR probe to questionable tissue while in a clinic or the doctor's office and receiving an answer about whether there is cancer and what type of cancer is extremely promising. Likewise, if cancer is to be excised or resected, surgeons need to know if they have removed all of a tumor, but current histopathological practices, such as hematoxylin and eosin stain (H&E) and other staining methods, can take days before there is feedback about this important issue. With an IR probe, the possibility arises that an assessment of the surgical margin can be made in the operating room by the surgeon as the tissue is removed. This would greatly aid in critical decisions about how much tissue to remove and whether the amount removed is sufficient. However, currently getting a good statistical assessment of a surgical margin in resected tissues by FTIR-ATR is still too slow to have practical use in vivo.

Recent technological advances in quantum cascade IR lasers (QCL) have made tunable mid-IR lasers cheaper and available for a wider range of applications. Unlike FTIR with glowbar sources in which an IR spectrum in its entirety is recorded simultaneously, a QCL is tuned to one wavelength at a time which has the advantage of not needing to measure every wavelength in the spectrum. This reduction in the number of wavelengths probed corresponds to an increase in how fast a laser-based probe works. A reduction in the number of IR metrics needed for discerning tumor (abnormal) from nontumor (normal) can further enhance the speed of the process.

Therefore, what is desired are systems and methods where tissue discrimination can be performed fast enough to be useful in the operating room or during a clinical evaluation.

SUMMARY

Disclosed herein is a method of discriminating tissue of a specimen. In one aspect, the method comprises performing infrared (IR) spectroscopy on a specimen using a probe such as an attenuated total reflection (ATR) probe or a fiber loop probe, wherein the IR spectroscopy is performed using a reduced set of IR wavelengths; obtaining an IR spectrum of the specimen from the probe; and evaluating the obtained IR spectrum using one or more metrics, wherein the one or more metrics determine normal tissue of the specimen from abnormal tissue of the specimen. The method may further comprise identifying the normal tissue of the specimen from the abnormal tissue of the specimen. In one aspect, the identifying may be used to provide an assessment of the surgical margin made in the operating room by a surgeon as the abnormal tissue is removed. In one aspect, determining normal tissue of the specimen from abnormal tissue of the specimen comprises determining non-cancerous regions of the specimen from cancerous regions of the specimen.

The method may comprise a reduced set of IR wavelengths comprising 10 or fewer wavelengths. In one aspect, the reduced set of IR wavelengths comprises six wavelengths. In other aspects, the reduced set of IR wavelengths comprises five, or fewer, wavelengths.

The one or more metrics used for evaluating the obtained IR spectrum may comprise evaluating the IR spectrum using one or more of ratios of peak absorbances, principal component scores, calibrant dot product scores, tissue scattering metrics, and baseline correction metrics. The specimen may comprise in vivo tissue, resected tissue or skin.

In various aspects, performing IR spectroscopy on the specimen is performed using an IR source comprising a quantum cascade IR laser (QCL).

Evaluating the obtained IR spectrum using one or more metrics and determining normal tissue of the specimen from abnormal tissue of the specimen may be performed in 1 minute or less. In one aspect, evaluating the obtained IR spectrum using one or more metrics and determining normal tissue of the specimen from abnormal tissue of the specimen may be performed in 1 second or less.

Also disclosed herein is a system for discriminating tissue of a specimen. One aspect of the system comprises an infrared (IR) source; a probe in communication with the IR source via a fiber optic cable, wherein the probe is used to obtain an IR spectrum of the specimen in response to a reduced set of IR wavelengths provided by the IR source; an IR detector, wherein the IR detector receives the IR spectrum from the probe via a fiber optic cable; and a computing device comprising a processor and a memory in communication with the processor, the memory comprising computer-executable instructions, wherein the computing device receives a signal representative of the detected IR spectrum from the IR detector and the computer-executable instructions cause the processor to evaluate the obtained IR spectrum using one or more metrics, wherein the one or more metrics discriminate normal tissue of the specimen from abnormal tissue of the specimen.

In one aspect, the IR source of the system comprises a quantum cascade IR laser (QCL) that is a tunable mid-infrared laser with a reduced set of selected IR wavelengths that have been optimized for detecting chemical and molecular signatures of tissue specific lesions to include, but not limited to, cancer, preneoplasia, intracellular accumulations (e.g. steatosis), inflammation, and wound healing.

In one aspect, the probe of the system comprises an attenuated total reflection (ATR) probe, which is used to perform IR spectroscopy on the specimen using the reduced set of IR wavelengths. In other aspects, the probe comprises a fiber loop probe.

In one aspect, the IR detector of the system comprises a thermal microbolometer array detector as available.

In one aspect, the computing device of the system executes computer-executable instructions stored in the memory that cause the processor to identifying the normal tissue of the specimen from the abnormal tissue of the specimen. In one aspect, the computing device displays the identified normal tissue of the specimen and/or the identified abnormal tissue of the specimen to a surgeon in an operating room, which is used to provide an assessment of the surgical margin made in the operating room by the surgeon as the abnormal tissue is removed.

Further disclosed herein is a non-transitory computer-readable medium comprising computer-executable code sections thereon for causing a computing device to perform the method of receiving an IR spectrum of a specimen from a probe such as an attenuated total reflection (ATR) probe or a fiber loop probe, wherein the probe has been used to perform infrared (IR) spectroscopy on the specimen using wherein the IR spectroscopy is performed using a reduced set of IR wavelengths; and evaluating the obtained IR spectrum using one or more metrics, wherein the one or more metrics determine normal tissue of the specimen from abnormal tissue of the specimen.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive, as claimed.

BRIEF DESCRIPTION OF THE DRAWINGS

The accompanying drawings, which are incorporated in and constitute a part of this specification, illustrate embodiments and together with the description, serve to explain the principles of the methods and systems. The patent or application file contains at least one drawing executed in color. Copies of this patent or patent application publication with color drawing(s) will be provided by the Office upon request and payment of the necessary fee:

FIG. 2 is a flowchart that illustrates an exemplary method of discriminating tissue of a specimen;

FIGS. 18A-18D illustrate projection histograms (FIGS. 18C and 18D) of t-values for each k-means cluster onto a hyperdimensional line between the centroids of tumor (red, #8) and nontumor (blue, #6) clusters;

FIG. 21A shows a plot of M3, ratio of absorption at 1030 to that at 1000 cm$^{-1}$, vs M1, ratio of absorption at 1516 and 1572 cm$^{-1}$, using blue/red for nontumor/tumor in 1st case and cyan/magenta for nontumor/tumor in the 2nd. An SVM maximum margin line is shown with a black trace and the support vectors are circled. FIG. 21B shows the perpendicular distance from the maximum margin line, i.e. the decision equation values, presented as a histogram. One point was misidentified, resulting in approximately 98% success;

FIGS. 22A and 22B illustrate histograms of decision equation values for two cases of colorectal cancer metastatic to the liver. FIG. 22A uses full IR spectrum with 451 wavelengths yielding an unoccupied hard SVM margin, i.e. the gap in the middle. At FIG. 22B, only 6 well-chosen wavelengths (all in the range of QCL 1, a single QCL laser) are used: absorbance at 1410, 1472, 1542, 1584, and 1614 cm$^{-1}$ is ratioed to that at 1510 cm$^{-1}$. Zero out of 57 are incorrectly predicted;

FIG. 26A-26C illustrate proof of concept probe experiment on a live SKH1 mouse with skin tumors. FIG. 26A illustrates a fiber loop probe attached to an FTIR spectrometer records an IR spectrum upon touching mouse skin for ~2.5 min per spectrum. FIG. 26B illustrates a total of 31 spectra were recorded both off (green) and on (red) tumors. FIG. 26C illustrate the average IR spectrum off minus 3 times the average spectrum on tumor shows wavelengths useful for cancer metrics;

FIGS. 27A and 27B illustrate a live SKH1 mouse with skin tumors labeled with capital letters (FIG. 27A). FIG. 27B illustrates a plot of metric M6 vs M3 using green (left of decision equation line) for nontumor and red (right of decision equation line) for tumor. The SVM support vectors are circled and the SVM separating hyperplane, where the decision equation is zero, is given with a black trace;

FIGS. 29A-29D show the number of wavelengths was varied by successively doubling the skipped wavelengths giving 271, 68, 17, and 5 wavelengths. Wrong predictions start between 9 and 5 wavelengths. FIG. 29E shows that by varying and optimizing the wavelengths, one can obtain zero wrong predictions with only 6 wavelengths (absorbance at 1488, 1521, 1585, 1593, and 1644 ratioed to that at 1530 cm$^{-1}$);

FIGS. 31A-31C illustrate H&E (FIG. 31A) and IR metrics (FIG. 31B) are represented as greyscale images for the identical piece of tissue. Comparison to the H&E stain (FIG. 31C) reveals the nontumor and tumor portions. These metrics were combined at input to perform k-means clustering and SVM analysis which correlates the morphology of H&E with the biomolecular chemistry of IR. The IR seems to be better at detecting tumor; and FIGS. 32A-32C illustrate nonlinear SVM decision equation histograms for the lymphocyte rich, nontumor, and tumor groups of colorectal cancer metastatic to the liver (FIG. 32A). FIG. 32B illustrate these results can also be presented as images showing that there is more information in the decision equation than just classification into the group when d>0. FIG. 32C illustrates an H&E image reference for the decision equation images.

DETAILED DESCRIPTION

Figure 1:
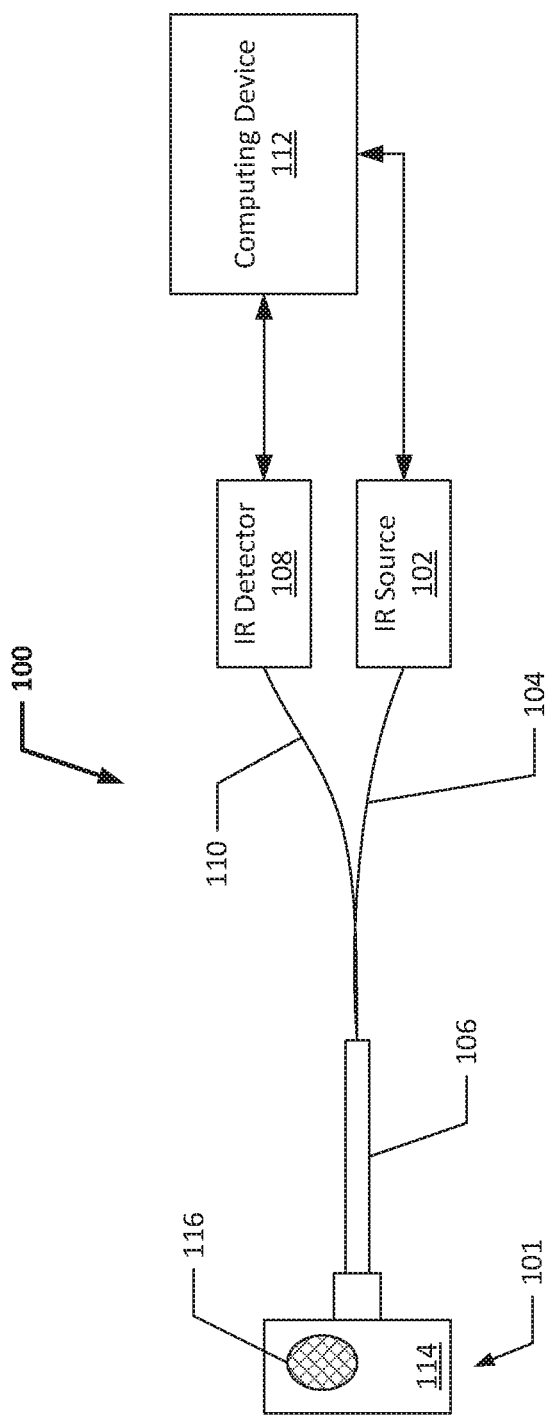
FIG. 1 illustrates an exemplary system for discriminating tissue of a specimen.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the Examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Described herein is an infrared attenuated total reflection (ATR) probe and discriminating software that can rapidly (on the timescale of seconds) discriminate abnormal tissue processes from those of normal tissue during: surgery, physical examination of in-situ lesions, and in the assessment of biopsy and resected tissue specimens. Non-limiting examples provided herein demonstrate discrimination of cancerous from noncancerous tissues. The discriminating software, i.e. the metrics, algorithms, calibrant spectra, and decision equations, provide a determination of whether the tissue is abnormal or normal using a minimum of infrared (IR) wavelengths in order to be measured rapidly. The disclosed probe embodiments can record IR metrics approximately 1000 times faster than current commercial instruments, i.e. on a timescale fast enough for clinical use. In one aspect, the probe comprises a tunable mid-infrared laser with a small set of selected wavelengths that have been optimized for detecting the chemical and molecular signatures of tissue specific lesions to include, but not limited to, cancer, preneoplasia, intracellular accumulations (e.g. steatosis), inflammation, and wound healing.

FIG. 1 illustrates an exemplary system 100 for discriminating tissue of a specimen 101. As shown in FIG. 1, the system 100 comprises an IR source 102. In one aspect, the IR source 102 comprises a quantum cascade IR laser (QCL) that is a tunable mid-infrared laser with a reduced set of selected IR wavelengths that have been optimized for detecting the chemical and molecular signatures of tissue specific lesions to include, but not limited to, cancer, preneoplasia, intracellular accumulations (e.g. steatosis), inflammation, and wound healing. For example, the IR source 102 may comprise an Ober Tuner™ QCL as available from Daylight Solutions (San Diego, Calif.) with a fiber optic mount. The selected IR wavelengths are provided to a specimen 101 via a fiber optic cable 104 and a probe 106. As used herein, "specimen" includes in vivo tissue, resected tissue, skin, and the like. In one aspect, the probe 106 comprises an attenuated total reflection (ATR) probe, which is used to perform IR spectroscopy on the specimen 101 using the reduced set of IR wavelength. For example, the probe 106 may be a ReactIR 15 probe as available from Mettler-Toledo (Beaumont Leys, Leicester). The probe 106 is also used to obtain an IR spectrum of the specimen 101 in response to the provided IR wavelengths. The IR spectrum is passed from the probe 106 to an IR detector 108 via a fiber optic cable 110. For example, the detector 108 may comprise a thermal microbolometer array detector as available from Sofradir EC, Inc. (Fairfield, N.J.). The detector 108 provides a signal representative of the detected IR spectrum to a computing device 112. The computing device evaluates the obtained IR spectrum using one or more metrics, wherein the one or more metrics discriminate normal tissue 114 of the specimen 101 from abnormal tissue 116 of the specimen 101. The IR source 102 may also be controlled by the computing device 112. The computing device comprises a processor. The processor may comprise a plurality of processors that are in communication with one another. As noted herein, processor refers to a physical hardware device that executes encoded instructions for performing functions on inputs and creating outputs. Exemplary processors for use in this disclosure are described herein in relation to FIG. 3.

It currently takes approximately 15 hours of FTIR imaging on tissue slices to record the data from one cancer patient. IR laser-based, hyperspectral imaging will improve this, but such devices will not soon be ready for in-situ use. However, an FTIR-ATR probe such as illustrated in FIG. 1 only takes a minute or so to record IR spectra. The replacement of the FTIR light source with a tunable midIR laser such as a QCL, reduces the data acquisition time to a few seconds. The system illustrated in FIG. 1 can make measurements and report a decision equation result in approximately one second. If measurements are made at six wavelengths and the FTIR-ATR probe can make measurements at 451 wavelengths in approximately 60 s, then the IR laser as illustrated in FIG. 1 is 75 times faster, thus requiring less than one second.

FIG. 2 is a flowchart that illustrates an exemplary method of discriminating tissue of a specimen. In FIG. 2, the exemplary method comprises 202, performing infrared (IR) spectroscopy on a specimen using an attenuated total reflection (ATR) probe, wherein the IR spectroscopy is performed using a reduced set of IR wavelengths. For example, the reduced set of IR wavelengths comprises 10 or fewer wavelengths. In one non-limiting example, the reduced set of IR wavelengths comprises six wavelengths. The specimen may comprise in vivo tissue, resected tissue, skin, and the like. In one aspect, IR spectroscopy on the specimen is performed on the specimen using, for example, an IR source comprising a quantum cascade IR laser (QCL). At 204, an IR spectrum of the specimen is obtained from the ATR probe. At 206, the obtained IR spectrum is evaluated using one or more metrics, wherein the one or more metrics determine normal tissue of the specimen from abnormal tissue of the specimen. In one aspect, determining normal tissue of the specimen from abnormal tissue of the specimen comprises determining non-cancerous regions of the specimen from cancerous regions of the specimen. In various aspects, evaluating the obtained IR spectrum using one or more metrics comprises evaluating the IR spectrum using one or more of ratios of peak absorbances, principal component scores, calibrant dot product scores, tissue scattering metrics, or baseline correction metrics. Evaluating the obtained IR spectrum using one or more metrics is performed using a computing device such as that shown and described herein. The method described in relation to FIG. 2 of evaluating the obtained IR spectrum using one or more metrics and determining normal tissue of the specimen from abnormal tissue of the specimen can be performed in one second or less.

The system has been described above as comprised of units. One skilled in the art will appreciate that this is a functional description and that the respective functions can be performed by software, hardware, or a combination of software and hardware. A unit can be software, hardware, or a combination of software and hardware. The units can comprise software for discriminating tissue of a specimen. In one exemplary aspect, the units can comprise a computing device that comprises a processor 321 as illustrated in FIG. 3 and described below.

Figure 3:
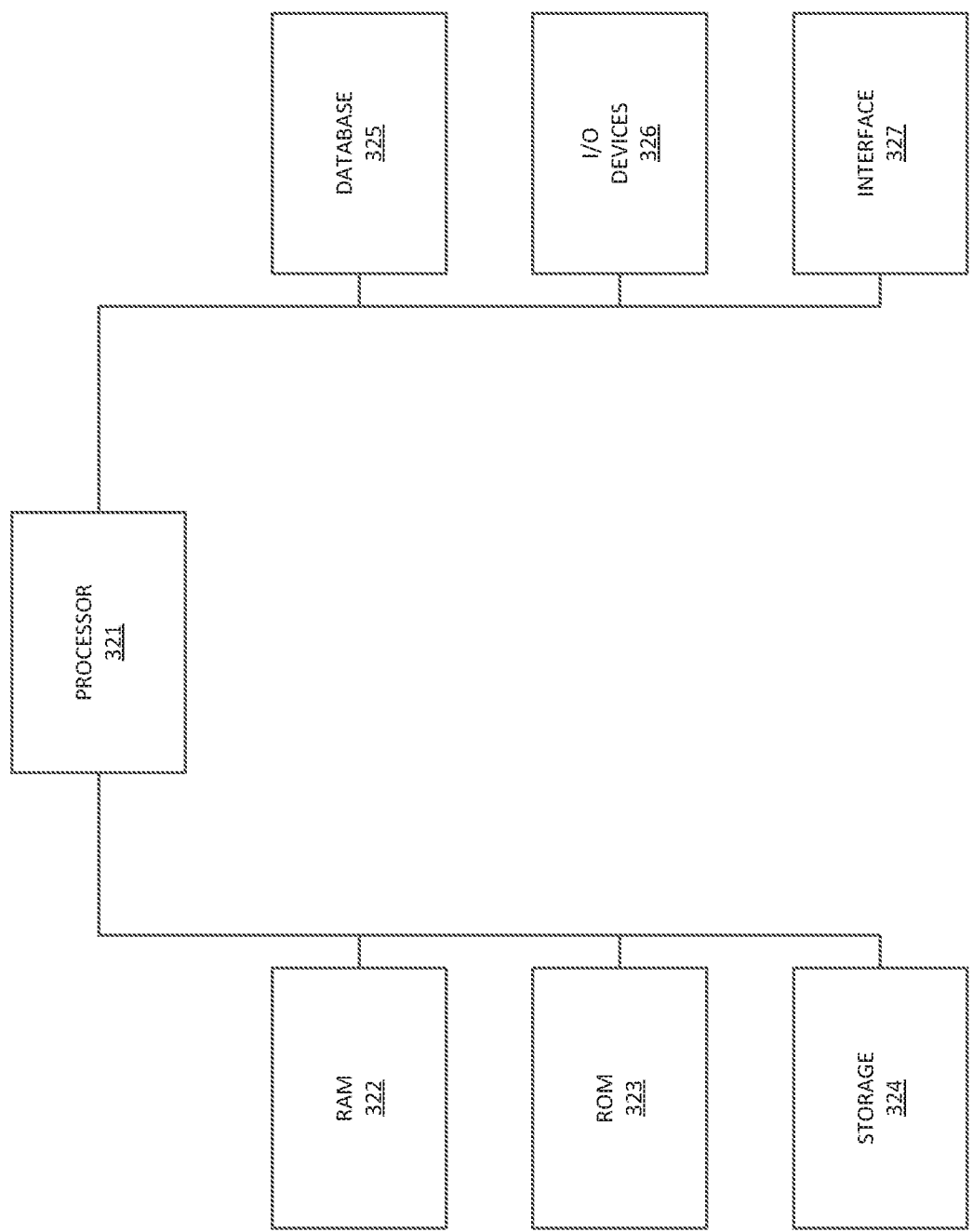
FIG. 3 illustrates an exemplary computer that can be used for discriminating tissue of a specimen.

FIG. 3 illustrates an exemplary computer that can be used for discriminating tissue of a specimen. As used herein, "computer" may include a plurality of computers. The computers may include one or more hardware components such as, for example, a processor 321, a random access memory (RAM) module 322, a read-only memory (ROM) module 323, a storage 324, a database 325, one or more input/output (I/O) devices 326, and an interface 327. Alternatively and/or additionally, the computer may include one or more software components such as, for example, a computer-readable medium including computer executable instructions for performing a method associated with the exemplary embodiments. It is contemplated that one or more of the hardware components listed above may be implemented using software. For example, storage 324 may include a software partition associated with one or more other hardware components. It is understood that the components listed above are exemplary only and not intended to be limiting.

Processor 321 may include one or more processors, each configured to execute instructions and process data to perform one or more functions associated with a computer for discriminating tissue of a specimen. Processor 321 may be communicatively coupled to RAM 322, ROM 323, storage 324, database 325, I/O devices 326, and interface 327. Processor 321 may be configured to execute sequences of computer program instructions to perform various processes. The computer program instructions may be loaded into RAM 322 for execution by processor 321.

RAM 322 and ROM 323 may each include one or more devices for storing information associated with operation of processor 321. For example, ROM 323 may include a memory device configured to access and store information associated with the computer, including information for identifying, initializing, and monitoring the operation of one or more components and subsystems. RAM 322 may include a memory device for storing data associated with one or more operations of processor 321. For example, ROM 323 may load instructions into RAM 322 for execution by processor 321.

Storage 324 may include any type of mass storage device configured to store information that processor 321 may need to perform processes consistent with the disclosed embodiments. For example, storage 324 may include one or more magnetic and/or optical disk devices, such as hard drives, CD-ROMs, DVD-ROMs, or any other type of mass media device.

Database 325 may include one or more software and/or hardware components that cooperate to store, organize, sort, filter, and/or arrange data used by the computer and/or processor 321. For example, database 325 may store the wavelengths used for performing infrared (IR) spectroscopy on a specimen using an attenuated total reflection (ATR) probe, wherein the IR spectroscopy is performed using a reduced set of IR wavelengths. The database 325 may also store the IR spectrum of the specimen is obtained from the ATR probe and the one or more metrics that are used to determine normal tissue of the specimen from abnormal tissue of the specimen. It is contemplated that database 325 may store additional and/or different information than that listed above.

I/O devices 326 may include one or more components configured to communicate information with a user associated with computer. For example, I/O devices may include a console with an integrated keyboard and mouse to allow a user to maintain a database of IR spectrums, metrics and the like. I/O devices 326 may also include a display including a graphical user interface (GUI) for outputting information on a monitor. I/O devices 326 may also include peripheral devices such as, for example, a printer for printing information associated with the computer, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 327 may include one or more components configured to transmit and receive data via a communication network, such as the Internet, a local area network, a workstation peer-to-peer network, a direct link network, a wireless network, or any other suitable communication platform. For example, interface 327 may include one or more modulators, demodulators, multiplexers, demultiplexers, network communication devices, wireless devices, antennas, modems, and any other type of device configured to enable data communication via a communication network.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures and other reaction ranges and conditions that can be used to optimize the product purity and yield obtained from the described process.

Example 1—Proof of Concept with Experimental FTIR-ATR Probe Data for Cancer

Infrared (IR) spectra were recorded by touching a diamond tip FTIR-ATR probe to liver tissues resected from patients with colorectal cancer metastatic to the liver, though probes having tips comprised of other materials are contemplated as being within the scope of this disclosure. A model based on the ratio of absorbances at selected IR wavelengths employed relative weightings that were optimized for separation of tumor and nontumor tissues. The model quantifies the contributions of each metric, enabling the performance of different metrics to be quantitatively compared. The model of this example also employs only 6 different wavelengths, so the prospect of even faster measurements arises by the measurement of absorption at just these wavelengths rather than wavelengths across the full IR spectral range.

Figure 4:
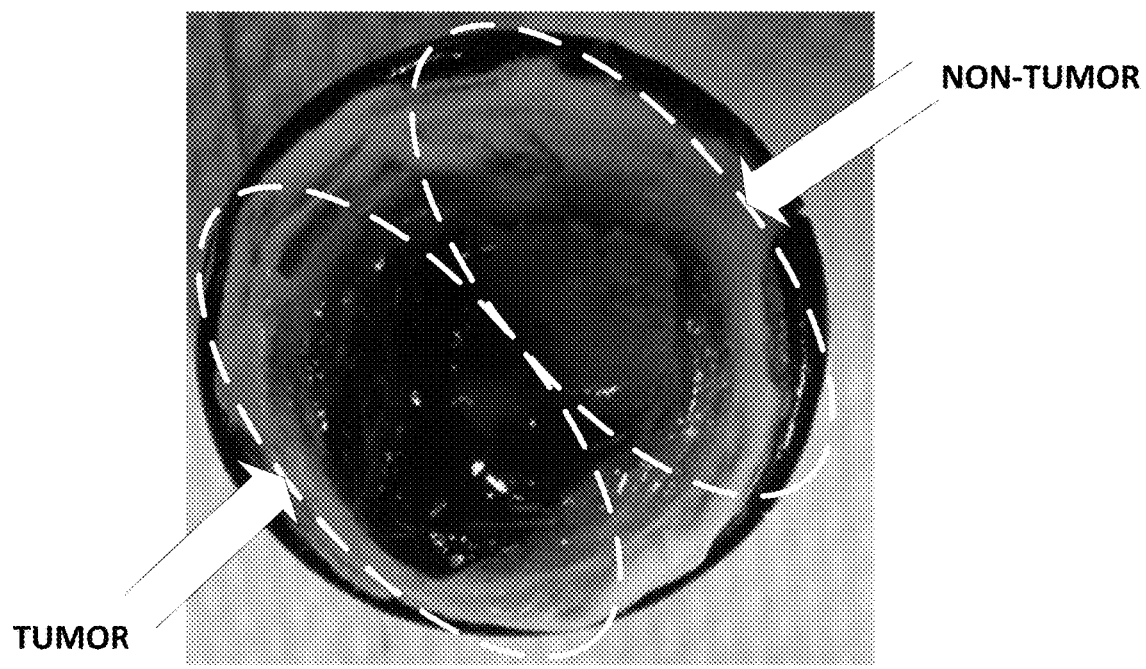
FIG. 4 shows a portion of excised liver tissue extending across a tumor (lighter color in the upper right portion)
Figure 5A:
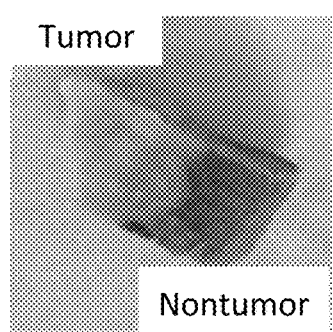
FIG. 5A is a photograph of a resected piece of liver tissue about 2.5 cm wide with nontumor portion in dark red at bottom right and tumor portion of lighter color at top left.
Figure 5B:
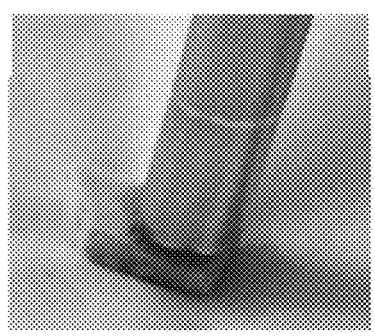
FIG. 5B is a photograph of an FTIR-ATR probe being pushed into the nontumor region.
Figure 5C:
FIG. 5C is a photograph showing the recording an IR spectra by holding the tissue against the slightly recessed diamond tip of the FTIR-ATR probe in different locations of the nontumor and tumor regions.
Figure 5D:
FIG. 5D is a photograph of a fiber loop probe being used to absorb an infrared absorption spectrum of a skin cancer specimen.
Figure 6:
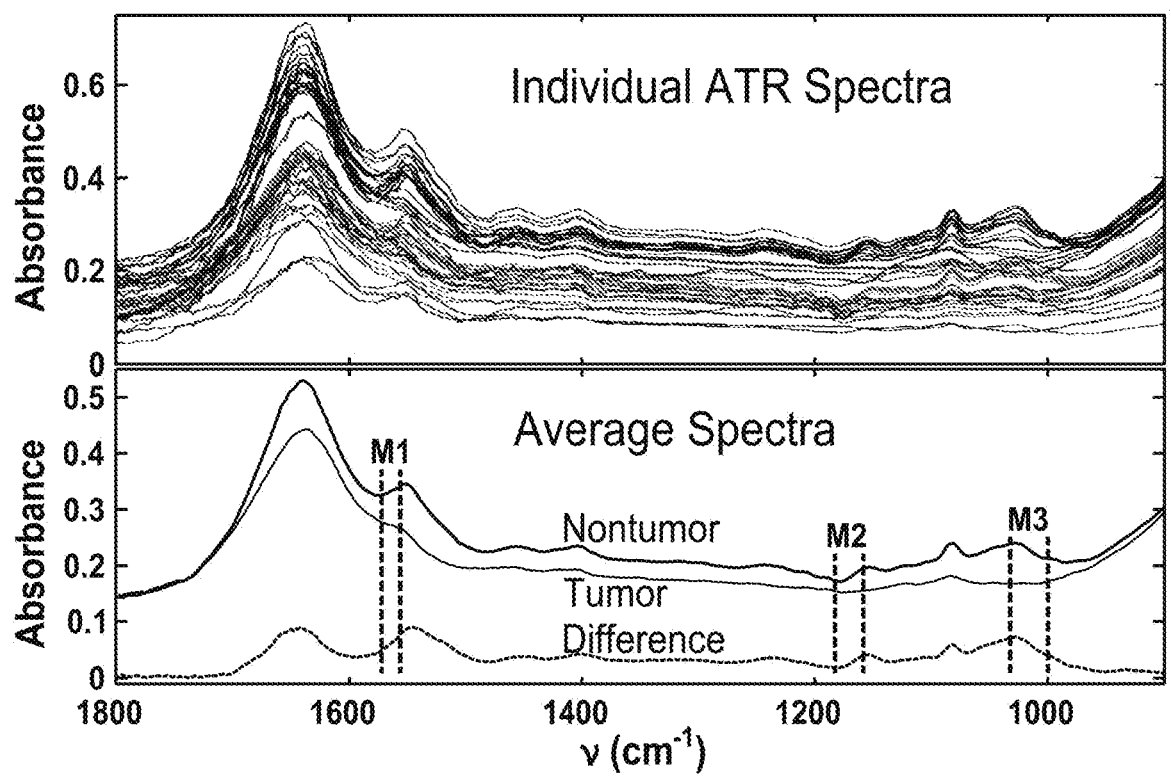
FIG. 6 (top panel) is an overlay of 57 individual ATR spectra with blue and cyan traces (generally the traces from the middle of the 57 traces toward the upper part of the panel) for nontumor and red and magenta traces (generally the traces from the middle of the 57 traces toward the bottom part of the upper panel) for tumor and FIG. 6 (bottom panel) is a plot that shows the average spectra of the nontumor (blue upper line) and tumor (red middle line) groups. The difference (green lower line) reveal wavelengths of potential interest for developing metrics, where "M1", "M2" and "M3" indicate the wavelength pairs of optimized metrics.

Portions of remnant liver tissue containing both cancer-bearing tissue and normal surrounding liver tissue were obtained from the Department of Pathology at The Ohio State University (Columbus, Ohio) at the time of the patient's planned surgical procedure. FIG. 4 shows a portion of excised liver tissue extending across a tumor (lighter color in the upper right portion). Tissue acquisition and utilization was approved by the Institutional Review Board (No. 2011C0085). Tissue samples were obtained from two patients both with colorectal cancer metastatic to the liver. Immediately after collection, the tissue specimens were snap frozen in liquid nitrogen (77 K) to preserve structural integrity for further analyses. Another sample from a second patient is pictured in FIG. 5a, where the tumor is lighter and lying at the top left of the image. A diamond tip FTIR-ATR probe (0.6 cm diameter and 150 cm length) working with a Mettler Toledo ReactIR 15 spectrometer is shown touching the tissue in FIG. 5b while recording an IR spectra. This specific probe has a recessed diamond tip for recording IR spectra of solutions and is less than ideal for tissue work. In spite of the physical constraints shown in FIG. 5c associated with pressing tissues onto the probe, the experiments worked very well. The FTIR used a liquid nitrogen-cooled MCT detector and IR spectra were recorded with 64 accumulations, from 900-1800 cm·1, with a resolution of 4 cm·1, and requiring approximately one minute per spectrum. The ATR probe system collected data in 1.86 cm·1 steps, so the spectral absorptions were linearly interpolated with a MATLAB® (R2013a, Math Works) 'interpl' function from 900 to 1800 cm·1 in steps of 2 cm·1 in order to better match and compare to other spectra. All individual FTIR-ATR spectra are plotted in the top panel of FIG. 6. A set of 19 spectra were collected on the nontumor (blue) and 18 on the tumor (red) of the first case, while 10 spectra were collected on the nontumor (cyan) and 10 spectra on the tumor (magenta) of the second case. Relative to traditional FTIR, this ATR data corresponds to a smaller spectral range of approximately 900-1700 cm·1 and there is a noticeable positive offset in absorbance. Also, the peak positions are slightly different than that from traditional FTIR because the penetration of the evanescent IR wave from the ATR tip into the tissue varies with wavelength. The largest peak is the amide I band (approximately 1656 cm·1) and the second largest is the amide II band (approximately 1554 cm-1), both which are dominated by protein in the samples. While the top panel of FIG. 6 shows large variations in the initial measurements, the bottom panel of FIG. 6 shows the averages of the tumor and nontumor spectra. Significant differences exist (shown in green) revealing that it is possible to discern metrics that distinguish tumors.

The process of discovering IR metrics started by collecting the individual nontumor spectra of both cases as rows in matrix X1 and the individual tumor spectra of both cases as rows in matrix X2. The average spectra of the tumor (red) and nontumor (blue) groups are shown in the bottom panel of FIG. 6. There is less IR intensity and less structure in the tumor group in general that reveals a lower concentration of biomolecules in general in this type of tumor. In spite of variations in the absorption offsets, the nontumor and tumor groups have similar average offsets. A difference (green) of average nontumor minus average tumor is shown in at the bottom panel of FIG. 6. There are maxima in the nontumor minus tumor difference at 1642 (amide I), 1546 (amide II), 1454, 1402, 1238, 1154, 1082, and 1028 (glycogen) cm$^{-1}$ and the search for metrics concentrated on these wavelengths. The metrics were scaled ratios of absorbance at selected wavelengths. Initially, while starting with 16 metrics based on ratios of absorbance at peak wavelengths selected from previous work, but this was reduced to the three most important metrics by a metric optimization (see below). The following discussion only uses the three best metrics, but any number can be employed. The three metrics found to be most effective in separating nontumor and tumor were:

$$[\alpha_1 I_{1556cm-1}/I_{1572cm-1}, \alpha_2 I_{1158cm-1}/I_{1182cm-1}, \alpha_3 I_{1032cm-1}/I_{1000cm-1}], \qquad (1)$$

where $\alpha_j$ values are relative weights for each metric (to be determined by fitting) and $I_{xcm-1}$ is the measured absorbance at a particular value x in cm$^{-1}$. Only the relative values of the $\alpha_j$ are important, so they were normalized such that $\Sigma_j \alpha_j^2 = 1$. The positions of the critical pairs of wavenumbers are labeled in the bottom panel of FIG. 6 with "M1", "M2", and "M3" for each metric. The values of the metrics for the nontumor spectra of both cases were collected as rows in matrix Xr1, i.e. the metrics of equation (1) are the elements of a row vector in Xr1. Likewise, the metrics for the individual tumor spectra of both cases were collected as rows of the matrix Xr2. The "r" in these names stands for "reduced" since the metric matrices have only three columns, while the raw data in the X1 and X2 matrices have 451 columns for each wavenumber step in the IR spectrum. [Note that this reduction from 451 to 6 wavelengths is one feature (but not the only feature) that enables the laser-based probe to be much faster.] The Xr1 (nontumor) and Xr2 (tumor) matrices have a column for each metric and row for each spectrum. Organization of the data in this form enables the optimization of both the relative weights ($\alpha_j$) and the best wavelengths (x in cm$^{-1}$) for a best set of metrics in the next section of this disclosure.

The figure of merit (FOM) for optimization involved comparing the average of the spreads of the nontumor ($\sigma_1$) and tumor ($\sigma_2$) metric values relative to the distance between the centroids ($D_{12}$) of the nontumor and tumor groups:

$$FOM = \frac{\sigma_1 + \sigma_2}{2D_{12}} = \frac{\sqrt{\left(\sum_{i_1=1}^{n_1}(d1_{i_1} - \overline{d1})^2\right)/(n_1 - 1)} + \sqrt{\left(\sum_{i_2=1}^{n_2}(d2_{i_2} - \overline{d2})^2\right)/(n_2 - 1)}}{2\sqrt{\sum_{j=1}^{m}(C2_j - C1_j)^2}}, \quad (2)$$

where $C1_j$ and $C2_j$ are the centroids or average metric values for the nontumor and tumor groups, respectively, and j=1, 2, ... m is an index for the metrics. The centroids are the averages down the columns of the Xr1 and Xr2 matrices. The sums are over the metrics. The $\overline{d1}$ and $\overline{d2}$ values are the averages of the Euclidean distances for the nontumor and tumor groups, respectively, from their corresponding centroid. They arise from the individual Euclidean distances $d1_{i_1}$ and $d2_{i_2}$, where i1=1, 2, ... $n_1$ for the nontumor spectra and i2=1, 2, ... $n_2$ for the tumor spectra. In terms of the metric matrices, the individual distances of the nontumor and tumor groups are:

$$d1_{i_1} = \sqrt{\sum_{j=1}^{m}(Xr1_{i_1,j} - C1_j)^2} \text{ and } d1_{i_1} = \sqrt{\sum_{j=1}^{m}(Xr2_{i_2,j} - C2_j)^2}, \quad (3)$$

where the sums are over the metrics. Given a choice of metrics such as equation (1), the best fit values are determined by minimizing FOM with respect to $\alpha_j$, the metric weights, which is the same as maximizing the separation between the tumor and nontumor groups. This was accomplished by writing a routine using the "fminsearch" function. A function was written and called by "fminsearch" which calculated the weighted metrics, centroids, distances, and FOM given an initial set of metric weights. The result was an optimized and normalized set of $\alpha_j$. Many other metrics were tried besides the ones reported in Table 1, below; however, the others had $\alpha_j$ values that were considerably smaller, so they were dropped from consideration. The wavenumber positions in the metric definitions were also varied manually, to minimize the FOM and maximize separation between tumor and nontumor. The resulting centroids and best fit metric weights are given in Table 1. Table 1 shows experimental average ratio of absorbances for nontumor and tumor groups (2nd and 3rd rows), optimized and normalized metric weights (4th row), and centroids based on weighted metrics (5th and 6th rows) associated with FOM=0.1488. The metrics are defined as $\alpha_j I_{x1cm-1}/I_{x2cm-1}$, where x1 and x2 are 1556 and 1572 for metric 1, 1158 and 1182 for metric 2, and 1032 and 1000 for metric 3, respectively, which were also optimized.

Comparison of the first two numbers in a column for a metric gives the experimental difference in the metric measurements between nontumor and tumor groups which amounts to 0.0929, 0.1342, and 0.1588 for M1, M2, and M3 respectively. However, the figure of merit necessarily accounts for the spread or errors in these numbers leading to the optimized weights given as the third number in each column. After the optimized weights are determined, the difference between the weighted centroids, i.e. the fourth and fifth number in each column, are 0.0702, 0.0316, and 0.0971 for M1, M2, and M3, respectively. Now the size reveals the relative importance. These results are relative and can be normalized yielding 35.3%, 15.9% and 48.8% as the importance of each metric for M1, M2, and M3, respectively. Metric M3 is the most important metric in this set which was culled from 16 initial metrics.

TABLE I

| Metric j | M1 | M2 | M3 |
| --- | --- | --- | --- |
| Exp. Avg. Nontumor Ratio of Absorbances | 1.0507 | 1.1402 | 1.1317 |
| Exp. Avg. Tumor Ratio of Absorbances | 0.9578 | 1.0060 | 0.9729 |
| Metric Weight, $\alpha_j$ | 0.7552 | 0.2253 | 0.6117 |
| Nontumor Centroid, $C1_j$ | 0.7935 | 0.2683 | 0.6923 |
| Tumor Centroid, $C2_j$ | 0.7233 | 0.2367 | 0.5952 |

Projection of Hyperdimensional Metrics.

Hyperdimensional data can be difficult to visualize. However in this case, the data came in the form of two groups, tumor and nontumor, so the hyperdimensional metric data was projected onto a line defined by the centroids of the nontumor ($C1_j$) and tumor ($C2_j$) groups. The projection yields a parameterized value or t value for the metrics of each individual spectrum. The t values for the nontumor ($t1_{i_1}$) and tumor groups ($t2_{i_2}$) are given by:

$$t1_{i_1} = \frac{\sum_{j=1}^{m}[(Xr1_{i_1} - C1_j)(C2_j - C1_j)]}{\sum_{j=1}^{m}(C2_j - C1_j)^2} \text{ and} \quad (4)$$

$$t2_{i_2} = \frac{\sum_{j=1}^{m}[(Xr2_{i_1} - C1_j)(C2_j - C1_j)]}{\sum_{j=1}^{m}(C2_j - C1_j)^2},$$

Figure 7:
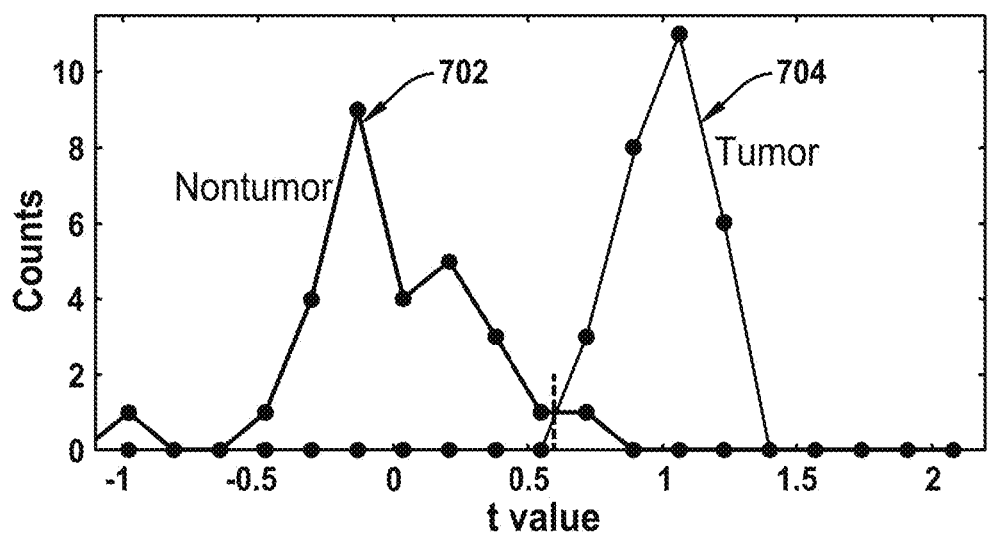
FIG. 7 is a histogram oft values from optimized metrics of individual nontumor (blue) 702 and tumor (red) 704 ATR spectra.

The average nontumor group metric has a projected t value of 0, while the average tumor group has a projected t value of 1. The occurrence oft values (a unitless quantity) is shown as a histogram in FIG. 7 using bins of 0.17. FIG. 7 is a histogram of t values from optimized metrics of individual nontumor (blue) 702 and tumor (red) 704 ATR spectra. Optimization with weighted metrics gives optimal separation of these distributions with a separating line at t=0.60. Nontumor results are shown in blue and the tumor results are shown in red. Using this method of optimized weights, only one nontumor score out of 57 total spectra falls under the tumor distribution, i.e. a success rate of approximately 98%.

The results in Table 1 can be used to predict whether any general ATR spectrum of liver tissue corresponds to tumor or nontumor. If one measures the ATR ratio of absorbances ($I_{x1cm-1}/I_{x2cm-1}$) at the pairs of wavenumbers specified by the x1 and x2 wavenumbers for each of the three metrics, then a nontumor/tumor prediction can be rendered using the results in Table 1. One multiplies each ratio of absorbances by the corresponding metric weight ($\alpha_1$) producing a three element row vector like $Xr1_{i1,j}$ (or $Xr2_{i2,j}$) of equation (4). The measured values of $Xr1_{i1,j}$ (or $Xr2_{i2,j}$) are combined with the $C2_j$ and $C1_j$ centroid values from Table 1 to determine a t value using equation (4). In this case, if t>0.60, then tumor has been detected and if t<0.60, then nontumor is detected. One should make as many measurements as time allows in order to get a good statistical assessment of a subject like a surgical margin.

Simple FTIR-ATR probe measurements requiring approximately one minute of data acquisition time each have been shown to reliably determine whether liver tissues contain tumors for two cases of colorectal cancer metastatic to the liver. A method was developed which involved weighting metrics based on ratios of absorbances at selected wavelengths. Three metrics were found to be efficient at distinguishing tumor and nontumor. The first metric measures the steepness of the high wavenumber side of the amide II band of protein backbones, i.e. changes in protein between nontumor and tumor regions are readily apparent. Since albumin is a dominant protein in normal liver and since it is an α-helix dominated structure, it is likely that cancerous transformation will on average reduce α-helix and increase other protein secondary structures such as β-sheet in liver tissues. The second and third metrics measure peaks at 1158 and 1032 cm$^{-1}$ which are reduced on average in the tumor spectra and may be related to polysaccharides like glycogen. One can assess their relative importance by calculating $C2_j-C1_j$ for each metric using the data in Table 1 which gives the relative importance as 0.36, 0.15, and 0.49 for metrics 1, 2, and 3, respectively. In these particular cases, the peak at 1032 cm$^{-1}$, which may have large contributions from glycogen, is quite important for discerning tumor. While the current model has been kept simple by only using three metrics, one can also use the method to weigh other metrics against the current set. New metrics can always be added to the model and their importance can be assessed. Since absorbances were only required at six different wavelengths with this particular model, there is the prospect of making much faster measurements with non-FTIR technologies, such as a with a tunable midIR laser, at only these six wavelengths. An increase in speed associated with direct measurements of the metrics rather than the whole spectra will render these methods useful in real-time during surgery or in a clinical setting.

IR Metrics.

Figure 8:
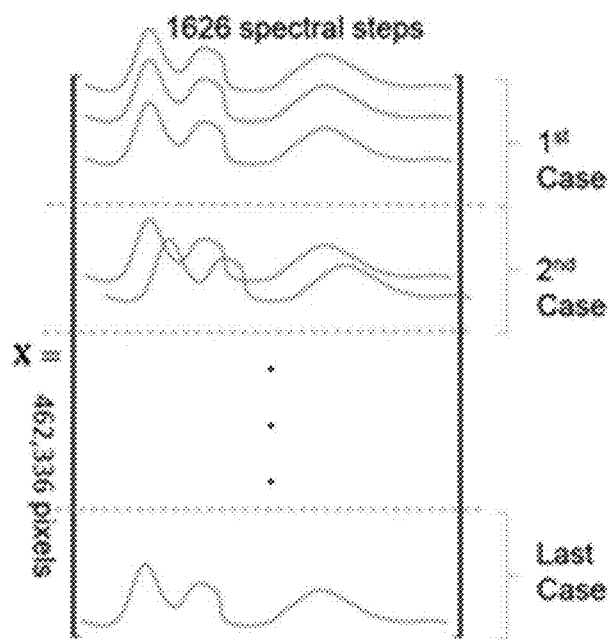
FIG. 8 illustrates an X matrix comprised of IR spectra arranged in rows.

There are many other metrics besides ratios of peak absorbances that can be used in practice to evaluate IR spectra of tissues including principal component scores, calibrant dot product scores, tissue scattering metrics, and baseline correction metrics. All of these metrics are extracted from matrix representations of the data, i.e. matrices are created in which each row contains an IR spectrum (either different spectral measurements with an IR probe or for each pixel in an IR imaging data set). We call this matrix the X matrix as shown in FIG. 8, which is comprised of IR spectra arranged in rows. We have written programs that include all five of the above mentioned types of metrics and can quantify the importance of different metrics even when they are of different types with our metric optimization method described herein.

Peak Ratio Metrics.

Figure 9:
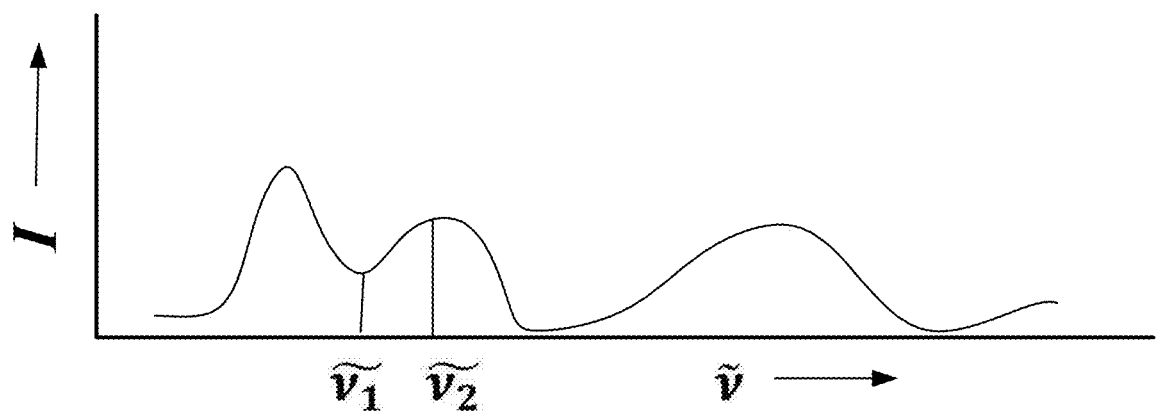
FIG. 9 shows peak ratio metrics, i.e. $I_{\bar{v}_2}/I_{\bar{v}_1}$.

A peak ratio metric is the absorbance at one wavelength divided by the absorbance at another wavelength as shown in FIG. 9, which shows peak ratio metrics, i.e. $I_{\tilde{v}_2}/I_{\tilde{v}_1}$. In terms of the X matrix, this is $X_{i,j2}/X_{i,j1}$ for pixel i at wavelengths j2 and j1. Peak ratio metrics do not vary with sample thickness, require a small number of wavelengths, and can be chosen at wavelengths for pairs of biomolecules of interest.

Principal Component Scores.

Figure 10:
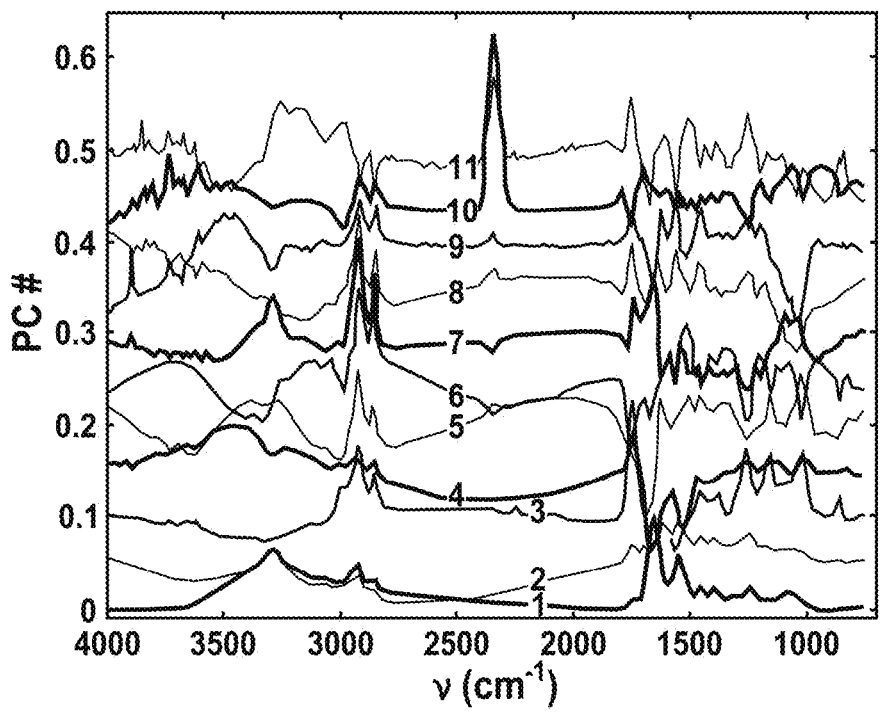
FIG. 10 illustrates the first 11 principal components of an X matrix comprised of 462,336 IR spectra of colorectal cancer metastatic to the liver.

Principal component analysis (PCA) finds the eigenvectors (W) of the matrix $X^T \cdot X$, i.e. $W=\text{eigs}(X^T \cdot X)$. The eigenvectors in this case are an orthogonal set of vectors that look like IR spectra and are ordered by their contributions to variance. Libraries or X matrices are constructed for tissues of interest and FIG. 10 shows the principal components of a library for colorectal cancer metastatic to the liver. FIG. 10 illustrates the first 11 principal components of an X matrix consisting of 462,336 IR spectra of colorectal cancer metastatic to the liver, i.e. the CCML Library (described later). One can obtain a score ($S_{PC}$) or metric for each principal component for each IR spectrum in the X matrix with $S_{PC}=X \cdot W$. Since this type of principal component score involves all of the wavelengths, these scores are not the most useful for this project, but they guide the construction of useful metrics. This metric is a purely mathematical investigation of changes from the average.

Calibrant Dot Product Scores.

Figure 11:
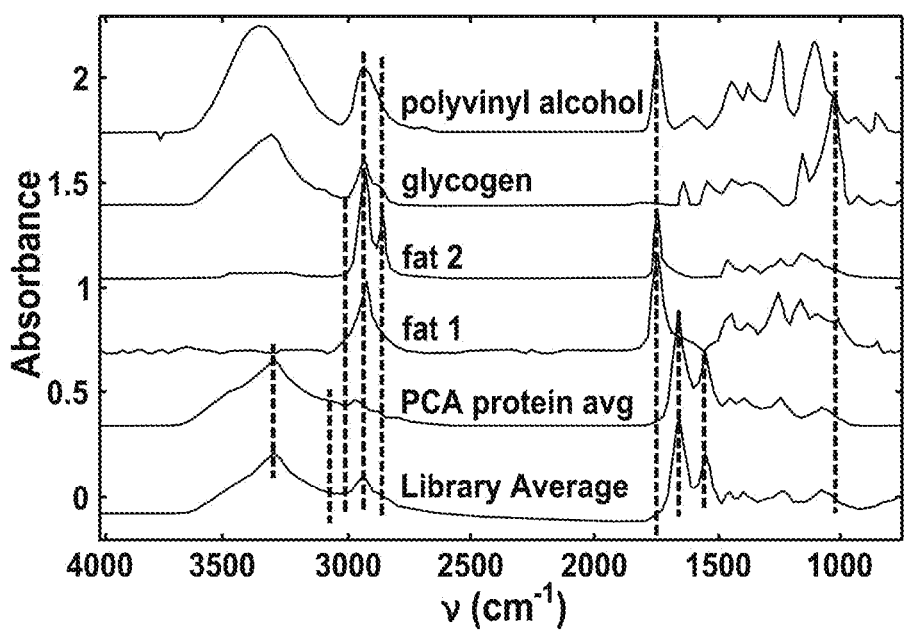
FIG. 11 illustrates an average IR spectrum of the CCML Library compared to the IR spectra of average liver protein, two types of ester-linked fat, glycogen, and polyvinyl alcohol that were isolated in previous studies.

Many biomolecules are known to be in tissues including many types of proteins, phospholipids, triglycerides, and polysaccharides. If a matrix C is constructed with rows containing the IR spectra of calibrant molecules, then scores ($S_{cal}$) or metrics of each IR spectrum in the X matrix are obtained with $S_{cal}=X \cdot C^T$. In practice, it is useful to normalize all IR spectra before calculating these scores. Calibrant IR spectra useful for liver tissue are shown in FIG. 11. FIG. 11 illustrates an average IR spectrum of the CCML Library compared to the IR spectra of average liver protein, two types of ester-linked fat, glycogen, and polyvinyl alcohol that were isolated in previous studies. Dotted indicate that are examined to identify these types of biomolecules.

Baseline Correction Metrics.

Figure 12:
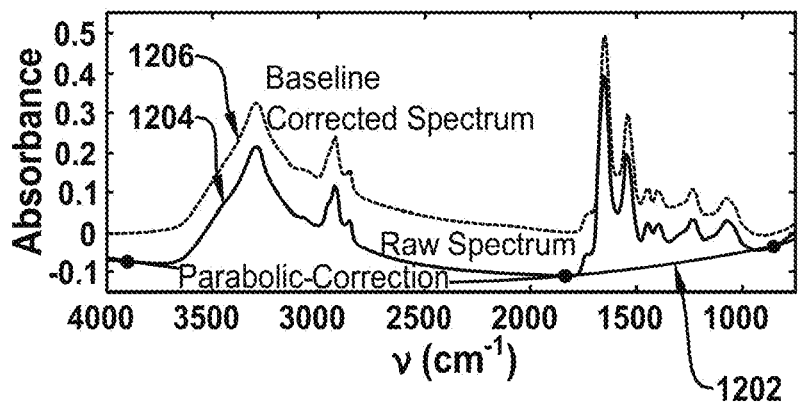
FIG. 12 illustrates that the three point parabolic correction of baseline (green bottom line) 1202 is subtracted from an IR spectrum (blue middle line) 1204 to yield a baseline corrected spectrum (red upper line) 1206.

The great abundance of IR work on tissues concerns absorption, but it turns out that tissues have very important scattering contributions because cells have changes in index of refraction associated with structures whose size matches the wavelength of probing IR light (approximately 2-20 μm). Scattering is typically ignored by a flattening of the baseline. One simple way to flatten the baseline of an IR spectrum is to pick three points that are isolated from the fundamental vibrations, for instance in this example we take the absorptions at 800, 1800, and 3900 cm$^{-1}$. These three points determine exactly the three unknowns (A, B, C) in a parabolic equation, $\text{Abs}=A\tilde{v}^2+B\tilde{v}+C$, whose values are in turn used to determine a more physically meaningful form, $\text{Abs}=\alpha(\tilde{v}-\beta)^2+\gamma$, where $\alpha=A$ (curvature), $\beta=-B/(2A)$ (position of the minimum), and $\gamma=C-B^2/(4A)$ (absorbance offset at minimum) as illustrated in FIG. 12. FIG. 12 illustrates that the three point parabolic correction of baseline (green) 1202 is subtracted for an IR raw spectrum (blue) 1204 to yield a baseline corrected spectrum (red) 1206. Instead of throwing away the baseline correction results, we can use them as metrics. Given the α, β, γ metrics, the parabolic baseline is subtracted from each IR spectrum in the X matrix yielding a baseline-corrected X matrix. We calculate one further metric that is the norm of each baseline corrected IR spectrum. This final metric, the norm of baseline corrected tissue spectra, provides a single number that quantifies the total amount of biomolecules in the tissue. It turns out to be very important in both distinguishing cancer and in distinguishing cell structures.

Metric Examples

Software has been developed that calculates all of the above types of metrics, then the user selects the metrics for comparison by optimization using weighted metrics. The following sections show some results of this metric work. There is an example using FTIR-ATR probe data and there are some examples with a library of full range IR spectra of colorectal cancer metastatic to the liver.

Calibrant Scores with FTIR-ATR Probe Data.

Figure 13:
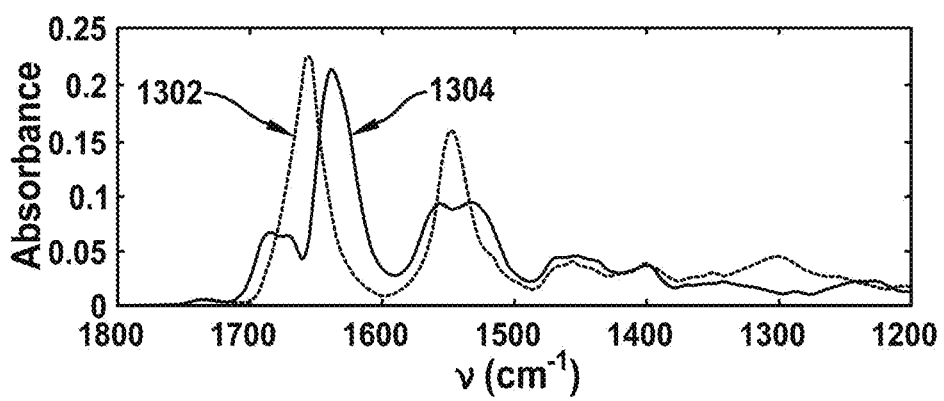
FIG. 13 illustrates that the IR spectra of α-helix 1302 and β-sheet 1304 extracted from a library of protein IR spectra are used as calibrants.
Figure 14:
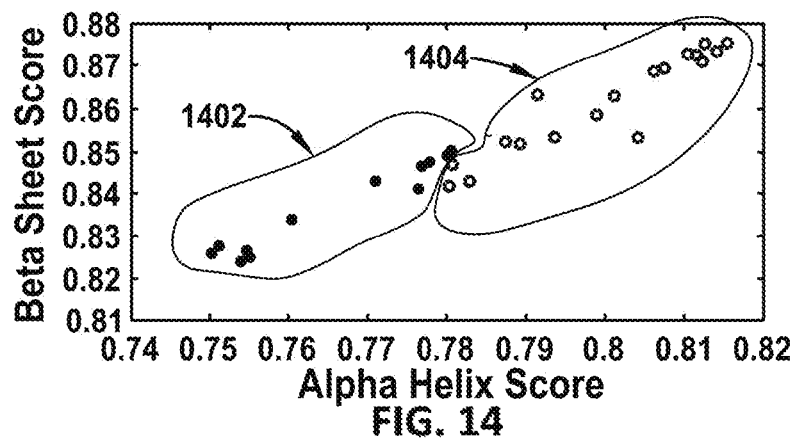
FIG. 14 illustrates FTIR-ATR spectra scores for β-sheet vs α-helix from the tissue shown in FIG. 4.

A recently published a paper [J. V. Coe, S. V. Nystrom, Z. Chen, R. Li, D. Verreault, C. L. Hitchcock, E. W. Martin Jr., and H. C. Allen, "Extracting Infrared Spectra of Protein Secondary Structures using a Library of Protein Spectra and the Ramachandran Plot", J. Phys. Chem B, 119:41 13079-13092 (2015)], incorporated by reference, described extracting the IR spectra of pure α-helix and β-sheet from a library of protein IR spectra as shown in FIG. 13. FIG. 13 illustrates that the IR spectra of α-helix (red) 1302 and β-sheet (green) 1304 extracted from a library of protein IR spectra are used as calibrants. The α-helix and β-sheet secondary protein structures are the most common ones and their IR spectra are very different. Since normal liver is ~80% albumin protein which is dominated by α-helix, the transformation of normal liver to tumor will produce a reduction in α-helix and an increase in β-sheet structures. A plot of the β-sheet vs α-helix and calibrant scores using normalized FTIR-ATR probe spectra from the tissue in FIG. 4 is shown in FIG. 14. FIG. 14 illustrates FTIR-ATR spectra scores for β-sheet vs α-helix from the tissue shown in FIG. 4. The results show complete separation of tumor (red) 1402 and nontumor (green) 1404 groups. Clearly other metrics based on biomolecular understanding are also valuable for distinguishing tumor and nontumor tissues.

Figure 15:
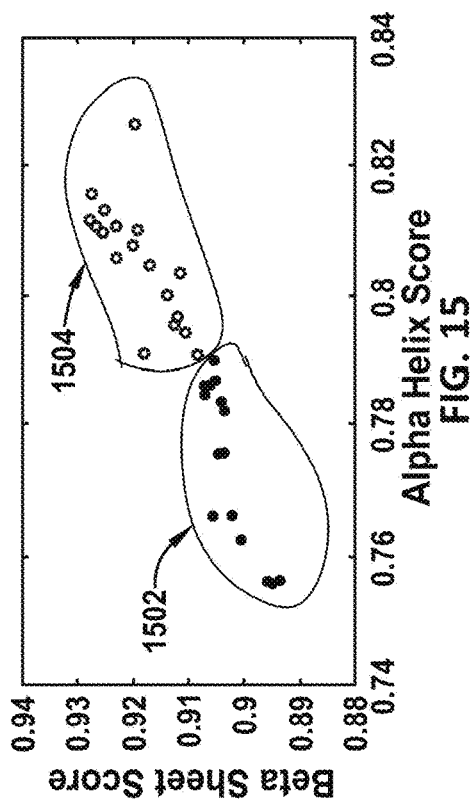
FIG. 15 illustrates β-sheet vs α-helix scores using data from 1500-1700 $cm^{-1}$ in 16 $cm^{-1}$ steps, i.e. only 13 wavelengths.
Figures 16A, 16B, 16C, 16D, 16E, 16F, 16G, 16H, 16I:
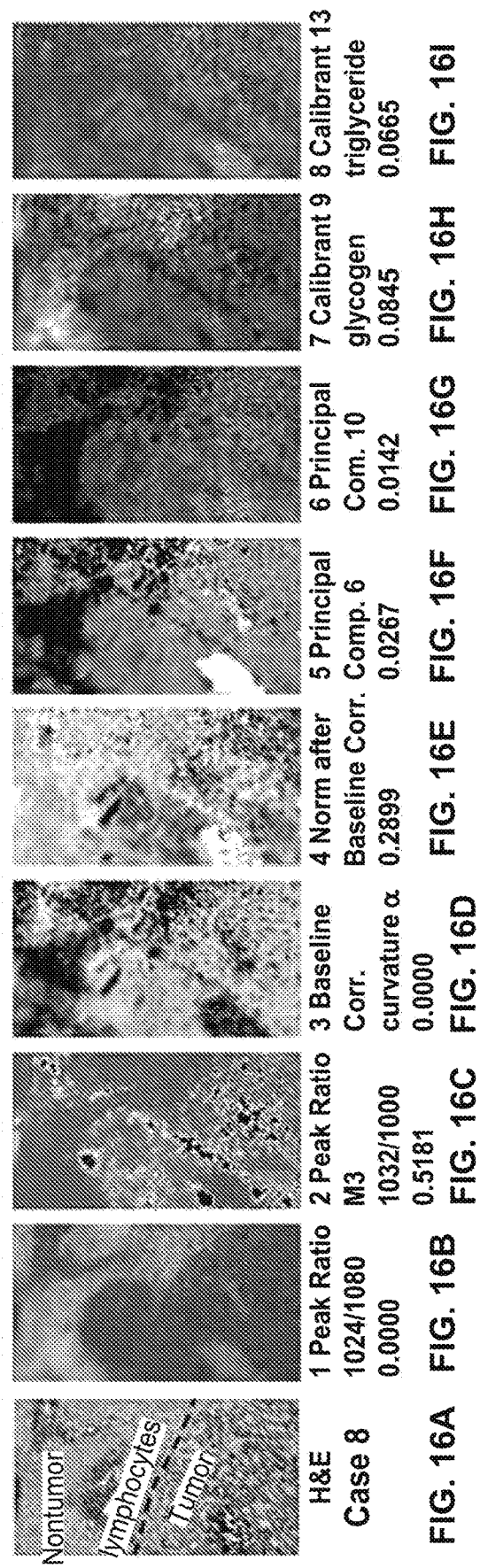
FIGS. 16A-16I illustrate greyscale images of different IR Metrics for comparison with an H&E stain (left, FIG. 16A) showing the tumor and nontumor regions.

While these are good metrics and they lead to new biomolecular understanding, they each involve 301 wavelengths and so are not appropriate for use with a Fast IR Probe. By limiting the range to between 1500 and 1700 cm$^{-1}$ and using only results spaced by 16 cm$^{-1}$ through this range, the set is reduced to just 13 wavelengths. The reduction in wavelengths still exhibits separation of tumor 1502 and nontumor tissue 1504 as shown in FIG. 15, i.e. measurements could be made 23 times faster, reducing one minute of acquisition time to just a few seconds. FIG. 15 illustrates β-sheet vs α-helix scores using data from 1500-1700 cm$^{-1}$ in 16 cm$^{-1}$ steps, i.e. only 13 wavelengths. Also, the laser system can make a comparable measurement faster, so it becomes possible to make metric measurements on the timescale of a second or so. Again, this makes its use in the operating room feasible, and in a clinic, convenient.

Colorectal Cancer Metastatic to the Liver Library with FTIR Imaging Data.

A unique library of IR imaging spectra for Colorectal Cancer Metastatic to the Liver (CCML Library) has been created by Professors Heather Allen and James Coe, in collaboration with several pathologists, Charles L. Hitchcock MD PhD and Dr. Tatiana Oberyszyn, and a team of surgical oncologists headed by Edward Martin, Jr. MD from The James, The Ohio State University Comprehensive Cancer Center. The liver is one of the most common sites for metastatic cancers. The library consists of 462,336 IR spectra from eight imaging experiments with 7 different patients. The tissues were collected with permission from patients having liver tumor resections (IRB #2011C0085, reapproved Aug. 21, 2014). The library is unique because the tissues are snap frozen and prepared for the IR microscope without the standard fixation (neutral buffered formalin solution, then dehydration with a sequence of graded ethanols, xylene, and finally paraffin). By only snap freezing, the natural fats are retained in the tissues, and thus denaturation of the proteins is significantly lessened. The IR imaging spectra have a 750-4000 cm$^{-1}$ range, a spectral resolution of 4 cm$^{-1}$, a spatial resolution of approximately six μm, and require about 15 hours of scanning to cover a 2 mm by 2 mm area of a tissue slice. The purpose of this library is to enable data mining for the development of the best IR metrics. The first 11 principal components of the CCML library were already displayed in FIG. 10.

Comparing Different Metrics with CCML Library.

An example of the quantitative comparison used eight metrics chosen from the different types: 1) peak ratio at 1024 and 1080 cm$^{-1}$, 2) peak ratio at 1032 and 1000 cm$^{-1}$ which is M3, the best from the ATR-FTIR study described above, 3) the baseline correction curvature, 4) the norm after baseline correction, 5) principal component #6, 6) principle component #10, 7) the calibrant glycogen, and 8) the calibrant triglyceride. Previously, the probe experiments were performed on either a tumor or nontumor region; however, this is not known in advance in FTIR imaging microscope work. This process proceeds with a 25 cluster k-means cluster analysis on the whole CCML Library, which identifies each image pixel with one of 25 clusters along and then allows calculation of each cluster's IR spectrum. Several clusters were chosen and used to construct an X1 matrix for nontumor and several other cluster groups were used to construct an X2 matrix for tumor. These are subsets of the X matrix. The weights of each of the eight metrics were optimized for separation of tumor and nontumor in this example. It should be understood that the results pertain to the specific choice of clusters groups identified as tumor and nontumor. If one uses a different choice, one obtains different results. The scores of each metric were plotted as greyscale images for comparison to an H&E stain for a particular case (Case 8) in FIG. 16. FIGS. 16A-16I illustrate greyscale images of different IR Metrics for comparison with an H&E stain (left, FIG. 16A) showing the tumor and nontumor regions. Notice how different the images are for each metric. The importance of each metric expressed as a fraction is given at the bottom for each metric based on an optimization with weighted metrics. The metric optimization programs were run producing a quantitative comparison of the utility of these different types of metrics for the separation of tumor and nontumor as displayed in Table 2, below. Some of the fitted weights go to zero and they can be ignored. Others are negative which would work against the ones with positive weights in the absence of weights. The various types of metrics have been put on a common scale for quantitative comparison even though they are of very different types, such as principal component score versus peak ratios.

TABLE 2

Results of optimization with eight weighted metrics using the CCML Library

| Metric j | Importance | $\alpha_j$ Weight | $C1_j$, Nontumor Weighted Centroid | $C2_j$, Tumor Weighted Centroid | Nontumor Measured | Tumor Measured |
|---|---|---|---|---|---|---|
| 1 peak ratio 1024/1080 | 0.0000 | 0.0000 | 0.0000 | 0.0000 | 0.7576 | 0.3718 |
| 2 peak ratio 1032/1000 | 0.5181 | 0.0723 | 0.1962 | 0.3541 | 2.7147 | 4.8987 |
| 3 BC curvature | 0.0000 | −0.4355 | 0.0000 | 0.0000 | 0.0000 | 0.0000 |
| 4 norm after BC | 0.2899 | 0.0510 | 0.3862 | 0.2979 | 7.5734 | 5.8413 |
| 5 PC #6 | 0.0267 | 0.0655 | −0.0058 | 0.0023 | −0.0883 | 0.0358 |
| 6 PC #10 | 0.0142 | 0.1118 | −0.0046 | −0.0003 | −0.0410 | −0.0023 |
| 7 calibrant glycogen | 0.0845 | −0.8389 | −0.5127 | −0.4869 | 0.6112 | 0.5805 |
| 8 calibrant triglyceride | 0.0665 | 0.2863 | 0.1279 | 0.1076 | 0.4467 | 0.3760 |

Note that these calculations pertain to whole CCML Library even though images are shown from only one of the cases.

Beating the Curse of Dimensionality.

Figure 17:
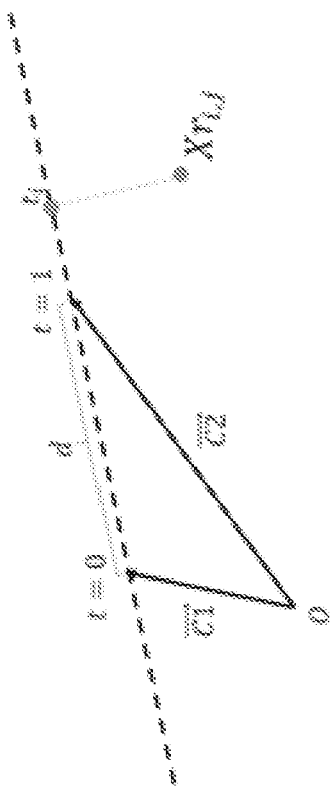
FIG. 17 illustrates the projection of metric scores ($Xr_{i,j}$) onto a parameterized line between the centroids of two chosen clusters ($C1_j$ and $C2_j$); each k-means cluster produces a distribution of t values which can be plotted on the same histogram plot.

The use of a large number of metrics helps with subtle discriminations between groups, but imposes great difficulty in visualization of the hyperdimensional results. The equations for projection of hyperdimensional metrics onto a line between the centroids of two chosen clusters were given above. FIG. 17 schematically shows how the t-value projection works. FIG. 17 illustrates the projection of metric scores ($Xr_{i,j}$) onto a parameterized line between the centroids of two chosen clusters ($C1_j$ and $C2_j$). Each k-means cluster produces a distribution of t values which can be plotted on the same histogram plot.

Figures 18A, 18B:
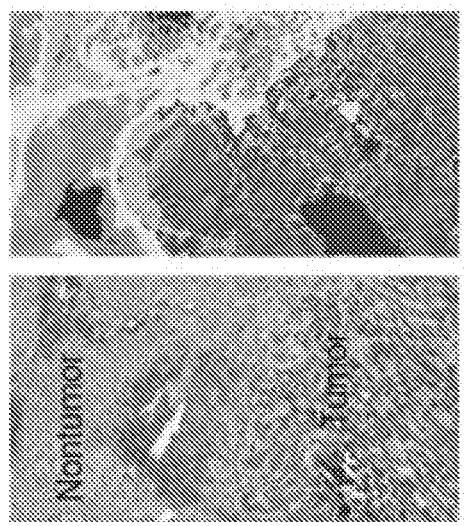

Using the same case as with FIG. 16 (Case 8), a 15 cluster k-means cluster analysis, and 5 peak ratio metrics including 1744/1244, 2924/1544, 1016/1080, 1744/1162, and 1080/3290 (the ratios of absorbance at the specified numbers as wavenumbers), the results shown in FIG. 18 are obtained, which are color coded. A tumor is shown in FIG. 18A. FIG. 18B shows tumor groups were colored with hot colors and nontumor groups were colored with cool colors. FIG. 18C illustrates projection histograms (right) of t-values for each k-means cluster onto a hyperdimensional line between the centroids of tumor (red, #8) and nontumor (blue, #6) clusters. The coloring of clusters in the k-means image ($2^{nd}$ image from left) corresponds to the coloring used for clusters in the projection histograms. The projections are largely Gaussians of a single color. Note in FIG. 18D the large separation of the #8 and #6 clusters. The t-value histograms have colors that correspond to the k-mean cluster image (2nd from left) that can be compared to the H&E stain (left). This work shows that t-value projections can help to solve a well-known problem with k-means clustering of not knowing the value of k, the number of clusters. One has enough clusters when the projections appear as well-behaved Gaussian distributions. Too many clusters leads to Gaussians with more than one color and too few leads to Gaussians with multiple colors. The software provides the IR spectra of each of the k-means clusters which can then be used to define IR metrics for separating the groups of interest. These results also reinforce the notion that tissue is very inhomogeneous. There are many types of tumor groups and many types of nontumor groups.

Metrics Across Individuals.

Figure 19:
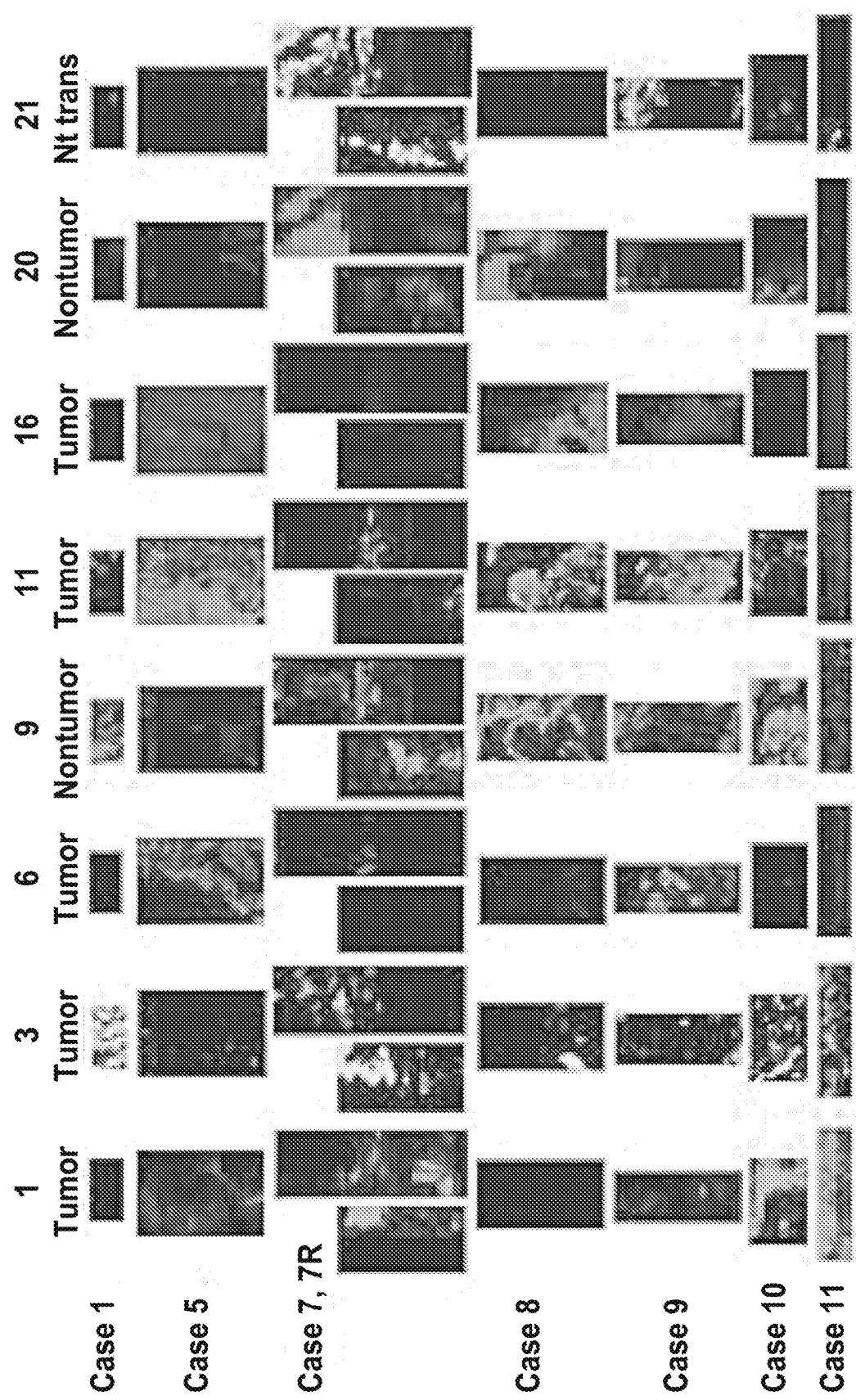
FIG. 19 illustrates preliminary k-means cluster analysis of the CCML Library using 25 clusters and 5 IR metrics from FIG. 7.
Figure 20B:
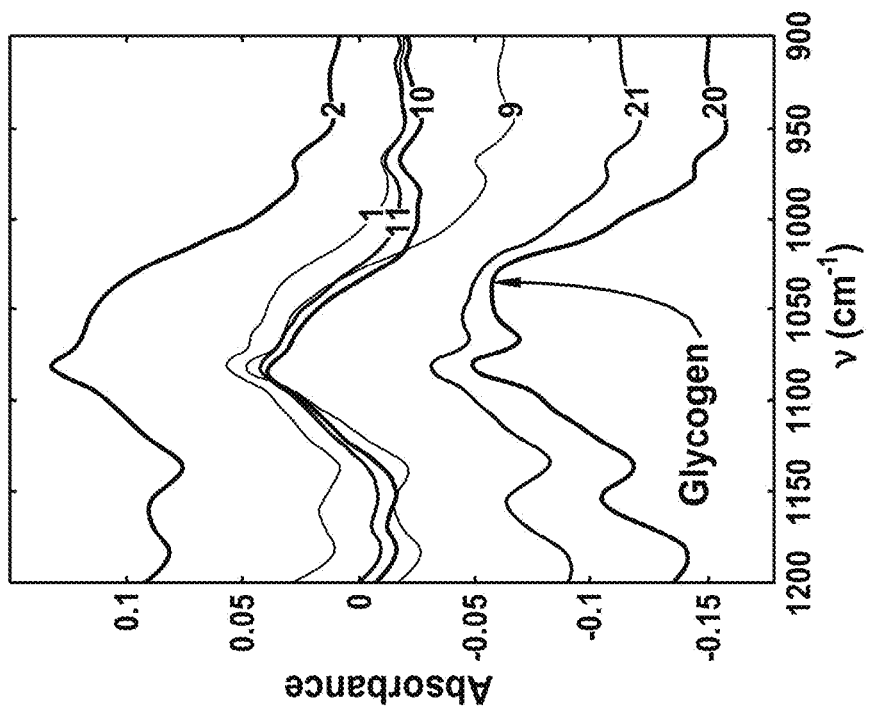
FIGS. 20A and 20B illustrate that IR spectra of k-means cluster groups which are common to all cases in the CCML Library with colors that match FIG. 12 and cluster numbers
Figure 20A:
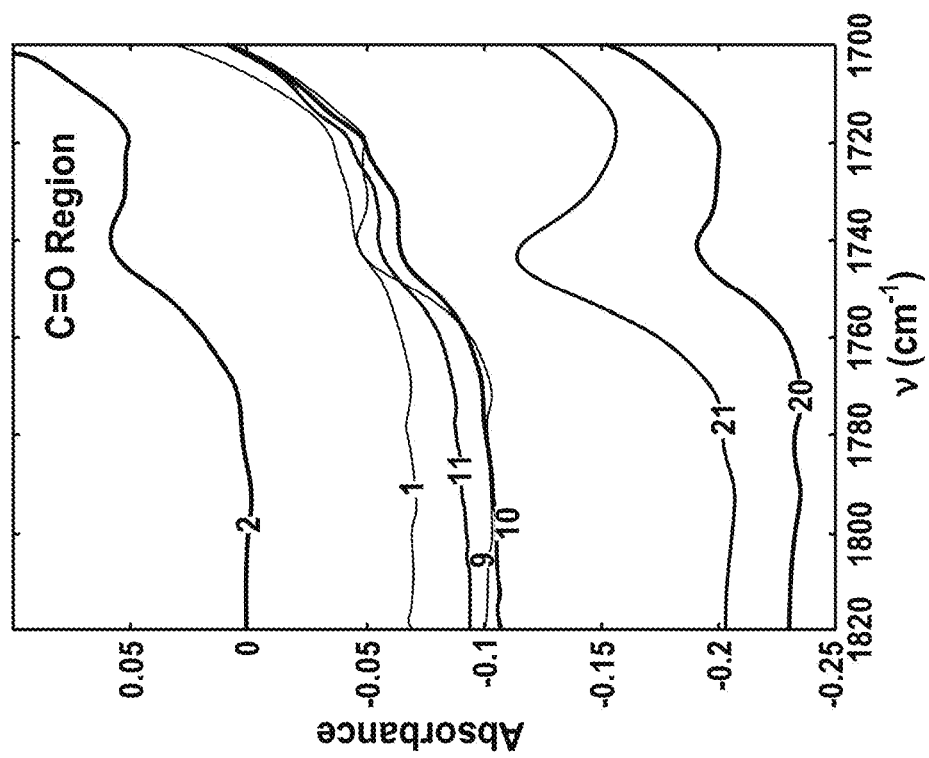

Our methods enable one to search and identify metrics that are common to individuals, as well as those that vary with individuals. The CCML Library is a unique source of tissue information because the samples are not fixed. These samples still contain lipid and water and are likely to have less denatured protein. While many of the previous examples focus on one particular case, it is fruitful to extract information from all of the cases. We performed a 25 cluster preliminary k-means cluster analysis on the whole CCML Library and the same five peak ratios metrics (1744/1244, 2924/1544, 1016/1080, 1744/1162, and 1080/3290) as shown in FIG. 19. FIG. 19 illustrates preliminary k-means cluster analysis of the CCML Library using 25 clusters and 5 IR metrics from FIG. 7. The 8 clusters shown above (out of the 25) show contributions from each and every case and are promising candidates for universal discrimination of colorectal cancer metastatic to the liver. Out of the 25 clusters, only eight show contributions from each case and therefore show potential for universal discrimination of colorectal cancer metastatic to the liver. The other clusters reveal variations between individual patients that may be used in future metrics. The IR spectra of clusters common across individuals in regions of interest are shown in FIGS. 20A and 20B. FIGS. 20A and 20B illustrate that IR spectra of k-means cluster groups which are common to all cases in the CCML Library with colors that match FIG. 12 and cluster numbers. Green and blue (clusters #20, #9, and #21) are nontumor with #21 closest to the tumor. Hot colors correspond to tumor including clusters #1, #3, #6, #11, and #16. The C═O region corresponds to ester-linked fats and shows systematic trends, as does the glycogen region. Again, cool colors were used for nontumor clusters and hot colors for those of tumors. The differences enable the development of promising peak ratio metrics, the kind that are best for the Fast IR Probe.

Figure 21A:
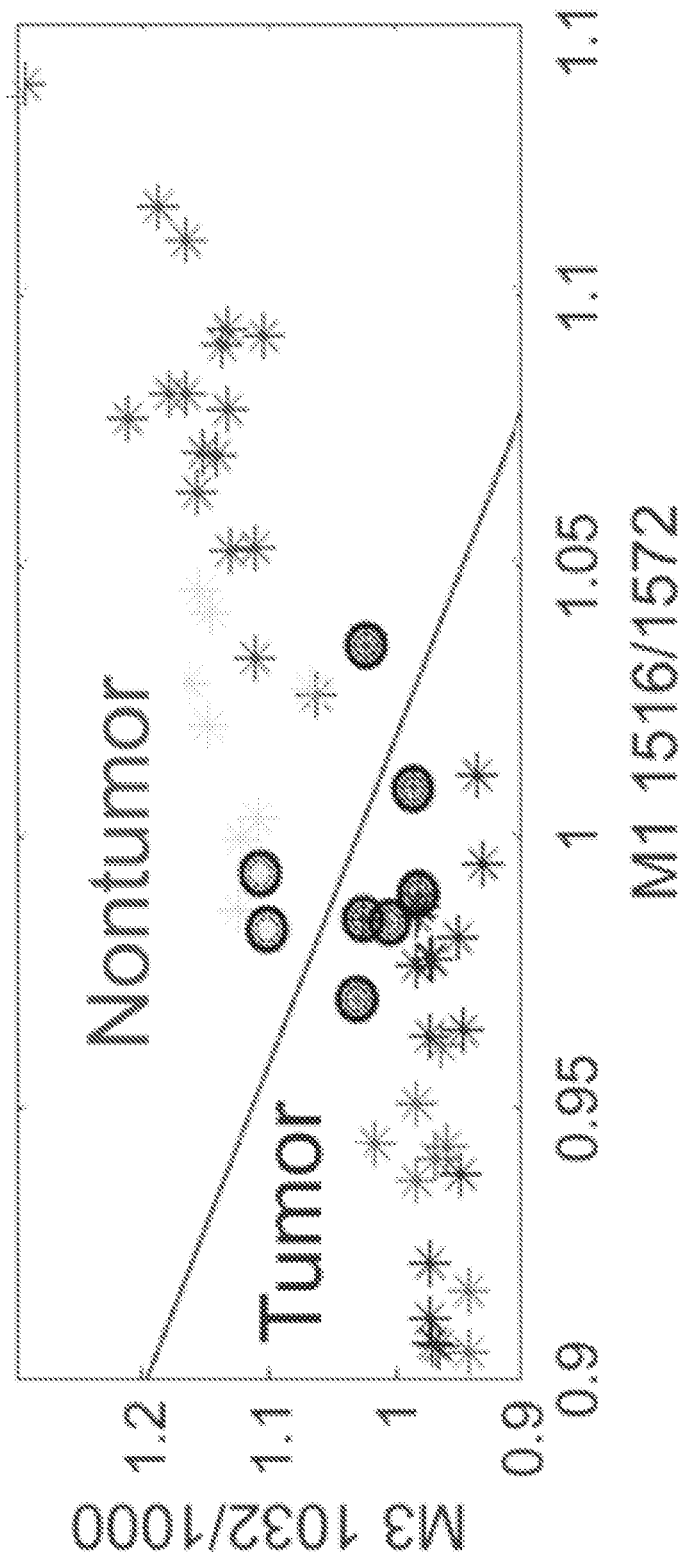
FIGS. 21A and 21B illustrate SVM results of proof of concept probe experiment on two cases of colorectal cancer metastatic two the liver showing good separation where
Figure 21B:
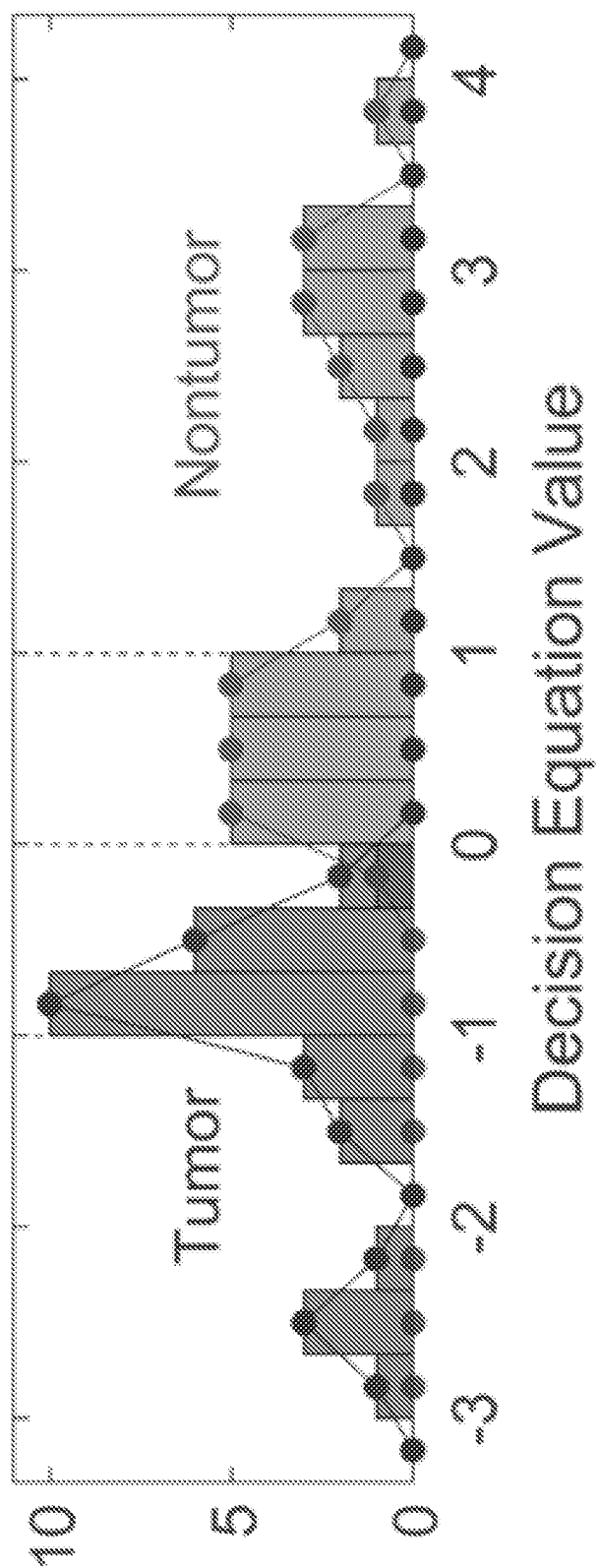

Example 2—SVM Results of Proof of Concept Probe Experiment on Two Cases of Colorectal Cancer Metastatic Two the Liver Showing Good Separation Referring back to FIG. 6, bottom panel, absorptions at promising wavelengths were used to construct IR metrics (M1, M2, and M3), which are ratios of absorption at the wavenumbers indicated with dotted lines in FIG. 6, bottom panel. They were optimized for separation. A plot of the IR metrics M3 vs M1 in FIG. 21A shows good separation of the tumor and nontumor scores. The metric scores were analyzed with a linear SVM program (supervised learning algorithm) which finds a hyperplane (in this case the black trace or the maximum margin line in FIG. 21A) that optimally separates the two groups of data (blue and cyan are nontumor, red and magenta are tumor) using only data near the boundary, i.e. the circled support vectors lying between the two groups. The linear SVM decision equation gives the perpendicular distance and direction of a test metric in scaled metric space from the optimized hyperplane:

$$d=b+\Sigma\alpha_i(S_i,'|f_j(T_j+o_j))i$$

where i is an index over the support vectors, j is an index over the metrics, b is the bias constant, $\alpha i$ are the weights, $S_{i,j'}$ are the scaled support vectors, $f_j$ is a multiplicative scaling factor, $o_j$ is an offset, and $T_j$ is the metric data to be tested. Test data is part of a group, such as nontumor or tumor, if d>0 (we call this a soft margin criteria, i.e. if data is on one side or other of the d=0 line). The SVM hard statistical margin extends from −1 to 1 as indicated with dotted vertical lines in FIG. 21B. Ideally this region is devoid of data, but with tissues one can expect some population. The parameters b, $\alpha_{i,i,j'}$, $f_j$, and $o_j$ are output as text or Excel files by our programs and can be input to new programs independent of the original SVM program to calculate decision equation values of data to be tested for cancer, such as for use with embodiments of the Fast Infrared Cancer Probe described herein. A histogram of the decision equation d values for each data point is presented in FIG. 21B showing good separation about the maximized margin. Note that the histogram of SVM decision equation scores is one dimensional even when more than three metrics are employed, i.e. even with hyperdimensional sets of metrics, for instance if we used every wavelength in the IR spectrum. The resulting histogram associated with use of every wavelength in the spectrum is shown in FIG. 22A, which exhibits a perfect hard SVM margin. A key issue relates to how many wavelengths can be omitted without sacrificing discrimination of cancer.

Figure 23:
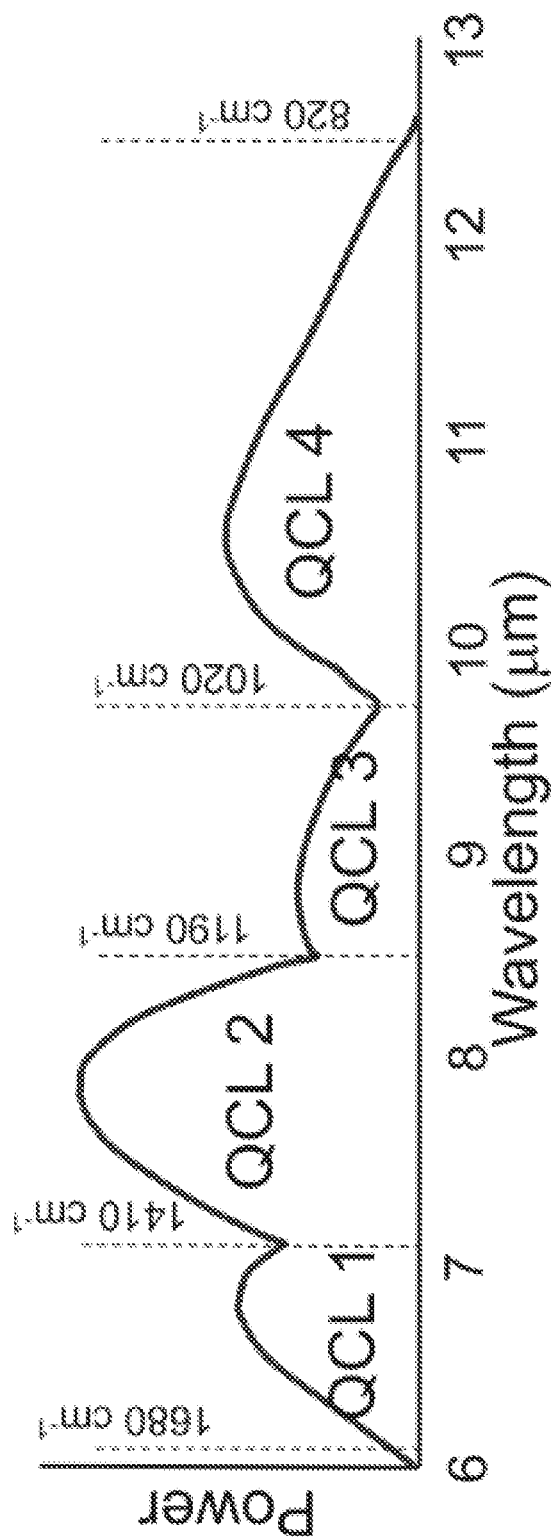
FIG. 23 shows typical spectral ranges of the four quantum cascade lasers (QCLs) found inside the most broadly tunable QCL systems.
Figure 24A:
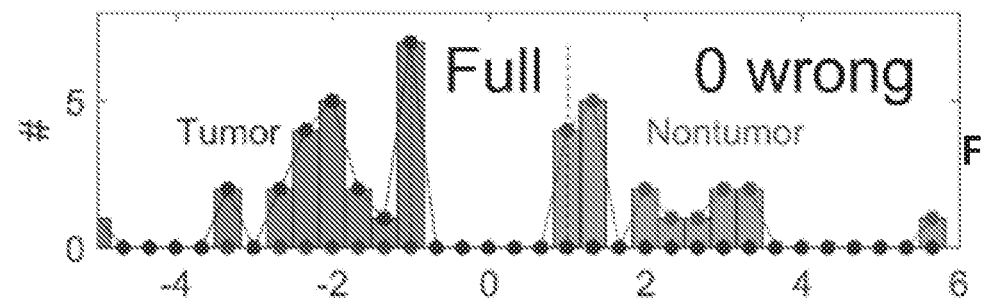
FIGS. 24A-24E show decision equation histograms for the full spectra range (24A) with no errors and then the four QCL ranges defined in FIG. 23 showing 0, 4, 3, and 2 errors out of 57 for QCL 1, QCL 2, QCL 3, and QCL 4, respectively.
Figure 24B:
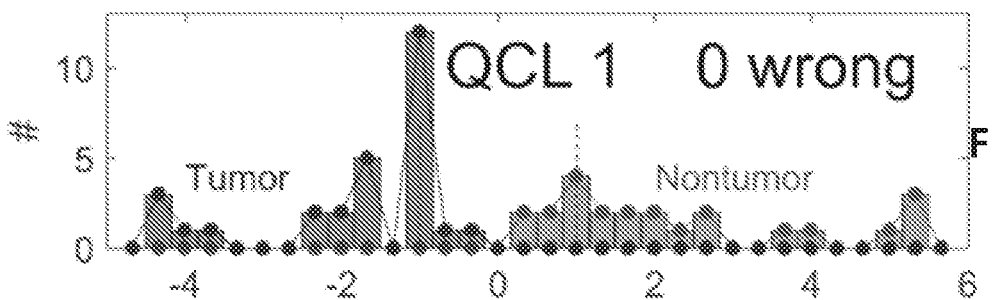
Figure 24C:
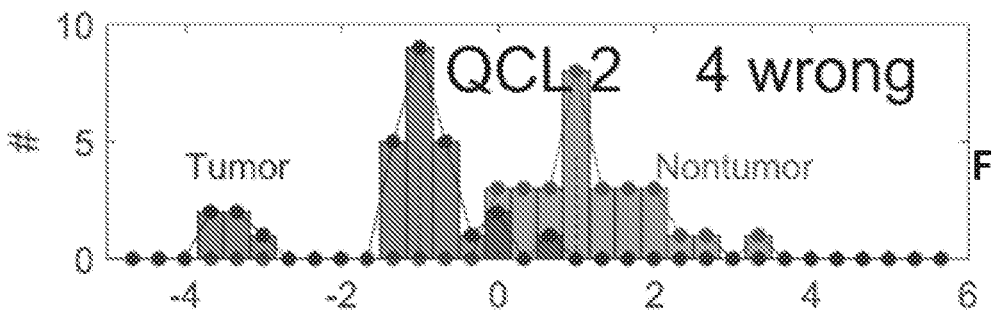
Figure 24D:
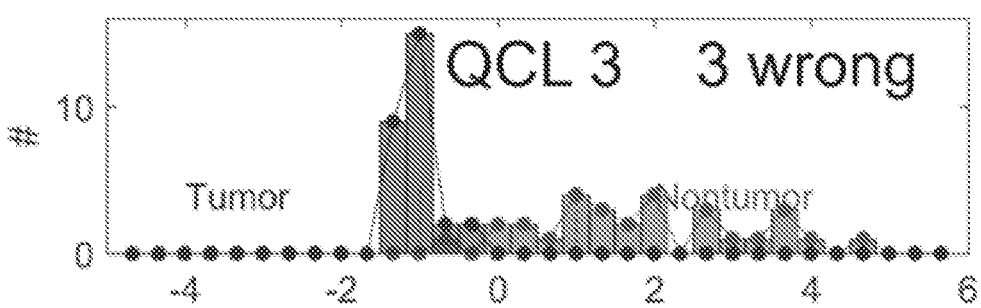
Figure 24E:
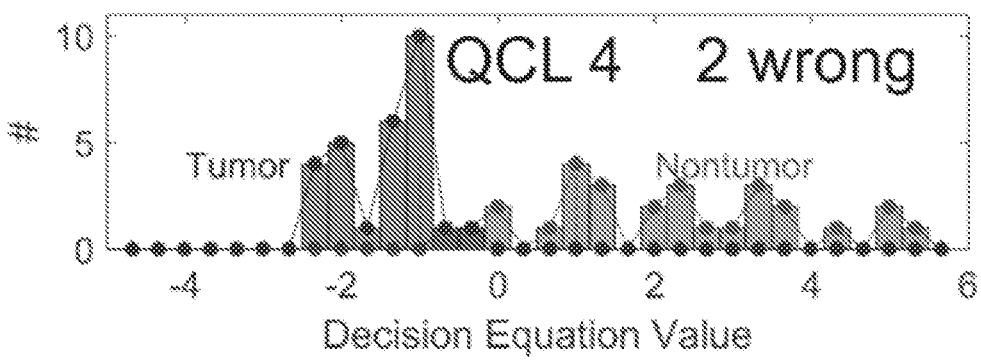

Statistical aspects of this data analysis involve the number of: (i) cases, (ii) measurements per case, (iii) and wavelengths used to obtain a confident decision. Concerning (i), collection from more than two cases is essential and proposed. Concerning (ii), each of the 57 measurements required 2.0 min or 2.50 s per wavelength step. But a traditional FTIR system simultaneously makes measurements at all wavelengths, so there is no option to measure at a selected set of wavelengths. However, a QCL system could make measurements 10 times faster at the same S/N (Daylight Solutions) and at only 6 out of the effective 451 wavelengths. Together this is a possible gain in speed factor of ~750. Measurements of 0.25 s per wavelength step for 6 wavelengths would take 1.5 s, hence the use of the word "Fast" in the disclosed invention. Concerning (iii), the FIG. 22B reveals the degradation of the separation gap with a reduction in # of wavelengths by comparing the decision equation histograms using 6 wavelengths (bottom) to the full spectrum of 451 wavelengths (top). It appears reasonable by initial results that one can reduce the number of wavelengths to five or six, i.e. the bottom histogram in FIG. 22B still has a gap between tumor and nontumor. Preliminary experiments show that it is reasonable to make accurate decisions with only 5 wavelengths. We propose measuring how the gap fills with reduction in the number of wavelengths However, there is a caveat that broadly tunable QCL systems currently contain four separate QCLs that program like one device—each with its own range, as shown in FIG. 23. A single QCL can jump between wavelengths on a ms timescale, but to jump from one QCL to another requires seconds. So, studies are proposed and illustrated in FIGS. 24A-24E dividing the full spectral range that we will measure into four segments that match single QCLs (see FIG. 23) in order to identify which of the four gives the best separation of tumor and nontumor (highest correct classification rate). In each case as the number of wavelengths is reduced, there is pushing of decision equation values into the previously perfect SVM maximum margin. QCL1 (1410-1680 cm$^{-1}$) shows zero errors, while QCL2 shows 4 errors. For these two cases of colorectal cancer metastatic to the liver, QCL1 would be the best choice. These studies enable embodiments of the disclosed invention to have one QCL, not four, thereby making it less expensive, which is an important practical consideration.

Figure 25:
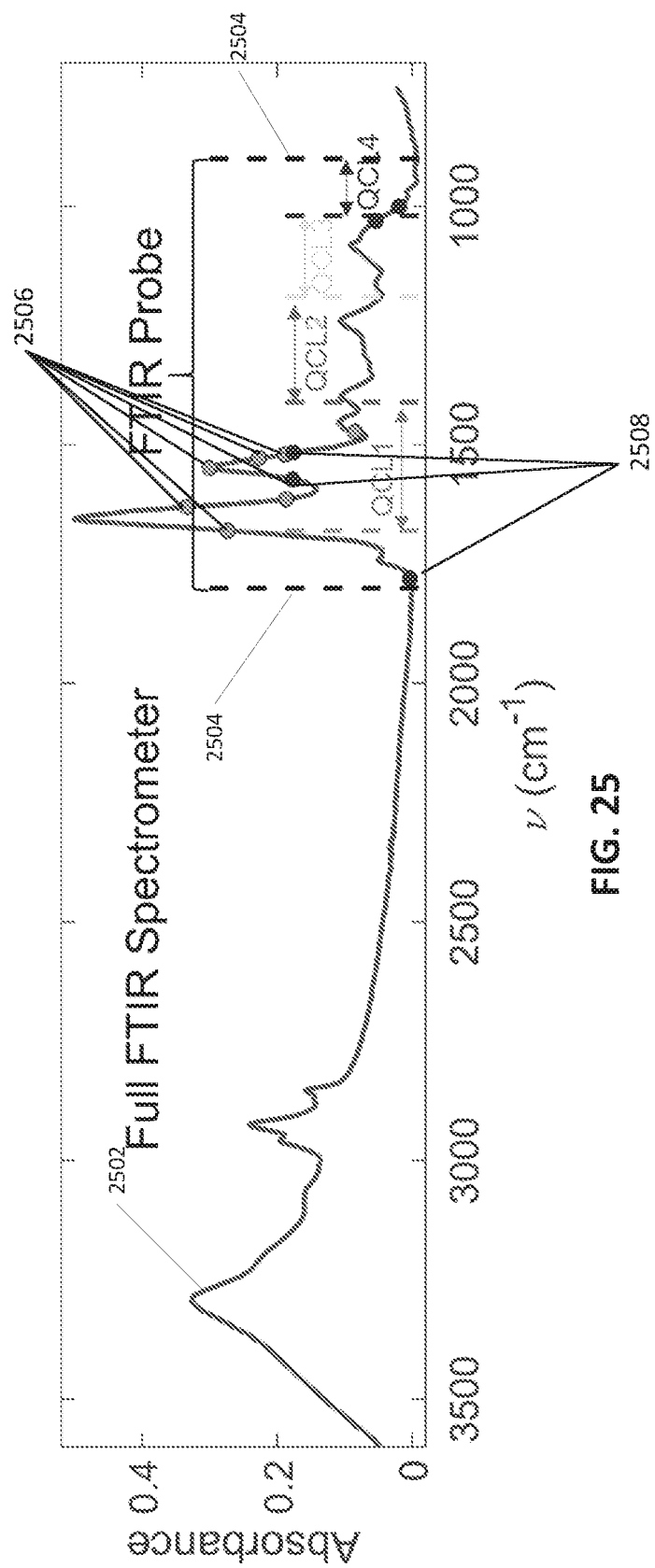
FIG. 25 illustrates a summary of wavelength issues regarding probes and QCL systems. The blue trace 2502 is the average IR spectrum of liver tissue from tissue slice studies showing most of the full FTIR range. The black vertical dotted lines 2504 define the range of the ATR probe on our FTIR spectrometer. The ranges of the four QCLs inside a typical broadly tunable laser device are indicated with color dotted lines. Seven wavelengths that work well with QCL 1 (FIG. 22B and FIG. 29B) are shown with green filled circles 2506 and five wavelengths (FIG. 21B) that work well with a broadly tunable QCL system are shown with red filled circles 2508.

Recalling FIG. 21B, it is possible to have one error out of 57 with five well-chosen wavelengths, however the wavelengths in that example extend over three of the four QCL ranges. So, we performed a new SVM analysis using 6 wavelengths (absorption at 1410, 1472, 1542, 1584, and 1614 cm$^{-1}$ is ratioed to that at 1510 cm$^{-1}$) from only QCL 1 as shown in FIG. 22B. This histogram has zero errors out of 57 and needs only 6 wavelengths from one QCL. If more than 6 wavelengths are needed to get a desired correct classification rate, then more wavelengths can be used and the probe gets slower, but it maintains a critical accuracy in detecting cancer. FIG. 25 shows an IR spectrum summarizing the wavelength issues discovered by our proof-of-concept liver resection results regarding the use of probes for both FTIR and QCLs. In general, the best specific wavelengths and number of wavelengths to change depending on the tissue or cancer type being interrogated, which lends itself for a tunable laser system as described herein.

Proof-of-Concept Probe Experiment with Skin Cancer.

5.4 million cases of nonmelanoma skin cancer (basal and squamous cell carcinoma) were treated in 3.3 million people in the US in 2012. There are more new cases of skin cancer than the combined incidence of breast, prostate, lung and colon cancer, but they are not tracked by the central cancer registries since they are not as lethal. One in five Americans will develop skin cancer over their lifetime and the rates are increasing.

Figure 28A:
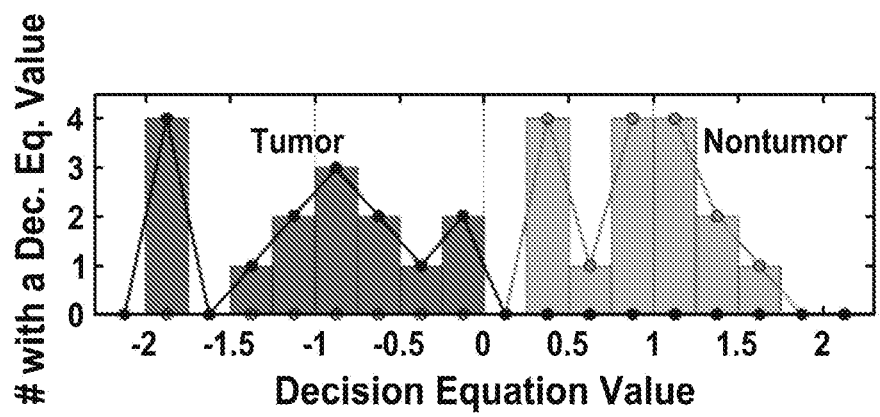
FIGS. 28A and 28B illustrate a histogram of decision equation values for SKH1 live mouse skin probe measurements using a 0.25 bin size (FIG. 28A), and 28B, a metric plot with SVM decision curve overlaid with measurements on healthy human skin showing good correspondence with the SKH1 mouse results.
Figure 28B:
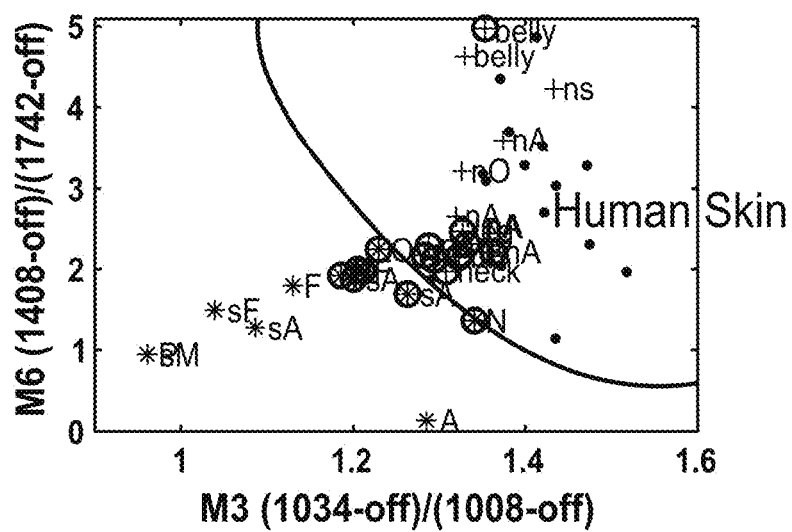

The SKH1 mouse model of UV-induced cutaneous squamous cell carcinoma (SCC) is an accepted murine model for studying SCC development in that it very closely recapitulates the human disease. This disease involves multiple cell types including keratinocytes, fibroblasts, endothelial cells, and infiltrating immune and inflammatory cells and the interplay between these cell types during UV-mediated skin cancer initiation, promotion, and progression and it cannot be modeled ex vivo. Under the University PHS Welfare Assurance number, A3261-01, and our IACUC protocol (2010A00000083), we recorded FTIR probe spectra (4 cm$^{-1}$ resolution, 700-1800 cm$^{-1}$, 1101 steps of 1 cm$^{-1}$, 25 scans, PE Spectrum 100) on one live SKH1 mouse with skin tumors in week 16 after 10 initial weeks of UV treatments as shown in FIG. 26A. It took 2.5 minutes to record each spectrum and spectra were recorded on and off skin tumors as shown in FIG. 26B. All of the tumor spectra were less intense because the fiber loop probe penetrates skin tumors less deeply as they are less elastic. Three times the average tumor spectrum was subtracted from the average nontumor spectrum giving the difference spectrum in FIG. 26C identifying the most important wavelengths. Good IR Metrics were extracted from the ratio of absorption at 1034 and 1008 cm$^{-1}$ (M3) and 1408 and 1742 cm$^{-1}$ (M6) with corrective offsets at the average of absorption at 1800 and 1770 cm$^{-1}$ (FIG. 27B). The letters indicate tumors as shown in FIG. 27A. Tumors labeled as A, D, B, E and L in FIG. 27A were "scabbed-over" and we could not get enough signal, however an "s" before the letter means that the spectrum was recorded on the side of the tumor which works. In the nontumor region, "n" before the tumor label indicates that the nontumor spectrum was recorded on unaffected skin in the vicinity of that tumor. The results were analyzed with a nonlinear radial basis function (rbf) SVM. The decision equation is $$d = \text{bias} + \Sigma \alpha_i \, e^{-12\sigma^2 ((S_i, j' - f_j(T_j - o_j))(S_i, j' - f_j(T_j + o_j)))_i}$$

where i is an index over the support vectors, Tj are the metrics to be tested, and $S_i$,j', bias, $\alpha_i$, $f_j$, and $o_j$ are outputs of the SVM program. The histogram of d values is given in FIG. 28A and the separating SVM curve is given in black in FIG. 27B, i.e. d=0. Finally, we made measurements of healthy human skin on our faces and fingertips and have overlaid the resulting IR metrics on the mouse metric plot in FIG. 28B. This data is not publishable, but it gives confidence in the decision equations for SKH1 mice as being applicable to humans.

Figure 29A:
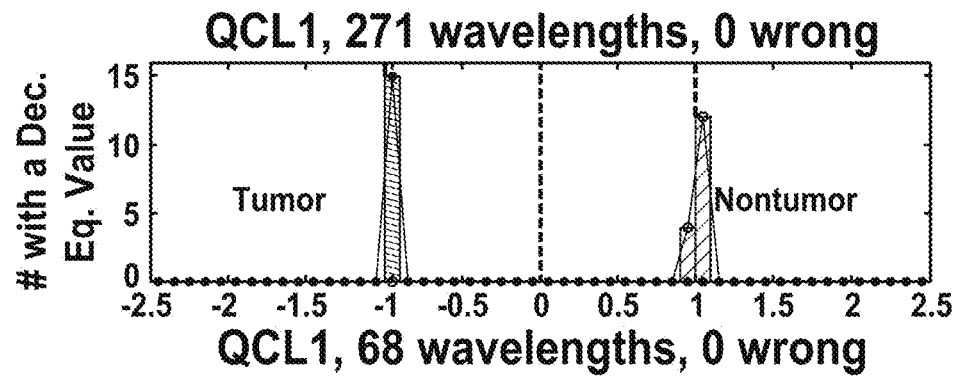
FIGS. 29A-29E illustrate histograms of decision equation values for skin tumors in a SKH1 mouse using variable numbers of wavelengths where
Figure 29B:
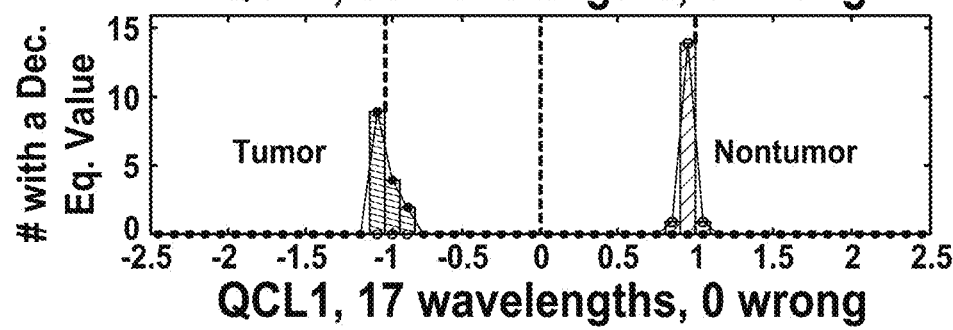
Figure 29C:
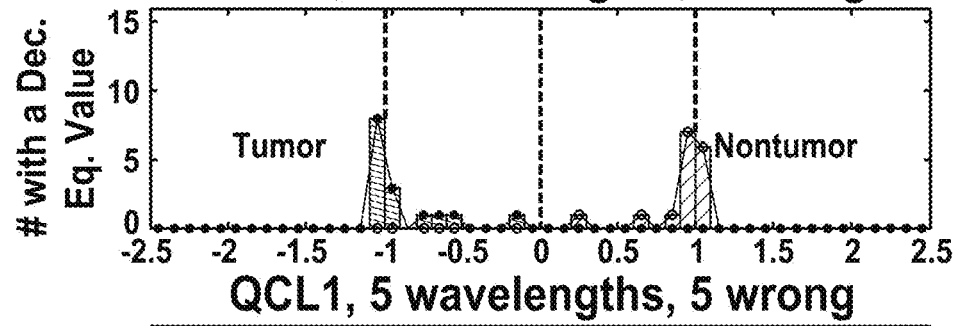
Figure 29D:
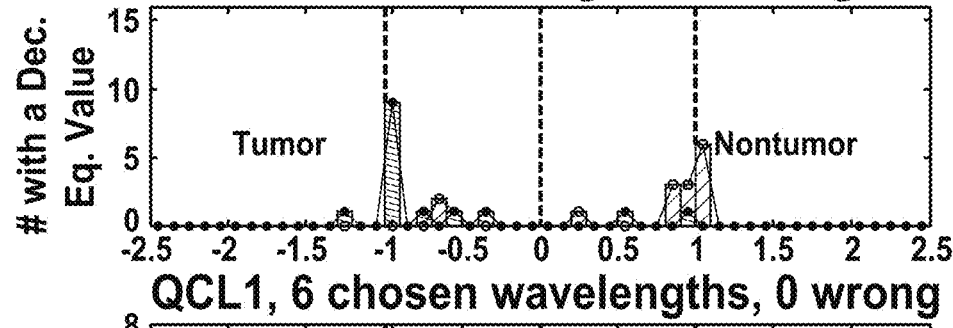

Statistical aspects of this data analysis again involve the number of: (i) cases, (ii) measurements per case, (iii) and wavelengths used to obtain a confident decision. We have proposed a preclinical SKH1 mouse study which will get data on 5 different mice (with 5 controls) and likely more than 25 tumors. In this experiment (see FIG. 26B), there is a clear separation by intensity owing to the difference in elasticity of normal skin and a tumor. However, we desire the more reliable biomolecular markers, so all of the spectral data was ratioed to absorbance at 1530 cm$^{-1}$ removing the physical elasticity issue from the metrics. We performed an rbf SVM with the full spectrum (1101 wavelengths) which produced a perfect classification (no errors) with negligible occurrence in the SVM statistical margin (region from −1 to 1) with all absorbances ratioed to 1530 cm$^{-1}$. Next, we reduced the wavelengths to the 271 available in the QCL 1 region (1410-1680 cm$^{-1}$, see FIG. 23) producing the decision equation histogram shown at FIG. 29A. Again, we find a perfect classification (no errors) and negligible occurrence in the SVM statistical margin. A sequence of SVM calculations were performed keeping only 1 of every 2, 4, 8, 16, 32, 64, 128 wavelengths and the resulting decision equation histograms are shown for 1 of 4 (68 wavelengths), 1 of 16 (17 wavelengths), and 1 of 64 (5 wavelengths) in FIGS. 29B-29D. As we reduce the number of wavelengths in this systematic fashion, d values begin to spread into the SVM statistical margin region, but they do not spread past the d=0 decision line until one gets to about 5 wavelengths. This verifies that the reduction of wavelengths needed to make embodiments of the disclosed Fast Infrared Cancer Probe "fast" is feasible.

Figure 29E:
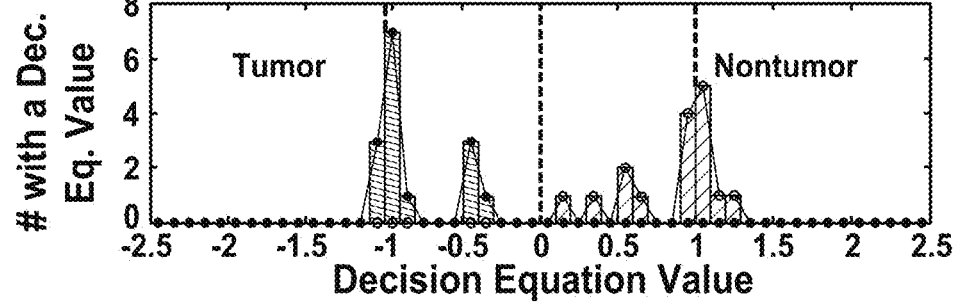

FIG. 29E shows a zero error decision equation histogram for 6 critical wavelengths including absorbance at 1488, 1521, 1585, 1593, and 1644 cm$^{-1}$ ratioed to that at 1530 cm$^{-1}$. Contrast this result with the last, 5 wavelength result in FIG. 29D, which shows 4 or so errors. The critical wavelengths tend to be a rapidly changing portions of the IR tissue spectrum. We are actively engaged in the search for critical wavelengths and a minimal number of wavelengths to produce an acceptably small number of incorrect classifications. Use of the Fast Infrared Cancer Probe with 5 or so wavelengths can yield 1000s of measurements in an afternoon which will give us a statistically meaningful % correct classification with an error bar that expresses the probability of an incorrect classification, both false negatives and positives. In other words, a decision equation with 7 or so wavelengths are likely to have acceptable gaps. If we need more wavelengths, then the probe gets slower, but maintains accuracy in detecting cancer. If a measurement and decision took 5 seconds, this would still be acceptable in a dermatological exam room. Clearly, the mouse results are meaningful, an excellent separation has been achieved, and there is great potential for detecting skin cancer in humans.

The QCL tunable laser system offers flexibility enabling adaptation to harder problems. In proposed preclinical trials, we are devising an experiment where the probe can be tested on cancerous lesions, noncancerous lesions, and normal skin, i.e. there are three groups to discern, not two. Also, SKH1 mice can have tumors analyzed for whether they are benign or malignant. These discriminations might require more wavelengths and the QCL system affords that possibility.

Merged IR and H&E Metrics.

Figure 30B:
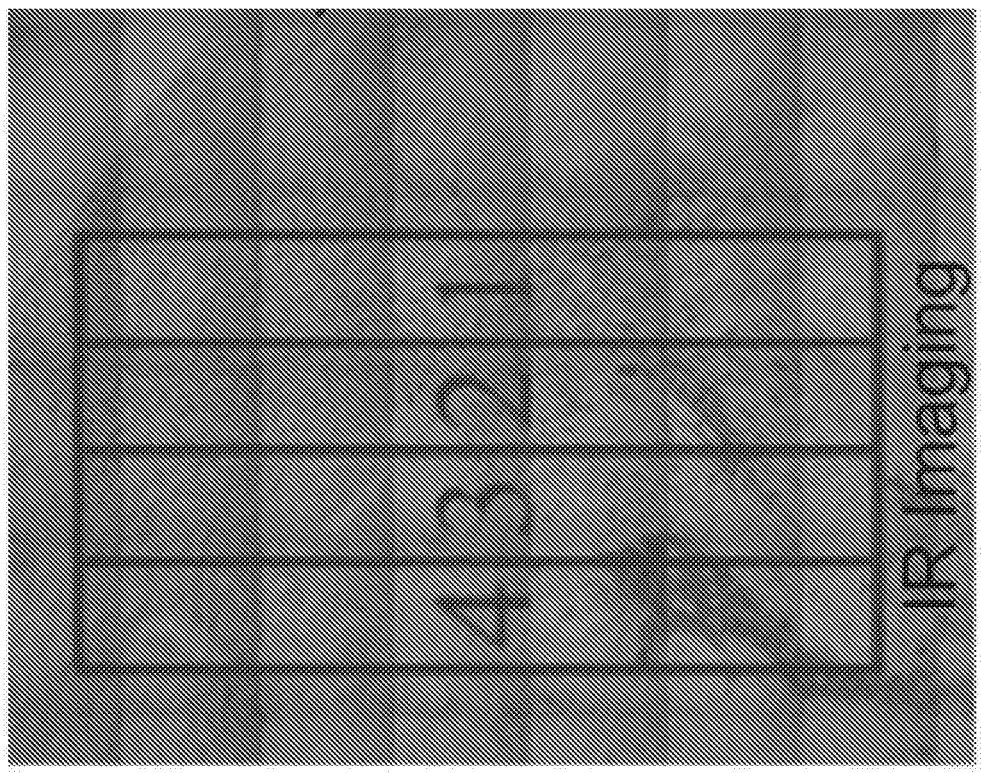
FIGS. 30A and 30B illustrate IR imaging (FIG. 30B) and H&E stain image (FIG. 30A) were recorded on the identical tissue slice of colorectal cancer metastatic to the liver as indicated with the red boxes. The IR was recorded in 4 smaller boxes that are merged into one by software programs.
Figure 30A:
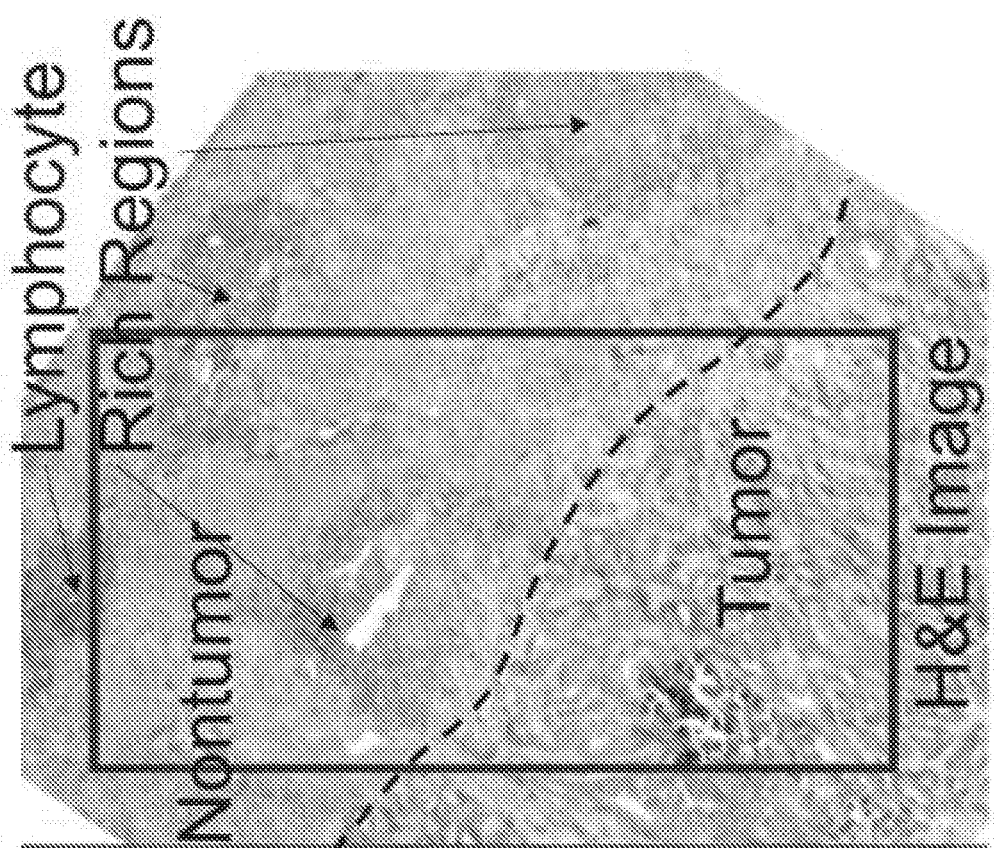

Since H&E imaging provides the most common standard for evaluating the surgeon's margin in liver resections, it is important to correlate our new IR metrics with those extracted from H&E imaging. This speaks to the medical community's acceptance of new IR metrics. We uniquely merge these metrics at input before performing SVM routines and our results correlate the IR with the H&E metrics. Experimentally this means performing tissue slice imaging on the exact same tissue with both H&E and IR. Such studies are proposed in parallel with the probe experiments mentioned in the previous two sections. With success, our new IR work will be connected to the current common standard for diagnosing cancer in liver resections. As an example, consider a region of tissue slice in FIG. 30A in the box from a consenting patient with colorectal cancer metastatic to the liver. First we obtained IR imaging data (FIG. 30B) and afterwards an H&E stain (FIG. 30A) on the same tissue. Since the H&E pixel grid was 487×255 and the IR image was 352×192 on the same 2.2 mm×1.2 mm region, a program was written to assign the closest IR pixel and metrics to each H&E pixel. K-means cluster analysis was run with merged H&E an IR metrics and clusters were assigned to three groups: tumor, nontumor, and lymphocyte rich regions. Out of 16 optical metrics calculated based on the RGB values from the H&E image, seven were chosen as best at separating tumor including the CIELab values (L*, a*, b* from the Int. Commission on Illumination), and four greyscale level co-occurrence matrix values known as energy, contrast, correlation, and homogeneity. These were added to five IR metrics of ratios of absorbance from our previous work and all 12 are presented as images in FIGS. 31A and 31B. Visual inspection reveals that the IR metrics (FIG. 31B) are better at detecting the tumor, at least at these resolutions. A k-means cluster analysis was done with 20 clusters and three clusters were identified as lymphocyte rich regions, three were identified as nontumor, and the rest were dominated by tumor and some groups that haven't been separated yet. The clusters were merged into lymphocyte, nontumor, and tumor groups and radial basis function SVM decision equations were obtained for each group against all not in the group. The decision equation values are presented as histograms in FIG. 32A and these have been converted to images of each group in FIG. 32B for comparison to the H&E stain in FIG. 32C. We obtain a correlated set of centroids (average metric scores) within each group, so now we have determined the correlation between IR and H&E metrics. This is very important as H&E is the most common standard for evaluating the surgeon's margin in liver resections. The correlation of the morphology dominated H&E stain image with the biomolecule dominated IR metrics provides new avenues for discriminating cancer and for assessing biochemical processes. This decision equations are the most critical scientific aspect of the project and we propose to determine decision equations for groups including tumor, nontumor, lymphocytes, blood, venules, arterioles, bile ducts, and nuclei in liver tissue.

Statistical considerations are different with tissue slice imaging as compared to probe measurements. If 10 consenting patients yield a 2 mm×2 mm tissue slice each, there will be 302 pixels by 320 pixel (at 6.25 µm per pixel) yielding 102,400 IR spectra. The H&E stain images of the same region will have at least twice as many pixels and this could be 20 times more (at 0.5 µm per pixel). So the libraries of IR spectra will involve more than a million IR spectra with typically 1626 wavelength steps with our instrument (PE Spotlight 300). The challenges here concern performing SVM on such large data sets and in obtaining classifications for training. Our desktop computers allow about 2000 metric sets in the group and 2000 out of the group which are chosen at random for SVM training. Then the resulting decision equation is run on the whole set of 102,400 pixels as shown in the histograms of FIG. 32A. Clearly, the IR and H&E combination have great potential to identify both cancer and interesting tissues associated with the battle against cancer, i.e. the lymphocyte-rich regions also shown in FIG. 32B.

While embodiments of the system and methods described herein are generally described in relation to aid in resections of cancer tissues, additional applications reside in detecting skin cancer in a clinical setting. Skin cancer is the most common of all cancer types according to the American Cancer Society.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

Throughout this application, various publications may be referenced. The disclosures of these publications in their entireties are hereby incorporated by reference into this application in order to more fully describe the state of the art to which the methods and systems pertain.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method of discriminating tissue of a specimen, the method comprising:
    performing infrared (IR) spectroscopy on a specimen using a probe, wherein the IR spectroscopy is performed including by using only one single tunable Quantum Cascade Laser (QCL), having a specified output wavelength range, to a selected subset of IR wavelengths within the specified output wavelength range of the single tunable QCL for illuminating the specimen, wherein the selected subset of IR wavelengths is selected based on a correlation between IR absorbance data and histological data to discriminate normal tissue from abnormal tissue in the specimen;
    obtaining a portion of an IR spectrum from the specimen via the probe in response to the illuminating the specimen using the selected subset of IR wavelengths within the specified output wavelength range of the single tunable QCL; and
    evaluating the obtained portion of the IR spectrum using one or more metrics, wherein the one or more metrics discriminate normal tissue of the specimen from abnormal tissue of the specimen using response wavelengths in the obtained portion of the IR spectrum in response to the selected subset of IR wavelengths used for the illuminating the specimen.

2. The method of claim 1, wherein discriminating normal tissue of the specimen from abnormal tissue of the specimen comprises determining non-cancerous regions of the specimen from cancerous regions of the specimen using response wavelengths in the obtained portion of the IR spectrum in response to the selected subset of IR wavelengths used for the illuminating the specimen.

3. The method of claim 1, comprising using a plurality of QCLs having different specified output wavelength ranges for selecting the subset of IR wavelengths within the specified output wavelength range of the single tunable QCL.

4. The method of claim 1, further comprising identifying the normal tissue of the specimen from the abnormal tissue of the specimen using response wavelengths in the obtained portion of the IR spectrum in response to the selected subset of IR wavelengths used for the illuminating the specimen.

5. The method of claim 4, wherein the identifying, using response wavelengths in the obtained portion of the IR spectrum in response to the selected subset of IR wavelengths used for the illuminating the specimen, is used to provide an assessment of the surgical margin made in the operating room by a surgeon as the abnormal tissue is removed.

6. The method of claim 1, wherein the selected subset of IR wavelengths comprises 10 or fewer wavelengths.

7. The method of claim 6, wherein the selected subset of IR wavelengths comprises six wavelengths.

8. A system for discriminating tissue of a specimen, the system comprising:
    an infrared (IR) source;
    a probe in communication with the IR source via a fiber optic cable, wherein the probe is used to obtain a portion of an IR spectrum from the specimen in response to illuminations using a specified subset of IR wavelengths provided by the IR source over a first measurement time period;
    an IR detector, wherein the IR detector receives the portion of the IR spectrum from the probe via a fiber optic cable; and
    a computing device comprising a processor and a memory in communication with the processor, said memory comprising computer-executable instructions, wherein the computing device receives a signal representative of the detected portion of the IR spectrum from the IR detector and said computer-executable instructions cause the processor to evaluate the obtained portion of IR spectrum using one or more metrics, wherein the one or more metrics discriminate normal tissue of the specimen from abnormal tissue of the specimen using selected wavelengths that are pre-selected to characterize (1) one or more spectral response inflection points of the obtained portion of the IR spectrum over the same first measurement time period and (2) an absorbance vs. wavelength spectral response steepness of the same obtained portion of the IR spectrum obtained over the same first measurement time period in response to the same illuminations, to discriminate between the normal tissue and the abnormal tissue.

9. The system of claim 8, wherein the IR source comprises a single quantum cascade IR laser (QCL) that is a tunable mid-infrared laser with a selected subset of IR wavelengths, within the output wavelength range of the single QCL, that have been selected for detecting tissue specific chemical and molecular signatures to include, but not limited to, one or more of cancer, preneoplasia, steatosis or other intracellular accumulations, inflammation, and wound healing.

10. The system of claim 8, wherein the IR detector comprises a thermal microbolometer array detector.

11. The system of claim 8, wherein discriminating normal tissue of the specimen from abnormal tissue of the specimen comprises determining non-cancerous regions of the specimen from cancerous regions of the specimen using the selected wavelengths that are pre-selected to characterize (1) one or more spectral response inflection points and (2) a spectral response steepness, to discriminate between the normal tissue and the abnormal tissue.

12. The system of claim 8, further comprising the computing device executing computer-executable instructions stored in the memory that cause the processor to perform identifying the normal tissue of the specimen from the abnormal tissue of the specimen.

13. The system of claim 12, wherein the computing device includes or is coupled to a display that displays the identified normal tissue of the specimen and the identified abnormal tissue of the specimen to a surgeon in an operating room to provide an assessment of the surgical margin made in the operating room by the surgeon as the abnormal tissue is removed.

14. The system of claim 12, wherein the computing device includes or is coupled to a display that displays the identified normal tissue of the specimen or the identified abnormal tissue of the specimen to a surgeon in an operating room to provide an assessment of the surgical margin made in the operating room by the surgeon as the abnormal tissue is removed.

15. The system of claim 8, wherein the selected wavelengths include a subset of IR wavelengths that comprises 10 or fewer wavelengths.

16. The system of claim 15, wherein the selected subset of IR wavelengths comprises six or fewer wavelengths.

17. A non-transitory computer-readable medium comprising computer-executable code stored thereon for causing a computing device to perform the method of:
receiving a portion of an IR spectrum of a specimen from a probe, wherein the probe has been used to perform infrared (IR) spectroscopy illumination of the specimen tuned using a specified subset of IR wavelengths that are selected from a set of IR wavelengths defined by an IR band of interest for spectroscopic discrimination of normal tissue from abnormal tissue, wherein the specified subset of IR wavelengths is selected by using a Support Vector Machine (SVM) supervised machine learning (ML) model trained using IR absorption spectra of specimens and corresponding histology training inputs from corresponding specimens, wherein the specified subset of IR wavelengths is selected based on a correlation between IR absorbance data and histological data to discriminate normal tissue from abnormal tissue in the specimen; and
evaluating the obtained portion of the IR spectrum using one or more metrics, wherein the one or more metrics determine normal tissue of the specimen from abnormal tissue of the specimen.

18. The computer-readable medium of claim 17, wherein determining the normal tissue of the specimen from the abnormal tissue of the specimen comprises determining non-cancerous regions of the specimen from cancerous regions of the specimen.

19. The computer-readable medium of claim 17, wherein the method further comprises identifying the normal tissue of the specimen from the abnormal tissue of the specimen.

20. The computer-readable medium of claim 19, wherein the method further comprises using the identifying to provide an assessment of the surgical margin made in the operating room by a surgeon as the abnormal tissue is removed.

21. The computer-readable medium of claim 17, wherein the specified subset of IR wavelengths comprises 10 or fewer wavelengths.

22. The computer-readable medium of claim 21, wherein the specified subset of IR wavelengths comprises six or fewer wavelengths.

23. A method of discriminating tissue of a specimen, the method comprising:
performing infrared (IR) spectroscopy on a specimen using a probe, wherein the IR spectroscopy is performed including by using a tunable Quantum Cascade Laser (QCL) to a selected subset of IR wavelengths for illuminating the specimen, the selected subset of IR wavelengths selected based on a correlation between IR absorbance data and histological data to discriminate normal tissue from abnormal tissue in the specimen;
obtaining a portion of an IR spectrum from the specimen via the probe in response to the illuminating the specimen using the selected subset of IR wavelengths; and
evaluating the obtained portion of the IR spectrum using one or more metrics, wherein the one or more metrics discriminate normal tissue of the specimen from abnormal tissue of the specimen using response wavelengths in the obtained portion of the IR spectrum in response to the selected subset of IR wavelengths used for the illuminating the specimen.

24. The method of claim 23, wherein the specified subset of IR wavelengths are selected to be limited to 10 or fewer wavelengths.

25. The method of claim 23, comprising tuning the tunable QCL having a specified output wavelength range to a specified subset of IR wavelengths selected to be fewer than 451 wavelengths.

26. The method of claim 23, comprising tuning the tunable QCL to a specified subset of IR wavelengths selected to include one or more wavelengths in an amide I band.

27. The method of claim 23, comprising tuning the tunable QCL to a specified subset of IR wavelengths selected to include one or more wavelengths in an amide II band.

28. The method of claim 23, comprising tuning the tunable QCL to a specified subset of IR wavelengths selected using a Figure of Merit (FOM) based on a spread of a metric, based on a ratio of absorbance determined using a machine learning technique.

29. The method of claim 23, comprising tuning the tunable QCL to a specified subset of IR wavelengths selected using a metric based on a spectral response steepness characteristic.

30. The method of claim 23, wherein the selected subset of IR wavelengths is selected using a ratio of absorbances at the selected IR wavelengths.

31. The method of claim 23, wherein the selected subset of IR wavelengths is selected using a composite of multiple different metrics for the selecting the subset of IR wavelengths.

32. The method of claim 23, wherein the selected subset of IR wavelengths is selected using a machine learning model trained using:
   (1) a difference spectral response between a first spectral response from a histologically-classified tumor specimen and a second spectral response from a histologically-classified non-tumor specimen; and
   (2) a metric based on ratios of absorbances at maxima in the difference spectral response.

33. The method of claim 23, wherein the selected subset of IR wavelengths includes one or more selected wavelengths that are:
   (1) offset from spectral response peaks associated with the amide I and amide II bands; and
   (2) selected using a metric based on a ratio of absorbances.

34. The method of claim 23, wherein the selected subset of IR wavelengths is selected using:
   (1) a spectral response steepness on the high wavenumber side of an amide II band of protein backbones; and
   (2) a local spectral response maxima associated with a glycogen or other polysaccharide.

35. The method of claim 23, comprising selecting the subset of IR wavelengths using machine learning SVM training based on the correlation between IR imaging data and dye stain pixel grid data.

36. The method of claim 23, comprising tuning the tunable QCL to a specified subset of IR wavelengths selected using a metric based on a baseline corrected tissue spectra.

37. The method of claim 36, comprising tuning the tunable QCL to a specified subset of IR wavelengths selected using a metric based on a spectral response steepness characteristic of a side of an amide II band of protein backbones.

* * * * *